(12) United States Patent
McClure et al.

(10) Patent No.: US 6,329,397 B1
(45) Date of Patent: *Dec. 11, 2001

(54) HYDROXY PIPECOLATE HYDROXAMIC ACID DERIVATIVES

(75) Inventors: Kim F. McClure; Mark C. Noe; Michael A. Letavic, all of Mystic; Louis S. Chupak, Old Saybrook, all of CT (US)

(73) Assignee: Pfizer, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/372,946

(22) Filed: Aug. 12, 1999

Related U.S. Application Data

(60) Provisional application No. 60/096,232, filed on Aug. 12, 1998.

(51) Int. Cl.$^7$ .................. A61K 31/445; C07D 211/60
(52) U.S. Cl. ................. 514/330; 514/354; 546/16; 546/225; 546/245; 546/323
(58) Field of Search .............. 546/16, 225, 245, 546/323; 514/330, 354

(56) References Cited

U.S. PATENT DOCUMENTS 5,861,510 * 1/1999 Piscopio et al. ............... 544/131

FOREIGN PATENT DOCUMENTS

98/08815 * 3/1998 (WO).
98/34918 * 8/1998 (WO).

* cited by examiner

Primary Examiner—Ceila Chang
(74) Attorney, Agent, or Firm—Peter C. Richardson; Paul H. Ginsburg; Jeffrey N. Myers

(57) ABSTRACT

A compound of the formula wherein $R^1$, $R^2$ $R^3$, $R^4$ $R^5$, $R^6$, $R^7$, $R^8$, $R^9$ and Ar are as defined above, useful in the treatment of a condition selected from the group consisting of arthritis, cancer, and other diseases characterized by matrix metalloproteinase or mammalian reprolysin activity. In addition, the compounds of the present invention may be used in combination therapy with standard non-steroidal anti-inflammatory drugs (NSAID'S), COX-2 inhibitors and analgesics, and in combination with cytotoxic drugs such as adriamycin, daunomycin, cis-platinum, etoposide, taxol, taxotere and other alkaloids, such as vincristine, in the treatment of cancer.

68 Claims, No Drawings

HYDROXY PIPECOLATE HYDROXAMIC ACID DERIVATIVES

The present application is a Non-Provisional Continuation Application of U.S. Provisional Patent Application No. 60/096,232, filed Aug. 12, 1998.

BACKGROUND OF THE INVENTION

The present invention relates to hydroxy pipecolate hydroxamic acid derivatives, and to pharmaceutical compositions comprising such derivatives and to the use of such derivatives in the treatment of arthritis, cancer and other diseases.

The compounds of the present invention are inhibitors of zinc metalloendopeptidases, especially those belonging to the matrix metalloproteinase (also called MMP or matrixin) and reprolysin (also known as adamylsin) subfamilies of the metzincins (Rawlings, et al., *Methods in Enzymology*, 248, 183–228 (1995) and Stocker, et al., *Protein Science*, 4, 823–840 (1995)).

The MMP subfamily of enzymes, currently contains seventeen members (MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20). The MMP's are most well known for their role in regulating the turn-over of extracellular matrix proteins and as such play important roles in normal physiological processes such as reproduction, development and differentiation. In addition, the MMP's are expressed in many pathological situations in which abnormal connective tissue turnover is occurring. For example, MMP-13 an enzyme with potent activity at degrading type II collagen (the principal collagen in cartilage), has been demonstrated to be overexpressed in osteoarthritic cartilage (Mitchell, et al., *J. Clin. Invest.*, 97, 761 (1996)). Other MMPs (MMP-2, MMP-3, MMP-8, MMP-9, MMP-12) are also overexpressed in osteoarthritic cartilage and inhibition of some or all of these MMP's is expected to slow or block the accelerated loss of cartilage typical of joint diseases such as osteoarthritis or rheumatoid arthritis.

The mammalian reprolysins are known as ADAMs (A Disintegrin And Metalloproteinase) (Wolfberg, et al., *J. Cell Biol.*, 131, 275–278 (1995)) and contain a disintegrin domain in addition to a metalloproteinase-like domain. To date twenty-three distinct ADAM's have been identified.

ADAM-17, also known as tumor necrosis factor-alpha converting enzyme (TACE), is the most well known ADAM. ADAM-17 (TACE) is responsible for cleavage of cell bound tumor necrosis factor-alpha (TNF-α, also known as cachectin). TNF-α is recognized to be involved in many infectious and autoimmune diseases (W. Friers, *FEBS Letters*, 285, 199 (1991)). Furthermore, it has been shown that TNF-α is the prime mediator of the inflammatory response seen in sepsis and septic shock (Spooner, et al., *Clinical Immunology and Immunopathology*, 62 S11 (1992)). There are two forms of TNF-α, a type II membrane protein of relative molecular mass 26,000 (26 kD) and a soluble 17 kD form generated from the cell bound protein by specific proteolytic cleavage. The soluble 17 kD form of TNF-α is released by the cell and is associated with the deleterious effects of TNF-α. This form of TNF-α is also capable of acting at sites distant from the site of synthesis. Thus, inhibitors of TACE prevent the formation of soluble TNF-α and prevent the deleterious effects of the soluble factor.

Select compounds of the invention are potent inhibitors of aggrecanase, an enzyme important in the degradation of cartilage aggrecan. Aggrecanase is also believed to be an ADAM. The loss of aggrecan from the cartilage matrix is an important factor in the progression of joint diseases such as osteoarthritis and rheumatoid arthritis and inhibition of aggrecanase is expected to slow or block the loss of cartilage in these diseases.

Other ADAMs that have shown expression in pathological situations include ADAM TS-1 (Kuno, et al., *J. Biol. Chem.*, 272, 556–562 (1997)), and ADAM's 10, 12 and 15 (Wu, et al., *Biochem. Biophys. Res. Comm.*, 235, 437–442, (1997)). As knowledge of the expression, physiological substrates and disease association of the ADAM's increases the full significance of the role of inhibition of this class of enzymes will be appreciated.

The compounds of the invention are useful in the treatment of arthritis (including osteoarthritis and rheumatoid arthritis), inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, cancer (such as solid tumor cancer including colon cancer, breast cancer, lung cancer and prostrate cancer and hematopoietic malignancies including leukemias and lymphomas), tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis or septic shock.

The compounds of the present invention are also useful in the treatment of diseases in which inhibition of MMP's and/or ADAM's will provide therapeutic benefit, such as those characterized by matrix metalloproteinase or ADAM expression.

The present inventors have also discovered that it is possible to design inhibitors with differential metalloprotease and reprolysin activity (preferably TACE inhibitory activity).. One group of preferred inhibitors the inventors have been able to identify include those which selectively inhibit TACE preferentially over MMP-1. Another group of preferred inhibitors the inventors have been able to identify include those molecules which selectively inhibit TACE and matrix metalloprotease-13 (MMP-13) preferentially over MMP-1. Another group of preferred inhibitors the inventors have been able to identify include those molecules which selectively inhibit Aggrecanase and matrix metalloprotease-13 (MMP-13) preferentially over MMP-1. Another group of preferred inhibitors the inventors have been able to identify include those molecules which selectively inhibit Aggrecanase and TACE preferentially over MMP-1. Another group of preferred inhibitors the inventors have been able to identify include those molecules which selectively inhibit Aggrecanase preferentially over MMP-1.

Matrix metalloproteinase and reprolysin inhibitors are well known in the literature. Specifically, European Patent Publication 606,046, published Jul. 13, 1994 refers to ceratin heterocyclic MMP inhibitors. PCT Publication WO 98/08825 and WO 98/08815, both published Mar. 5, 1998, refer to certain cyclic hydroxamic acid MMP inhibitors. U.S. Pat. No. 5,861,510, issued Jan. 19, 1999, refers to cyclic arylsulfonylamino hydroxamic acids that are useful as MMP inhibitors. PCT Publication WO 98/34918, published Aug. 13, 1998, refers to cyclic hydroxamic acids including certain hydroxy substituted compounds that are useful as MMP inhibitors. PCT publications WO 96/27583 and WO 98/07697, published Mar. 7, 1996 and Feb. 26, 1998, respectively, refer to arylsulfonyl hydroxamic acids. PCT publication WO 98/03516, published Jan. 29, 1998, refers to phosphinates with MMP activity. PCT publication 98/33768, published Aug. 6, 1998, refers to N-unsubstituted arylsulfonylamino hydroxamic acids. European Patent Publication EP 935,963, published Aug. 18, 1999 refers to the use of MMP-13 selective inhibitors for the treatment of osteoarthritis. U.S. patent applications Ser. Nos. 09/290,022 09/287,930 and 09/287,508 filed Apr. 9, 1999, Apr. 7, 1999 and April 7, 1999 respectively, refer to methods of preparing hydroxamic acids. U.S. Provisional Patent Application entitled "Selective Inhibitors of Aggecanase in Osteoarthritis Treatment," filed Aug. 12, 1999 refers to MMP, Aggrecanase and TACE inhibitors and to additional methods of preparing hydroxamic acids. U.S. Non-Provisional Application entitled "TACE Inhibitors," filed Aug. 12, 1999, refers to heterocyclic hydroxamic acids. Each of the above referenced publications and applications is hereby incorporated by reference in its entirety.

SUMMARY OF THE INVENTION

The present invention relates to a compound of the formula

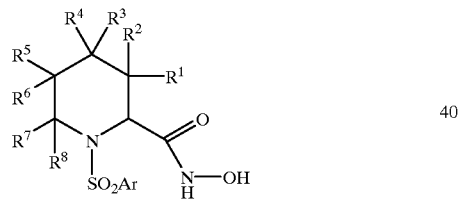

I or the pharmaceutically acceptable salts thereof, wherein $R^1$–$R^8$ are selected from the group consisting of hydroxy, $NH_2$, hydrogen, halogen (preferably chloro or fluoro), —CN, $(C_1-C_6)$alkyl, $(C_2-C_6)$alkenyl, $(C_6-C_{10})$aryl$(C_2-C_6)$alkenyl, $(C_2-C_9)$heteroaryl $(C_2-C_6)$alkenyl, $(C_2-C_6)$alkynyl, $(C_6-C_{10})$aryl$(C_2-C_6)$ alkynyl, $(C_2-C_9)$heteroaryl$(C_2-C_6)$alkynyl, $(C_1-C_6)$ alkylamino, $[(C_1-C_6)$alkyl$]_2$amino, $(C_1-C_6)$alkylthio, $(C_1-C_6)$alkoxy, perfluoro$(C_1-C_6)$alkyl, perfluoro $(C_1-C_6)$alkoxy, $(C_6-C_{10})$aryl, $(C_2-C_9)$heteroaryl, $(C_6-C_{10})$arylamino, $(C_6-C_{10})$arylthio, $(C_6-C_{10})$ aryloxy, $(C_2-C_9)$heteroarylamino, $(C_2-C_9)$ heteroarylthio, $(C_2-C_9)$heteroaryloxy, $(C_3-C_6)$ cycloalkyl, $(C_1-C_6)$alkyl(hydroxymethylene), piperidyl, $(C_1-C_6)$alkylpiperidyl, $(C_1-C_6)$acyl, $(C_1-C_6)$acylamino, $(C_1-C_6)$acylthio, $(C_1-C_6)$acyloxy, $(C_1-C_6)$alkoxy-(C=O)—, —$CO_2H$, $(C_1-C_6)$alkyl-NH—(C=O)—, and $[(C_1-C_6)$alky$]_2$-N—(C=O)—;

wherein said $(C_1-C_6)$alkyl group may optionally be substituted by one or two groups independently selected from $(C_1-C_6)$alkylthio, $(C_1-C_6)$alkoxy, trifluoromethyl, —CN, halo, $(C_6-C_{10})$aryl, $(C_2-C_9)$ heteroaryl, $(C_6-C_{10})$arylamino, $(C_6-C_{10})$arylthio, $(C_6-C_{10})$aryloxy, $(C_2-C_9)$heteroarylamino, $(C_2-C_9)$ heteroarylthio, $(C_2-C_9)$heteroaryloxy, $(C_6-C_{10})$aryl $(C_6-C_{10})$aryl, $(C_3-C_6)$cycloalkyl, hydroxy, piperazinyl, $(C_6-C_{10})$aryl$(C_1-C_6)$alkoxy, $(C_2-C_9)$ heteroaryl$(C_1-C_6)$alkoxy, $(C_1-C_6)$acylamino, $(C_1-C_6)$ acylthio, $(C_1-C_6)$acyloxy, $(C_1-C_6)$alkylsulfinyl, $(C_6-C_{10})$arylsulfinyl, $(C_1-C_6)$alkylsulfonyl, $(C_6-C_{10})$ arylsulfonyl, amino, $(C_1-C_6)$alkylamino or $((C_1-C_6)$ alkyl$)_2$amino;

or $R^1$ and $R^2$, or $R^3$ and $R^4$, or $R^5$ and $R^6$ may be taken together to form a carbonyl;

or $R^1$ and $R^2$, or $R^3$ and $R^4$, or $R^5$ and $R^6$, or $R^7$ and $R^8$ may be taken together to form a $(C_3-C_6)$cycloalkyl, oxacyclohexyl, thiocyclohexyl, indanyl or tetralinyl ring or a group of the formula

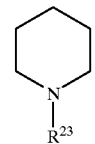

Ar is $(C_6-C_{10})$aryl$(C_1-C_6)$alkoxy$(C_6-C_{10})$aryl, $(C_6-C_{10})$ aryl$(C_1-C_6)$alkoxy$(C_2-C_9)$heteroaryl, $(C_2-C_9)$ heteroaryl$(C_1-C_6)$alkoxy$(C_6-C_{10})$aryl, $(C_2-C_9)$ heteroaryl$(C_1-C_6)$alkoxy$C_2-C_9)$heteroaryl optionally substituted by one or more substituents, preferably one to three substituents per ring, most preferably one to three substituents on the terminal ring (i.e. the ring furtherst from the point of attachment), wherein said substituents are independently selected from the group consisting of halo, —CN, $(C_1-C_6)$alkyl optionally substituted with one or more fluorine atoms (preferably one to three fluorine atoms), hydroxy, hydroxy-$(C_1-C_6)$ alkyl, $(C_1-C_6)$alkoxy optionally substituted with one or more fluorine atoms (preferably one to three fluorine atoms), $(C_1-C_6)$alkoxy$(C_1-C_6)$alkyl, HO—(C=O)—, $(C_1-C_6)$alkyl-O—(C=O)—, HO—(C=O)—$(C_1-C_6)$ alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$ alkyl, $(C_1-C_6)$alkyl(O=C)—, $(C_1-C_6)$alkyl(O=C)—$(C_1-C_6)$alkyl, $NO_2$, amino, $(C_{1-6})$alkylamino, $[(C_1-C_6)$alkyl$]_2$amino, amino$(C_1-C_6)$alkyl, $(C_1-C_6)$ alkylamino$(C_1-C_6)$alkyl, $[(C_1-C_6)$alkyl$]_2$amino $(C_1-C_6)$alkyl, $H_2N$—(C=O)—, $(C_1-C_6)$alkyl-NH—(C=O)—,$[(C_1-C_6)$alkyl$]_2N$—(C=O)—, $H_2N$ (C=O)—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$ alkyl, H(O=C)—NH—, $(C_1-C_6)$alkyl(C=O)—NH—, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$ alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkyl-HN—$SO_2$—$(C_1-C_6)$alkyl, $[(C_1C_6)$alkyl$]_2N$—$SO_2$—$(C_1-C_6)$alkyl, $CF_3SO_3$—, $(C_1-C_6)$alkyl-$SO_3$—phenyl, phenyl$(C_1-C_6)$alkyl, $(C_3-C_{10})$cycloalkyl, $(C_2-C_9)$ heterocycloalkyl, and $(C_2-C_9)$heteroaryl;

with the proviso that at least one of $R^1$–$R^8$ is hydroxy;

with the additional proviso that the compounds of formula I can not be (2R,4S)-1-[4-(4-Fluorobenzyloxy)-benzenesulfonyl]-4-hydroxy-piperidine-2-carboxylic acid hydroxyamide; (2R,3S)-1-[4-(2-Chloro-thiazol-5- ylmethoxy)-benzenesulfonyl]-3-hydroxy-piperidine-2-carboxylic acid hydroxyamide; (2R,3S)-3-Hydroxy-1-[4-(thiazol-5-ylmethoxy)-benzenesulfonyl]-piperidine-2-carboxylic acid hydroxyamide; (2R,3S)-3-Hydroxy-1-[4-(pyridin4-ylmethoxy)-benzenesulfonyl]-piperidine-2-carboxylic acid hydroxyamide; (2R,3S)-1-[4-(4-Fluorobenzyloxy)-benzenesulfonyl]-3-hydroxy-piperidine-2-carboxylic acid hydroxyamide; (2R,3S)-1-{4-[2-(4-Fluorophenyl)-ethoxy]-benzenesulfonyl}-3-hydroxy-piperidine-2-carboxylic acid hydroxyamide; (2R,3S)-3-Hydroxy-1-[4-(2-pyridin-4-yl-ethoxy)-benzenesulfonyl]-piperidine-2-carboxylic acid hydroxyamide; (2R,3S)-1-[4-(Benzothiazol-2-ylmethoxy)-benzenesulfonyl]-3-hydroxy-piperidine-2-carboxylic acid hydroxyamide; (2R,3S)-3-Hydroxy-1-[4-(5-trifluoromethyl-benzothiazol-2-ylmethoxy)-benzenesulfonyl]-piperidine-2-carboxylic acid hydroxyamide; (2R,3S)-3-Hydroxy-1-[4-(1H-tetrazol-5-ylmethoxy)-benzenesulfonyl]-piperidine-2-carboxylic acid hydroxyamide; (2R,3S)-1-[4-(2-Chloro-thiazol-5-ylmethoxy)-benzenesulfonyl]-3-hydroxy-3-methyl-piperidine-2-carboxylic acid hydroxyamide; (2R,3S)-3-Hydroxy-3-methyl-1-[4-(thiazol-5-ylmethoxy)-benzenesulfonyl]-piperidine-2-carboxylic acid hydroxyamide; (2R,3S)-3-Hydroxy-3-methyl-1-[4-(pyridin-4-ylmethoxy)-benzenesulfonyl]-piperidine-2-carboxylic acid hydroxyamide; (2R,3S)-1-[4-(4-Fluorobenzyloxy)-benzenesulfonyl]-3-hydroxy-3-methyl-piperidine-2-carboxylic acid hydroxyamide; (2R,3S)-1-{4-[2-(4-Fluorophenyl)-ethoxy]-benzenesulfonyl}-3-hydroxy-3-methyl-piperidine-2-carboxylic acid hydroxyamide; (2R,3S)-3-Hydroxy-3-methyl-1-[4-(2-pyridin-4-yl ethoxy)-benzenesulfonyl]-piperidine-2-carboxylic acid hydroxyamide; (2R,3S)-1-[4-(Benzothiazol-2-ylmethoxy)-benzenesulfonyl]-3-hydroxy-3-methyl-piperidine-2-carboxylic acid hydroxyamide; (2R,3S)-3-Hydroxy-3-methyl-1-[4-(5-trifluoromethyl-benzothiazol-2-ylmethoxy)-benzenesulfonyl]-piperidine-2-carboxylic acid hydroxyamide; (2R,3S)-3-Hydroxy-3-methyl-1-[4-(1H-tetrazol-5-ylmethoxy)-benzenesulfonyl]-piperidine-2-carboxylic acid hydroxyamide; (2R,4S)-1-(4-Benzyloxy-benzenesulfonyl)-4-butylaminomethyl-4-hydroxy-piperidine-2-carboxylic acid hydroxyamide; (2R,4S)-4-Butylaminomethyl-1-[4-(4-fluorobenzyloxy)-benzenesulfonyl]-4-hydroxy-piperidine-2-carboxylic acid hydroxyamide; (2R,4R)-1-(4-Benzyloxy-benzenesulfonyl)-4-hydroxy-piperidine-2-carboxylic acid hydroxyamide; (2R,4R)-1-[4-(4-Fluorobenzyloxy)-benzenesulfonyl]-4-hydroxy-piperidine-2-carboxylic acid hydroxyamide; (2R,5S)-1-[4-(4-Fluorobenzyloxy)-benzenesulfonyl]-5-hydroxy-piperidine-2-carboxylic acid hydroxyamide; (2R,5S)-1-(4-Benzyloxy-benzenesulfonyl)-5-hydroxy-piperidine-2-carboxylic acid hydroxyamide; (2R,5R)-1-(4-Benzyloxy-benzenesulfonyl)-5-hydroxy-piperidine-2-carboxylic acid hydroxyamide; (2R,5R)-1-[4-(4-Fluorobenzyloxy)-benzenesulfonyl]-5-hydroxy-piperidine-2-carboxylic acid hydroxyamide; (2R,3S)-1-(4-Benzyloxy-benzenesulfonyl)-3-hydroxy-piperidine-2-carboxylic acid hydroxyamide; (2R,4S)-1-(4-Benzyloxy-benzenesulfonyl)-4-hydroxy-piperidine-2-carboxylic acid hydroxyamide; and (2R,4S)-1-[4-(4-Fluorobenzyloxy)-benzenesulfonyl]-4-hydroxy-piperidine-2-carboxylic acid hydroxyamide.

The present invention also relates to a compound of the formula

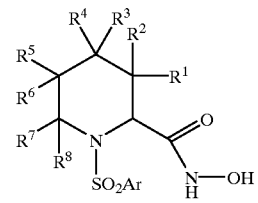

I or the pharmaceutically acceptable salts thereof, wherein $R^1$–$R^8$ are selected from the group consisting of hydroxy, hydrogen, halogen (preferably chloro or fluoro), —CN, $(C_1–C_6)$alkyl, $(C_2–C_6)$alkenyl, $(C_6–C_{10})$aryl$(C_2–C_6)$alkenyl, $(C_2–C_9)$heteroaryl $(C_2–C_6)$alkenyl, $(C_2–C_6)$alkynyl, $(C_6–C_{10})$aryl$(C_2–C_6)$alkynyl, $(C_2–C_9)$heteroaryl$(C_2–C_6)$alkynyl, $(C_1–C_6)$alkylamino, $(C_1–C_6)$alkylthio, $(C_1–C_6)$alkoxy, perfluoro$(C_1–C_6)$alkyl, $(C_6–C_{10})$aryl, $(C_2–C_9)$heteroaryl, $(C_6–C_{10})$arylamino, $(C_6–C_{10})$arylthio, $(C_6–C_{10})$aryloxy, $(C_2–C_9)$heteroarylamino, $(C_2–C_9)$heteroarylthio, $(C_2–C_9)$heteroaryloxy, $(C_3–C_6)$cycloalkyl, $(C_1–C_6)$alkyl(hydroxymethylene), piperidyl, $(C_1–C_6)$alkylpiperidyl, $(C_1–C_6)$acylamino, $(C_1–C_6)$acylthio, $(C_1–C_6)$acyloxy, $(C_1–C_6)$alkoxy-(C=O)—, —$CO_2H$, $(C_1–C_6)$alkyl-NH—(C=O)—, and $[(C_1–C_6)$alky$]_2$-N—(C=O)—;

wherein said $(C_1–C_6)$alkyl group may optionally be substituted by one or two groups independently selected from $(C_1–C_6)$alkylthio, $(C_1–C_6)$alkoxy, trifluoromethyl, —CN, halo, $(C_6–C_{10})$aryl, $(C_2–C_9)$heteroaryl, $(C_6–C_{10})$arylamino, $(C_6–C_{10})$arylthio, $(C_6–C_{10})$aryloxy, $(C_2–C_9)$heteroarylamino, $(C_2–C_9)$heteroarylthio, $(C_2–C_9)$heteroaryloxy, $(C_6–C_{10})$aryl $(C_6–C_{10})$aryl, $(C_3–C_6)$cycloalkyl, hydroxy, piperazinyl, $(C_6–C_{10})$aryl$(C_1–C_6)$alkoxy, $(C_2–C_9)$heteroaryl$(C_1–C_6)$alkoxy, $(C_1–C_6)$acylamino, $(C_1–C_6)$acylthio, $(C_1–C_6)$acyloxy, $(C_1–C_6)$alkylsulfinyl, $(C_6–C_{10})$arylsulfinyl, $(C_1–C_6)$alkylsulfonyl, $(C_6–C_{10})$arylsulfonyl, amino, $(C_1–C_6)$alkylamino or $((C_1–C_6)$alkyl$)_2$amino;

or $R^1$ and $R^2$, or $R^3$ and $R^4$, or $R^5$ and $R^6$ may be taken together to form a carbonyl;

or $R^1$ and $R^2$, or $R^3$ and $R^4$, or $R^5$ and $R^6$, or $R^7$ and $R^8$ may be taken together to form a $(C_3–C_6)$cycloalkyl, oxacyclohexyl, thiocyclohexyl, indanyl or tetralinyl ring or a group of the formula

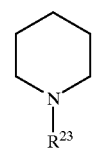

Ar is $(C_6–C_{10})$aryl$(C_1–C_6)$alkoxy$(C_6–C_{10})$aryl, $(C_6–C_{10})$aryl$(C_1–C_6)$alkoxy$(C_2–C_9)$heteroaryl, $(C_2–C_9)$heteroaryl$(C_1–C_6)$alkoxy$(C_6–C_{10})$aryl, $(C_2–C_9)$heteroaryl$(C_1–C_6)$alkoxy$C_2–C_9)$heteroaryl optionally substituted by one or more substituents, preferably one to three substituents per ring, most preferably one to three substituents on the terminal ring (i.e. the ring furtherst from the point of attachment), wherein said substituents are independently selected from the group consisting of halo, —CN, $(C_1–C_6)$alkyl optionally substituted with one or more fluorine atoms (preferably one to three fluorine atoms), hydroxy, hydroxy-($C_1$–$C_6$)alkyl, ($C_1$–$C_6$)alkoxy optionally substituted with one or more fluorine atoms (preferably one to three fluorine atoms), ($C_1$–$C_6$)alkoxy($C_1$–$C_6$)alkyl, HO—(C=O)—, ($C_1$–$C_6$)alkyl-O—(C=O)—, HO—(C=O)—($C_1$–$C_6$)alkyl, ($C_1$–$C_6$)alkyl-O—(C=O)—($C_1$–$C_6$)alkyl, ($C_1$–$C_6$)alkyl-(C=O)—O—, ($C_1$–$C_6$)alkyl-(C=O)—O—($C_1$–$C_6$)alkyl, H(O=C)—, H(O=C)—($C_1$–$C_6$)alkyl, ($C_1$–$C_6$)alkyl(O=C)—, ($C_1$–$C_6$)alkyl(O=C)—($C_1$–$C_6$)alkyl, $NO_2$, amino, ($C_1$–$C_6$)alkylamino, [($C_1$–$C_6$)alkyl]$_2$amino, amino($C_1$–$C_6$)alkyl, ($C_1$–$C_6$)alkylamino($C_1$–$C_6$)alkyl, [($C_1$–$C_6$)alkyl]$_2$amino($C_1$–$C_6$)alkyl, $H_2N$—(C=O)—, ($C_1$–$C_6$)alkyl-NH—(C=O)—, [($C_1$–$C_6$)alkyl]$_2$N—(C=O)—, $H_2N$(C=O)—($C_1$–$C_6$)alkyl, ($C_1$–$C_6$)alkyl-HN(C=O)—($C_1$–$C_6$)alkyl, [($C_1$–$C_6$)alkyl]$_2$N—(C=O)—($C_1$–$C_6$)alkyl, H(O=C)—NH—, ($C_1$–$C_6$)alkyl(C=O)—NH—, ($C_1$–$C_6$)alkyl(C=O)—[NH]($C_1$–$C_6$)alkyl, ($C_1$–$C_6$)alkyl(C=O)—[N($C_1$–$C_6$)alkyl]($C_1$–$C_6$)alkyl, ($C_1$–$C_6$)alkyl-S—, ($C_1$–$C_6$)alkyl-(S=O)—, ($C_1$–$C_6$)alkyl-$SO_2$—, ($C_1$–$C_6$)alkyl-$SO_2$—NH—, $H_2N$—$SO_2$—, $H_2N$—$SO_2$—($C_1$–$C_6$)alkyl, ($C_1$–$C_6$)alkylHN—$SO_2$—($C_1$–$C_6$)alkyl, [($C_1$–$C_6$)alkyl]$_2$N—$SO_2$—($C_1$–$C_6$)alkyl, $CF_3SO_3$—, ($C_1$–$C_6$)alkyl-$SO_3$-, phenyl, phenyl($C_1$–$C_6$)alkyl, ($C_3$–$C_{10}$)cycloalkyl, ($C_2$–$C_9$)heterocycloalkyl, and ($C_2$–$C_9$)heteroaryl;

with the proviso that at least one of $R^1$–$R^8$ is hydroxy;

with the additional proviso that the compounds of formula I can not be (2R,4S)-1-[4-(4-Fluorobenzyloxy)-benzenesulfonyl]-4-hydroxy-piperidine-2-carboxylic acid hydroxyamide; (2R,3S)-1-[4-(2-Chloro-thiazol-5-ylmethoxy)-benzenesulfonyl]-3-hydroxy-piperidine-2-carboxylic acid hydroxyamide; (2R,3S)-3-Hydroxy-1-[4-(thiazol-5-ylmethoxy)-benzenesulfonyl]-piperidine-2-carboxylic acid hydroxyamide; (2R,3S)-3-Hydroxy-1-[4-(pyridin-4-ylmethoxy)-benzenesulfonyl]-piperidine-2-carboxylic acid hydroxyamide; (2R,3S)-1-[4-(4-Fluorobenzyloxy)-benzenesulfonyl]-3-hydroxy-piperidine-2-carboxylic acid hydroxyamide; (2R,3S)-1-{-4-[2-(4Fluorophenyl)-ethoxy]-benzenesulfonyl}-3-hydroxy-piperidine-2-carboxylic acid hydroxyamide; (2R,3S)-3-Hydroxy-1-[4-(2-pyridin-4-yl-ethoxy)-benzenesulfonyl]-piperidine-2-carboxylic acid hydroxyamide; (2R,3S)-1-[4-(Benzothiazol-2-ylmethoxy)-benzenesulfonyl]-3-hydroxy-piperidine-2-carboxylic acid hydroxyamide; (2R,3S)-3-Hydroxy-1-[4-(5-trifluoromethyl-benzothiazol-2-ylmethoxy)-benzenesulfonyl]-piperidine-2-carboxylic acid hydroxyamide; (2R,3S)-3-Hydroxy-1-[4-(1H-tetrazol-5-ylmethoxy)-benzenesulfonyl]-piperidine-2-carboxylic acid hydroxyamide; (2R,3S)-1-[4-(2-Chloro-thiazol-5-ylmethoxy)-benzenesulfonyl]-3-hydroxy-3-methyl-piperidine-2-carboxylic acid hydroxyamide; (2R,3S)-3-Hydroxy-3-methyl-1-[4-(thiazol-5-ylmethoxy)-benzenesulfonyl]-piperidine-2-carboxylic acid hydroxyamide; (2R,3S)-3-Hydroxy-3-methyl-1-[4-(pyridin-4-ylmethoxy)-benzenesulfonyl]-piperidine-2-carboxylic acid hydroxyamide; (2R,3S)-1-[4-(4-Fluorobenzyloxy)-benzenesulfonyl]-3-hydroxy-3-methyl-piperidine-2-carboxylic acid hydroxyamide; (2R,3S)-1-{4-[2-(4-Fluorophenyl)-ethoxy]-benzenesulfonyl}-3-hydroxy-3methyl-piperidine-2-carboxylic acid hydroxyamide; (2R,3S)-3-Hydroxy-3-methyl-1-[4-(2-pyridin-4-yl-ethoxy)-benzenesulfonyl]-piperidine-2-carboxylic acid hydroxyamide; (2R,3S)-1-[4-(Benzothiazol-2-ylmethoxy)-benzenesulfonyl]-3-hydroxy-3-methyl-piperidine-2-carboxylic acid hydroxyamide; (2R,3S)-3-Hydroxy-3-methyl-1-[4-(5-trifluoromethyl-benzothiazol-2-ylmethoxy)-benzenesulfonyl]-piperidine-2-carboxylic acid hydroxyamide; (2R,3S)-3-Hydroxy-3-methyl-1-[4-(1H-tetrazol-5-ylmethoxy)-benzenesulfonyl]-piperidine-2-carboxylic acid hydroxyamide; (2R,4S)-1-(4-Benzyloxy-benzenesulfonyl)-4-butylaminomethyl-4-hydroxy-piperidine-2-carboxylic acid hydroxyamide; (2R,4S)-4-Butylaminomethyl-1-[4-(4-fluorobenzyloxy)-benzenesulfonyl]-4-hydroxy-piperidine-2-carboxylic acid hydroxyamide; (2R,4R)-1-(4-Benzyloxy-benzenesulfonyl)-4-hydroxy-piperidine-2-carboxylic acid hydroxyamide; (2R,4R)-1-[4-(4-Fluorobenzyloxy)-benzenesulfonyl]-4-hydroxy-piperidine-2-carboxylic acid hydroxyamide; (2R,5S)-1-[4-(4-Fluorobenzyloxy)-benzenesulfonyl]-5-hydroxy-piperidine-2-carboxylic acid hydroxyamide; (2R,5S)-1-(4-Benzyloxy-benzenesulfonyl)-5-hydroxy-piperidine-2-carboxylic acid hydroxyamide; (2R,5R)-1-(4-Benzyloxy-benzenesulfonyl)-5-hydroxy-piperidine-2-carboxylic acid hydroxyamide; (2R,5R)-1-[4-(4-Fluorobenzyloxy)-benzenesulfonyl]-5-hydroxy-piperidine-2-carboxylic acid hydroxyamide; (2R,3S)-1-(4-Benzyloxy-benzenesulfonyl)-3-hydroxy-piperidine-2-carboxylic acid hydroxyamide; (2R,4S)-1-(4-Benzyloxy-benzenesulfonyl)-4-hydroxy-piperidine-2-carboxylic acid hydroxyamide; and (2R,4S)-1-[4-(4-Fluorobenzyloxy)-benzenesulfonyl]-4-hydroxy-piperidine-2-carboxylic acid hydroxyamide.

Preferred compounds of the present invention are those wherein at least one of $R^1$–$R^6$ is hydroxy.

Other preferred compounds of the present invention are those wherein at least one of $R^1$–$R^6$ is hydroxy and each of the other of $R^1$–$R^8$ is hydrogen.

Other preferred compounds of the present invention are those wherein at least one of $R^1$–$R^6$ is hydroxy and at least one of the other of $R^1$–$R^8$ is optionally substituted ($C_1$–$C_6$)alkyl.

Other preferred compounds of the present invention are those wherein at least one of $R^1$–$R^6$ is hydroxy and each of $R^7$–$R^8$ is hydrogen.

Other preferred compounds of the present invention are those wherein at least one of $R^1$–$R^6$ is hydroxy and each of $R^7$–$R^8$ is optionally substituted ($C_1$–$C_6$)alkyl.

Other preferred compounds of the present invention are those wherein $R^1$ is hydroxy.

Other preferred compounds of the present invention are those wherein $R^1$ is hydroxy and each of the other of $R^2$–$R^8$ is hydrogen.

Other preferred compounds of the present invention are those wherein $R^1$ is hydroxy and at least one of the other of $R^2$–$R^8$ is optionally substituted ($C_1$–$C_6$)alkyl.

Other preferred compounds of the present invention are those wherein $R^1$ is hydroxy and each of $R^7$–$R^8$ is hydrogen.

Other preferred compounds of the present invention are those wherein $R^1$ is hydroxy and each of $R^7$–$R^8$ is optionally substituted ($C_1$–$C_6$)alkyl.

Other preferred compounds of the present invention are those wherein $R^1$ is hydroxy and $R^2$ is ($C_1$–$C_6$)alkyl.

Other preferred compounds of the present invention are those wherein $R^1$ is hydroxy and $R^2$ is ($C_1$–$C_6$)alkyl and each of the other of $R^3$–$R^8$ is hydrogen.

Other preferred compounds of the present invention are those wherein $R^1$ is hydroxy and $R^2$ is ($C_1$–$C_6$)alkyl and at least one of the other of $R^3$–$R^8$ is optionally substituted ($C_1$–$C_6$)alkyl.

Other preferred compounds of the present invention are those wherein $R^1$ is hydroxy and $R^2$ is $(C_1-C_6)$alkyl and each of $R^7-R^8$ is hydrogen.

Other preferred compounds of the present invention are those wherein $R^1$ is hydroxy and $R^2$ is $(C_1-C_6)$alkyl and each of $R^7-R^8$ is optionally substituted $(C_1-C_6)$alkyl.

Other preferred compounds of the present invention are those wherein $R^1$ is hydroxy and $R^2$ is methyl.

Other preferred compounds of the present invention are those wherein $R^1$ is hydroxy and $R^2$ is methyl and each of the other of $R^3-R^8$ is hydrogen.

Other preferred compounds of the present invention are those wherein $R^1$ is hydroxy and $R^2$ is methyl and at least one of the other of $R^3-R^8$ is optionally substituted $(C_1-C_6)$alkyl.

Other preferred compounds of the present invention are those wherein $R^1$ is hydroxy and $R^2$ is methyl and each of $R^7-R^8$ is hydrogen.

Other preferred compounds of the present invention are those wherein $R^1$ is hydroxy and $R^2$ is methyl and each of $R^7-R^8$ is optionally substituted $(C_1-C_6)$alkyl.

Other preferred compounds of the present invention are those wherein $R^2$ is hydroxy.

Other preferred compounds of the present invention are those wherein $R^2$ is hydroxy and each of the other of $R^1$ and $R^3-R^8$ is hydrogen.

Other preferred compounds of the present invention are those wherein $R^2$ is hydroxy and at least one of the other of $R^1$ and $R^3-R^8$ is optionally substituted $(C_1-C_6)$alkyl.

Other preferred compounds of the present invention are those wherein $R^2$ is hydroxy and each of $R^7-R^8$ is hydrogen.

Other preferred compounds of the present invention are those wherein $R^2$ is hydroxy and each of $R^7-R^8$ is optionally substituted $(C_1-C_6)$alkyl.

Other preferred compounds of the present invention are those wherein $R^3$ is hydroxy.

Other preferred compounds of the present invention are those wherein $R^3$ is hydroxy and each of the other of $R^1-R^2$ and $R^4-R^8$ is hydrogen.

Other preferred compounds of the present invention are those wherein $R^3$ is hydroxy and at least one of the other of $R^1-R^2$ and $R^4-R^8$ is optionally substituted $(C_1-C_6)$alkyl.

Other preferred compounds of the present invention are those wherein $R^3$ is hydroxy and each of $R^7-R^8$ is hydrogen.

Other preferred compounds of the present invention are those wherein $R^3$ is hydroxy and each of $R^7-R^8$ is optionally substituted $(C_1-C_6)$alkyl.

Other preferred compounds of the present invention are those wherein $R^4$ is hydroxy.

Other preferred compounds of the present invention are those wherein $R^4$ is hydroxy and each of the other of $R^1-R^3$ and $R^4-R^8$ is hydrogen.

Other preferred compounds of the present invention are those wherein $R^4$ is hydroxy and at least one of the other of $R^1-R^3$ and and $R^4-R^8$ is optionally substituted $(C_1-C_6)$alkyl.

Other preferred compounds of the present invention are those wherein $R^4$ is hydroxy and each of $R^7-R^8$ is hydrogen.

Other preferred compounds of the present invention are those wherein $R^4$ is hydroxy and each of $R^7-R^8$ is optionally substituted $(C_1-C_6)$alkyl.

Other preferred compounds of the present invention are those wherein $R^5$ is hydroxy.

Other preferred compounds of the present invention are those wherein $R^5$ is hydroxy and each of the other of $R^1-R^4$ and $R^6-R^8$ is hydrogen.

Other preferred compounds of the present invention are those wherein $R^5$ is hydroxy and at least one of the other of $R^1-R^4$ and $R^6-R^8$ is optionally substituted $(C_1-C_6)$alkyl.

Other preferred compounds of the present invention are those wherein $R^5$ is hydroxy and each of $R^7-R^8$ is hydrogen.

Other preferred compounds of the present invention are those wherein $R^5$ is hydroxy and each of $R^7-R^8$ is optionally substituted $(C_1-C_6)$alkyl.

Other preferred compounds of the present invention are those wherein $R^6$ is hydroxy.

Other preferred compounds of the present invention are those wherein $R^6$ is hydroxy and each of the other of $R^1-R^5$ and $R^7-R^8$ is hydrogen.

Other preferred compounds of the present invention are those wherein $R^6$ is hydroxy and at least one of the other of $R^1-R^5$ and $R^7-R^8$ is optionally substituted $(C_1-C_6)$alkyl.

Other preferred compounds of the present invention are those wherein $R^6$ is hydroxy and each of $R^7-R^8$ is hydrogen.

Other preferred compounds of the present invention are those wherein $R^6$ is hydroxy and each of $R^7-R^8$ is optionally substituted $(C_1-C_6)$alkyl.

Other preferred compounds of the present invention are those wherein Ar is $(C_6-C_{10})$aryl$(C_1-C_6)$alkoxy$(C_6-C_{10})$aryl, $(C_6-C_{10})$aryl$(C_1-C_6)$alkoxy$(C_2-C_9)$heteroaryl, $(C_2-C_9)$heteroaryl$(C_1-C_6)$alkoxy$(C_6-C_{10})$aryl or $(C_2-C_9)$heteroaryl$(C_1-C_6)$alkoxy$(C_2-C_9)$heteroaryl optionally substituted by one or more, preferably one to three substituents per ring, most preferably one to three substituents on the terminal ring (i.e. the ring furthest from the point of attachment), wherein said substituents are independently selected from halo, $(C_1-C_6)$alkyl, $(C_1-C_6)$alkoxy or perfluoro$(C_1-C_3)$alkyl.

Other more preferred compounds of the invention are those wherein Ar is $(C_6-C_{10})$arylmethoxy$(C_6-C_{10})$aryl, $(C_6-C_{10})$arylmethoxy$(C_2-C_9)$heteroaryl, $(C_2-C_9)$heteroarylmethoxy$(C_6-C_{10})$aryl or $(C_2-C_9)$heteroarylmethoxy$(C_2-C_9)$heteroaryl optionally substituted by one or more, preferably one to three substituents per ring, most preferably one to three substituents on the terminal ring wherein said substuituents are independently selected from the group consisting of halo, $(C_1-C_6)$alkyl, $(C_1-C_6)$alkoxy or perfluoro$(C_1-C_3)$alkyl.

More preferred compounds of the invention are those wherein Ar is optionally substituted $(C_6-C_{10})$arylmethoxyphenyl, $(C_6-C_{10})$arylmethoxypyridyl, $(C_6-C_{10})$arylmethoxyfuryl, $(C_6-C_{10})$arylmethoxypyrroyl, $(C_6-C_{10})$arylmethoxythienyl, $(C_6-C_{10})$arylmethoxyisothiazolyl, $(C_6-C_{10})$arylmethoxyimidazolyl, $(C_6-C_{10})$arylmethoxybenzimidazolyl, $(C_6-C_{10})$arylmethoxytetrazolyl, $(C_6-C_{10})$arylmethoxypyrazinyl, $(C_6-C_{10})$arylmethoxypyrimidyl, $(C_6-C_{10})$arylmethoxyquinolyl, $(C_6-C_{10})$arylmethoxyisoquinolyl, $(C_6-C_{10})$arylmethoxybenzofuryl, $(C_6-C_{10})$arylmethoxyisobenzofuryl, $(C_6-C_{10})$arylmethoxybenzothienyl, $(C_6-C_{10})$arylmethoxypyrazolyl, $(C_6-C_{10})$arylmethoxyindolyl, $(C_6-C_{10})$arylmethoxyisoindolyl, $(C_6-C_{10})$arylmethoxypurinyl, $(C_6-C_{10})$arylmethoxycarbazolyl, $(C_6-C_{10})$arylmethoxyisoxazolyl, $(C_6-C_{10})$arylmethoxythiazolyl, $(C_6-C_{10})$arylmethoxyoxazolyl, $(C_6-C_{10})$arylmethoxybenzthiazolyl, $(C_6-C_{10})$arylmethoxybenzoxazolyl, pyridylmethoxyphenyl, furylmethoxyphenyl, pyrroylmethoxyphenyl, thienylmethoxyphenyl, isothiazolylmethoxyphenyl, imidazolylmethoxyphenyl, benzimidazolylmethoxyphenyl, tetrazolylmethoxyphenyl, pyrazinylmethoxyphenyl, pyrimidylmethoxyphenyl, quinolylmethoxyphenyl, isoquinolylmethoxyphenyl, benzofurylmethoxyphenyl, isobenzofurylmethoxyphenyl,
benzothienylmethoxyphenyl,
pyrazolylmethoxyphenyl, indolylmethoxyphenyl,
isoindolyl methoxyphenyl, purinylmethoxyphenyl,
carbazolylmethoxyphenyl, isoxazolylmethoxyphenyl,
thiazolylmethoxyphenyl, oxazolylmethoxyphenyl,
benzthiazolylmethoxyphenyl,
benzoxazolylmethoxyphenyl, pyridylmethoxypyridyl, pyridylmethoxyfuryl,
pyridylmethoxypyrroyl, pyridylmethoxythienyl,
pyridylmethoxyisothiazolyl,
pyridylmethoxyimidazolyl,
pyridylmethoxybenzimidazolyl, pyridyl methoxytetrazolyl, pyridylmethoxypyrazinyl,
pyridylmethoxypyrimidyl, pyridyl methoxyquinolyl,
pyridylmethoxyisoquinolyl,
pyridylmethoxybenzofuryl,
pyridylmethoxyisobenzofuryl,
pyridylmethoxybenzothienyl,
pyridylmethoxypyrazolyl, pyridylmethoxyindolyl,
pyridylmethoxyisoindolyl, pyridylmethoxypurinyl,
pyridylmethoxycarbazolyl, pyridylmethoxyisoxazolyl,
pyridylmethoxythiazolyl, pyridylmethoxyoxazolyl,
pyridylmethoxybenzthiazolyl,
pyridylmethoxybenzoxazolyl, furylmethoxypyridyl, furylmethoxyfuryl,
furylmethoxypyrroyl, furylmethoxythienyl,
furylmethoxyisothiazolyl, furylmethoxyimidazolyl,
furylmethoxybenzimidazolyl, furylmethoxytetrazolyl,
furylmethoxypyrazinyl, furylmethoxypyrimidyl,
furylmethoxyquinolyl, furylmethoxyisoquinolyl,
furylmethoxybenzofuryl, furylmethoxyisobenzofuryl,
furylmethoxybenzothienyl, furylmethoxypyrazolyl,
furylmethoxyindolyl, furylmethoxyisoindolyl,
furylmethoxypurinyl, furylmethoxycarbazolyl,
furylmethoxyisoxazolyl, furylmethoxythiazolyl,
furylmethoxyoxazolyl, furylmethoxybenzthiazolyl,
furylmethoxybenzoxazolyl, pyrroylmethoxypyridyl, pyrroylmethoxyfuryl,
pyrroylmethoxypyroyl, pyrroylmethoxythienyl,
pyrroylmethoxyisothiazolyl,
pyrroylmethoxyimidazolyl,
pyrroylmethoxybenzimidazolyl,
pyrroylmethoxytetrazolyl, pyrroylmethoxypyrazinyl,
pyrroylmethoxypyrimidyl, pyrroylmethoxyquinolyl,
pyrroylmethoxyisoquinolyl,
pyrroylmethoxybenzofuryl,
pyrroylmethoxyisobenzofuryl,
pyrroylmethoxybenzothienyl,
pyrroylmethoxypyrazolyl, pyrroylmethoxyindolyl,
pyrroylmethoxyisoindolyl, pyrroylmethoxypurinyl,
pyrroylmethoxycarbazolyl, pyrroylmethoxyisoxazolyl,
pyrroylmethoxythiazolyl, pyrroylmethoxyoxazolyl,
pyrroylmethoxybenzthiazolyl,
pyrroylmethoxybenzoxazolyl, thienylmethoxypyridyl, thienylmethoxyfuryl,
thienylmethoxypyrroyl, thienylmethoxythienyl,
thienylmethoxyisothiazolyl,
thienylmethoxyimidazolyl,
thienylmethoxybenzimidazolyl,
thienylmethoxytetrazolyl, thienylmethoxypyrazinyl,
thienylmethoxypyrimidyl, thienylmethoxyquinolyl,
thienylmethoxyisoquinolyl,
thienylmethoxybenzofuryl,
thienylmethoxyisobenzofuryl,
thienylmethoxybenzothienyl,
thienylmethoxypyrazolyl, thienylmethoxyindolyl,
thienylmethoxyisoindolyl, thienylmethoxypurinyl,
thienylmethoxycarbazolyl, thienylmethoxyisoxazolyl,
thienylmethoxythiazolyl, thienylmethoxyoxazolyl,
thienylmethoxybenzthiazolyl,
thienylmethoxybenzoxazolyl, pyrazinylmethoxypyridyl, pyrazinylmethoxyfuryl,
pyrazinylmethoxypyrroyl, pyrazinylmethoxythienyl,
pyrazinylmethoxyisothiazolyl,
pyrazinylmethoxyimidazolyl,
pyrazinylmethoxybenzimidazolyl,
pyrazinylmethoxytetrazolyl,
pyrazinylmethoxypyrazinyl,
pyrazinylmethoxypyrimidyl,
pyrazinylmethoxyquinolyl,
pyrazinylmethoxyisoquinolyl,
pyrazinylmethoxybenzofuryl,
pyrazinylmethoxyisobenzofuryl,
pyrazinylmethoxybenzothienyl,
pyrazinylmethoxypyrazolyl, pyrazinylmethoxyindolyl,
pyrazinylmethoxyisoindolyl,
pyrazinylmethoxypurinyl,
pyrazinylmethoxycarbazolyl,
pyrazinylmethoxyisoxazolyl,
pyrazinylmethoxythiazolyl,
pyrazinylmethoxyoxazolyl,
pyrazinylmethoxybenzthiazolyl,
pyrazinylmethoxybenzoxazolyl, pyrimidylmethoxypyridyl, pyrimidylmethoxyfuryl,
pyrimidylmethoxypyrroyl, pyrimidylmethoxythienyl,
pyrimidylmethoxyisothiazolyl,
pyrimidylmethoxyimidazolyl,
pyrimidylmethoxybenzimidazolyl,
pyrimidylmethoxytetrazolyl,
pyrimidylmethoxypyrazinyl,
pyrimidylmethoxypyrimidyl,
pyrimidylmethoxyquinolyl,
pyrimidylmethoxyisoquinolyl,
pyrimidylmethoxybenzofuryl,
pyrimidylmethoxyisobenzofuryl,
pyrimidylmethoxybenzothienyl,
pyrimidylmethoxypyrazolyl,
pyrimidylmethoxyindolyl,
pyrimidylmethoxyisoindolyl,
pyrimidylmethoxypurinyl,
pyrimidylmethoxycarbazolyl,
pyrimidylmethoxyisoxazolyl,
pyrimidylmethoxythiazolyl,
pyrimidylmethoxyoxazolyl,
pyrimidylmethoxybenzthiazolyl,
pyrimidylmethoxybenzoxazolyl, thiazolylmethoxypyridyl, thiazolylmethoxyfuryl,
thiazolylmethoxypyrroyl, thiazolylmethoxythienyl,
thiazolylmethoxyisothiazolyl,
thiazolylmethoxyimidazolyl,
thiazolylmethoxybenzimidazolyl,
thiazolylmethoxytetrazolyl,
thiazolylmethoxypyrazinyl,
thiazolylmethoxypyrimidyl, thiazolylmethoxyquinolyl,
thiazolylmethoxyisoquinolyl,
thiazolylmethoxybenzofuryl,
thiazolylmethoxyisobenzofuryl,
thiazolylmethoxybenzothienyl,
thiazolylmethoxypyrazolyl, thiazolylmethoxyindolyl,
thiazolylmethoxyisoindolyl, thiazolylmethoxypurinyl,
thiazolylmethoxycarbazolyl,
thiazolylmethoxyisoxazolyl,
thiazolylmethoxythiazolyl, thiazolylmethoxyoxazolyl, thiazolylmethoxybenzthiazolyl,
thiazolylmethoxybenzoxazolyl, and
oxazolylmethoxypyridyl, oxazolylmethoxyfuryl, oxazolylmethoxypyrroyl, oxazolylmethoxythienyl, oxazolylmethoxyisothiazolyl, oxazolylmethoxyimidazolyl, oxazolylmethoxybenzimidazolyl, oxazolylmethoxytetrazolyl, oxazolylmethoxypyrazinyl, oxazolylmethoxypyrimidyl, oxazolylmethoxyquinolyl, oxazolylmethoxyisoquinolyl, oxazolylmethoxybenzofuryl, oxazolylmethoxyisobenzofuryl, oxazolylmethoxybenzothienyl, oxazolylmethoxypyrazolyl, oxazolylmethoxyindolyl, oxazolylmethoxyisoindolyl, oxazolylmethoxypurinyl, oxazolylmethoxycarbazolyl, oxazolylmethoxyisoxazolyl, oxazolylmethoxythiazolyl, oxazolylmethoxyoxazolyl, oxazolylmethoxybenzthiazolyl, oxazolylmethoxybenzoxazolyl.

More preferred compounds of the invention are those wherein Ar is optionally substituted $(C_6-C_{10})$arylmethoxyoxyphenyl, $(C_6-C_{10})$arylmethoxypyridyl, $(C_6-C_{10})$arylmethoxyfuryl, $(C_6-C_{10})$arylmethoxypyrroyl, $(C_6-C_{10})$arylmethoxythienyl, $(C_6-C_{10})$arylmethoxyisothiazolyl, $(C_6-C_{10})$arylmethoxyimidazolyl, $(C_6-C_{10})$arylmethoxybenzimidazolyl, $(C_6-C_{10})$arylmethoxytetrazolyl, $(C_6-C_{10})$arylmethoxypyrazinyl, $(C_6-C_{10})$arylmethoxypyrimidyl, $(C_6-C_{10})$arylmethoxyquinolyl, $(C_6-C_{10})$arylmethoxyisoquinolyl, $(C_6-C_{10})$arylmethoxybenzofuryl, $(C_6-C_{10})$arylmethoxyisobenzofuryl, $(C_6-C_{10})$arylmethoxybenzothienyl, $(C_6-C_{10})$arylmethoxypyrazolyl, $(C_6-C_{10})$arylmethoxyindolyl, $(C_6-C_{10})$arylmethoxyisoindolyl, $(C_6-C_{10})$arylmethoxypurinyl, $(C_6-C_{10})$arylmethoxycarbazolyl, $(C_6-C_{10})$arylmethoxyisoxazolyl, $(C_6-C_{10})$arylmethoxythiazolyl, $(C_6-C_{10})$arylmethoxyoxazolyl, $(C_6-C_{10})$arylmethoxybenzthiazolyl, $(C_6-C_{10})$arylmethoxybenzoxazolyl, pyridylmethoxyphenyl, furylmethoxyphenyl, pyrroylmethoxyphenyl, thienylmethoxyphenyl, isothiazolylmethoxyphenyl, imidazolylmethoxyphenyl, benzimidazolylmethoxyphenyl, tetrazolylmethoxyphenyl, pyrazinylmethoxyphenyl, pyrimidylmethoxyphenyl, quinolylmethoxyphenyl, isoquinolylmethoxyphenyl, benzofurylmethoxyphenyl, isobenzofurylmethoxyphenyl, benzothienylmethoxyphenyl, pyrazolylmethoxyphenyl, indolylmethoxyphenyl, isoindolylmethoxyphenyl, purinylmethoxyphenyl, carbazolylmethoxyphenyl, isoxazolylmethoxyphenyl, thiazolylmethoxyphenyl, oxazolylmethoxyphenyl, benzthiazolylmethoxyphenyl, and benzoxazolylmethoxyphenyl.

Most preferred compounds of the invention are those wherein Ar is optionally substituted $(C_6-C_{10})$arylmethoxyphenyl, pyridylmethoxyphenyl, thienylmethoxyphenyl, pyrazinylmethoxyphenyl, pyrimidylmethoxyphenyl, pyridazinylmethoxyphenyl, thiazolylmethoxyphenyl, or oxazolylmethoxyphenyl.

Other preferred compounds of the invention include those wherein Ar is $(C_6-C_{10})$arylmethoxy($C_6$)aryl optionally substituted by one or more, preferably one to three substituents per ring, most preferably one to three substituents on the terminal ring, wherein said substituents are independently selected from the group consisting of halo, $(C_1-C_6)$alkyl, $(C_1-C_6)$alkoxy or perfluoro$(C_1-C_3)$alkyl.

Other preferred compounds of the invention include those wherein Ar is $(C_6-C_{10})$arylmethoxy($C_2-C_9$)heteroaryl (optionally substituted by one or more, preferably one to three substituents per ring, most preferably one to three substituents on the terminal ring, wherein said substituents are independently selected from the group consisting of halo, $(C_1-C_6)$alkyl, $(C_1-C_6)$alkoxy or perfluoro$(C_1-C_3)$alkyl.

Other preferred compounds of the invention include those wherein Ar is $(C_2-C_9)$heteroarylmethoxy($C_6$)aryl or $(C_2-C_9)$heteroarylmethoxy($C_2-C_9$)heteroaryl optionally substituted by one or more, preferably one to three substituents per ring, most preferably one to three substituents on the terminal ring, wherein said substituents are independently selected from the group consisting of halo, $(C_1-C_6)$alkyl, $(C_1-C_6)$alkoxy or perfluoro$(C_1-C_3)$alkyl.

Other preferred compounds of the invention include those wherein Ar is $(C_2-C_9)$heteroarylmethoxy($C_2-C_9$)heteroaryl optionally substituted by one or more, preferably one to three substituents per ring, most preferably one to three substituents on the terminal ring, wherein said substituents are independently selected from the group consisting of halo, $(C_1-C_6)$alkyl, $(C_1-C_6)$alkoxy or perfluoro$(C_1-C_3)$alkyl.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined above.

The term "aryl", as used herein, unless otherwise indicated, includes an organic radical derived from an aromatic hydrocarbon by removal of one hydrogen, such as phenyl or naphthyl, optionally substituted by 1 to 3 suitable substituents independently selected from a suitable substituent such as fluoro, chloro, cyano, nitro, trifluoromethyl, $(C_1-C_6)$alkoxy, $(C_6-C_{10})$aryloxy, trifluoromethoxy, difluoromethoxy, or $(C_1-C_6)$alkyl.

The term "heteroaryl", as used herein, unless otherwise indicated, includes an organic radical derived from an aromatic heterocyclic compound by removal of one hydrogen, such as pyridyl, furyl, pyrroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl, optionally substituted by 1 to 3 suitable substituents as defined below such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

The term "acyl", as used herein, unless otherwise indicated, includes a radical of the general formula RCO wherein R is alkyl, alkoxy (such as methyloxy carbonyl), aryl, arylalkyl or arylalkyloxy and the terms "alkyl" or "aryl" are as defined above.

The term "acyloxy", as used herein, includes O-acyl groups wherein "acyl" is defined above.

The term "D- or L-amino acid", as used herein, unless otherwise indicated, includes glycine, alanine, valine, leucine, isoleucine, phenylalanine, asparagine, glutamine, tryptophan, proline, serine, threonine, tyrosine, hydroxyproline, cysteine, cystine, methionine, aspartic acid, glutamic acid, lysine, arginine or histidine.

The compound of formula I may have chiral centers and therefore exist in different enantiomeric forms. This invention relates to all optical isomers, diasteriomers, atropisomers, tautomers and stereoisomers of the compounds of formula I and mixtures thereof.

"A suitable substituent" is intended to mean a chemically and pharmaceutically acceptable functional group i.e., a moiety that does not negate the inhibitory activity of the inventive compounds. Such suitable substituents may be routinely selected by those skilled in the art. Illustrative examples of suitable substituents include, but are not limited to, alkyl groups, hydroxy groups, oxo groups, mercapto groups, alkylthio groups, alkoxy groups, aryl or heteroaryl groups, aralkyl or heteroaralkyl groups, aralkoxy or heteroaralkoxy groups, carboxy groups, amino groups, alkyl- and dialkylamino groups, carbamoyl groups, alkylcarbonyl groups, alkoxycarbonyl groups, alkylaminocarbonyl groups dialkyamino carbonyl groups, arylcarbonyl groups, aryloxycarbonyl groups, alkylsulfonyl groups, an arylsulfonyl groups and the like.

Specific preferred compounds of formula I are selected from the group consisting of:
(2R,5R)-1-[4-(2,5-Dimethyl-benzyloxy)-benzenesulfonyl]-5-hydroxy-piperidine-2-carboxylic acid hydroxyamide,
(2R,5R)-1-[4-(5-Fluoro-2-methyl-benzyloxy)-benzenesulfonyl]-5-hydroxy-piperidine-2-carboxylic acid hydroxyamide,
(2R,4R)-4-Hydroxy-1-[4-(2-methyl-benzyloxy)-benzenesulfonyl]-piperidine-2-carboxylic acid hydroxyamide,
(2R,5R)-1-[4-(5-Fluoro-2-trifluoromethyl-benzyloxy)-benzenesulfonyl]-5-hydroxy-piperidine-2-carboxylic acid hydroxyamide,
(2R,5R)-5-Hydroxy-1-[4-(2-isopropyl-benzyloxy)-benzenesulfonyl]-piperidine-2-carboxylic acid hydroxyamide,
(2R,5R)-1-[4-(2-Ethyl-benzyloxy)-benzenesulfonyl]-5-hydroxy-piperidine-2-carboxylic acid hydroxyamide,
(2R,4R)-1-[4-(5-Fluoro-2-methyl-benzyloxy)-benzenesulfonyl]-4-hydroxy-piperidine-2-carboxylic acid hydroxyamide,
(2R,5R)-1-[4-(2,5-Dimethyl-benzyloxy)-benzenesulfonyl]-4-hydroxy-piperidine-2carboxylic acid hydroxyamide,
(2R,5R)-1-[4-(5-Fluoro-2-trifluoromethyl-benzyloxy)-benzenesulfonyl]-5-hydroxy-5-methyl-piperidine-2-carboxylic acid hydroxyamide,
(2R,5R)-5-Hydroxy-1-[4-(2-isopropyl-benzyloxy)-benzenesulfonyl]-5-methyl-piperidine-2-carboxylic acid hydroxyamide,
(2R,5R)-5-Hydroxy-5-methyl-1-[4-(2-methyl-benzyloxy)-benzenesulfonyl]-piperidine-2-carboxylic acid hydroxyamide,
(2R,3R,5R)-5-Hydroxy-3-methyl-1-[4-(2-methyl-benzyloxy)-benzenesulfonyl]-piperidine-2-carboxylic acid hydroxyamide,
(2R,3R,5R)-5-Hydroxy-1-[4-(2-isopropyl-benzyloxy)-benzenesulfonyl]-3-methyl-piperidine-2-carboxylic acid hydroxyamide, and
(2R,3S)-1-[4-(5-Fluoro-2-trifluoromethyl-benzyloxy)-benzenesulfonyl]-3-hydroxy-3-methyl-piperidine-2-carboxylic acid hydroxyamide.

Other compounds of the invention include:
1-(4-Benzyloxy-benzenesulfonyl)-5-hydroxy-piperidine-2-carboxylic acid hydroxyamide,
1-(4-Benzyloxy-benzenesulfonyl)-5-hydroxy-piperidine-2-carboxylic acid hydroxyamide,
1-(4-Benzyloxy-benzenesulfonyl)-5-methoxy-piperidine-2-carboxylic acid hydroxyamide,
1-[4-(2-Fluoro-benzyloxy)-benzenesulfonyl]-5-hydroxy-piperidine-2-carboxylic acid hydroxyamide, 1-[4-(2,5-Difluoro-benzyloxy)-benzenesulfonyl]-5-hydroxy-piperidine-2-carboxylic acid hydroxyamide,
1-[4-(2,3-Difluoro-benzyloxy)-benzenesulfonyl]-5-hydroxy-piperidine-2-carboxylic acid hydroxyamide,
5-Hydroxy-1-[4-(2-trifluoromethyl-benzyloxy)-benzenesulfonyl]-piperidine-2-carboxylic acid hydroxyamide,
1-[4-(2,6-Difluoro-benzyloxy)-benzenesulfonyl]-5-hydroxy-piperidine-2-carboxylic acid hydroxyamide,
5-Hydroxy-1-[4-(4-methoxy-benzyloxy)-benzenesulfonyl]-piperidine-2-carboxylic acid hydroxyamide,
1-[4-(5-Chloro-thiophen-2-ylmethoxy)-benzenesulfonyl]-5-hydroxy-piperidine-2-carboxylic acid hydroxyamide,
1-[4-(3,5-Difluoro-benzyloxy)-benzenesulfonyl]-5-hydroxy-piperidine-2-carboxylic acid hydroxyamide,
1-[4-(2,4-Difluoro-benzyloxy)-benzenesulfonyl]-5-hydroxy-piperidine-2-carboxylic acid hydroxyamide,
5-Hydroxy-1-[4-(3-trifluoromethyl-benzyloxy)-benzenesulfonyl]-piperidine-2-carboxylic acid hydroxyamide,
5-Hydroxy-1-[4-(4-trifluoromethyl-benzyloxy)-benzenesulfonyl]-piperidine-2-carboxylic acid hydroxyamide,
1-[4-(2-Cyano-benzyloxy)-benzenesulfonyl]-5-hydroxy-piperidine-2-carboxylic acid hydroxyamide,
1-[4-(3-Cyano-benzyloxy)-benzenesulfonyl]-5-hydroxy-piperidine-2-carboxylic acid hydroxyamide,
5-Hydroxy-1-[4-(2-methyl-benzyloxy)-benzenesulfonyl]-piperidine-2-carboxylic acid hydroxyamide,
1-[4-(5-Fluoro-2-methyl-benzyloxy)-benzenesulfonyl]-5-hydroxy-piperidine-2-carboxylic acid hydroxyamide,
1-[4-(4-Fluoro-2-methyl-benzyloxy)-benzenesulfonyl]-5-hydroxy-piperidine-2-carboxylic acid hydroxyamide,
1-[4-(2,6-Dimethyl-benzyloxy)-benzenesulfonyl]-5-hydroxy-piperidine-2-carboxylic acid hydroxyamide,
1-[4-(2-Chloro-benzyloxy)-benzenesulfonyl]-5-hydroxy-piperidine-2-carboxylic acid hydroxyamide,
5-Hydroxy-1-[4-(3,4,5-trifluoro-benzyloxy)-benzenesulfonyl]-piperidine-2-carboxylic acid hydroxyamide,
5-Hydroxy-1-[4-(naphthalen-1-ylmethoxy)-benzenesulfonyl]-piperidine-2-carboxylic acid hydroxyamide,
1-[4-(2,4-Dimethyl-benzyloxy)-benzenesulfonyl]-5-hydroxy-piperidine-2-carboxylic acid hydroxyamide,
5-Hydroxy-1-[4-(2-methyl-pyridin-3-ylmethoxy)-benzenesulfonyl]-piperidine-2-carboxylic acid hydroxyamide,
5-Hydroxy-1-[4-(4-isopropyl-benzyloxy)-benzenesulfonyl]-piperidine-2-carboxylic acid hydroxyamide,
1-[4-(2-Bromo-benzyloxy)-benzenesulfonyl]-5-hydroxy-piperidine-2-carboxylic acid hydroxyamide,
5-Hydroxy-1-[4-(2-iodo-benzyloxy)-benzenesulfonyl]-piperidine-2-carboxylic acid hydroxyamide,
5-Hydroxy-1-[4-(pyridin-2-ylmethoxy)-benzenesulfonyl]-piperidine-2-carboxylic acid hydroxyamide,
1-[4-(2,3-Dimethyl-benzyloxy)-benzenesulfonyl]-5-hydroxy-piperidine-2-carboxylic acid hydroxyamide,
1-[4-(3-Fluoro-2-methyl-benzyloxy)-benzenesulfonyl]-5-hydroxy-piperidine-2-carboxylic acid hydroxyamide,
1-[4-(5-Chloro-2-methyl-benzyloxy)-benzenesulfonyl]-5-hydroxy-piperidine-2-carboxylic acid hydroxyamide,
1-[4-(3,5-Dimethyl-benzyloxy)-benzenesulfonyl]-5-hydroxy-piperidine-2-carboxylic acid hydroxyamide,
1-[4-(3-Fluoro-5-methyl-benzyloxy)-benzenesulfonyl]-5-hydroxy-piperidine-2-carboxylic acid hydroxyamide, 1-[4-(5-Fluoro-2-trifluoromethyl-benzyloxy)-benzenesulfonyl]-5-hydroxy-piperidine-2-carboxylic acid hydroxyamide,
5-Hydroxy-1-[4-(2-isopropyl-benzyloxy)-benzenesulfonyl]-piperidine-2-carboxylic acid hydroxyamide,
5-Hydroxy-1-[4-(4-methyl-naphthalen-1-ylmethoxy)-benzenesulfonyl]-piperidine-2-carboxylic acid hydroxyamide,
1-[4-(2-Bromo-5-fluoro-benzyloxy)-benzenesulfonyl]-5-hydroxy-piperidine-2-carboxylic acid hydroxyamide,
1-[4-(2-Ethyl-benzyloxy)-benzenesulfonyl]-5-hydroxy-piperidine-2-carboxylic acid hydroxyamide,
1-[4-(2,5-Dibromo-benzyloxy)-benzenesulfonyl]-5-hydroxy-piperidine-2-carboxylic acid hydroxyamide,
1-[4-(2-Bromo-5-methyl-benzyloxy)-benzenesulfonyl]-5-hydroxy-piperidine-2-carboxylic acid hydroxyamide,
1-(4-Benzyloxy-benzenesulfonyl)-5-hydroxy-5-methyl-piperidine-2-carboxylic acid hydroxyamide,
1-[4-(4-Fluoro-benzyloxy)-benzenesulfonyl]-3-hydroxy-piperidine-2-carboxylic acid hydroxyamide,
1-[4-(4-Fluoro-benzyloxy)-benzenesulfonyl]-3-methoxy-piperidine-2-carboxylic acid hydroxyamide,
3-Ethoxy-1-[4-(4-fluoro-benzyloxy)-benzenesulfonyl]-piperidine-2-carboxylic acid hydroxyamide,
1-[4-(4-Fluoro-benzyloxy)-benzenesulfonyl]-3-hydroxy-3-methyl-piperidine-2-carboxylic acid hydroxyamide,
1-[4-(4-Fluoro-benzyloxy)-benzenesulfonyl]-3-hydroxy-3-methyl-piperidine-2-carboxylic acid hydroxyamide,
3-Ethyl-1-[4-(4-fluoro-benzyloxy)-benzenesulfonyl]-3-hydroxy-piperidine-2-carboxylic acid hydroxyamide,
3-Ethyl-1-[4-(4-fluoro-benzyloxy)-benzenesulfonyl]-3-hydroxy-piperidine-2-carboxylic acid hydroxyamide,
3-Butyl-1-[4-(4-fluoro-benzyloxy)-benzenesulfonyl]-3-hydroxy-piperidine-2-carboxylic acid hydroxyamide,
1-[4-(4-Fluoro-benzyloxy)-benzenesulfonyl]-4-hydroxy-piperidine-2-carboxylic acid hydroxyamide,
1-(4-Benzyloxy-benzenesulfonyl)-4-hydroxy-piperidine-2-carboxylic acid hydroxyamide,
1-[4-(4-Fluoro-benzyloxy)-benzenesulfonyl]-4-methoxy-piperidine-2-carboxylic acid hydroxyamide,
1-[4-(4-Fluoro-benzyloxy)-benzenesulfonyl]-4-hydroxy-4-methyl-piperidine-2-carboxylic acid allyloxy-amide,
1-[4-(4-Fluoro-benzyloxy)-benzenesulfonyl]-4-hydroxy-4-methyl-piperidine-2-carboxylic acid hydroxyamide,
1-[4-(4-Fluoro-benzyloxy)-benzenesulfonyl]-4-hydroxy-4-phenyl-piperidine-2-carboxylic acid hydroxyamide,
4-Allyl-1-(4-benzyloxy-benzenesulfonyl)-4-hydroxy-piperidine-2-carboxylic acid hydroxyamide,
1-(4-Benzyloxy-benzenesulfonyl)-4-hydroxy-4-methyl-piperidine-2-carboxylic acid hydroxyamide,
1-(4-Benzyloxy-benzenesulfonyl)-4-hexyl-4-hydroxy-piperidine-2-carboxylic acid hydroxyamide,
4-Benzyl-1-(4-benzyloxy-benzenesulfonyl)-4-hydroxy-piperidine-2-carboxylic acid hydroxyamide,
1-(4-Benzyloxy-benzenesulfonyl)-4-methoxy-piperidine-2-carboxylic acid hydroxy-methyl-amide,
1-[4-(4-Chloro-benzyloxy)-benzenesulfonyl]-4-hydroxy-piperidine-2-carboxylic acid hydroxyamide,
4-Hydroxy-1-[4-(2-methoxy-benzyloxy)-benzenesulfonyl]-piperidine-2-carboxylic acid hydroxyamide,
4-Hydroxy-1-[4-(2-methyl-benzyloxy)-benzenesulfonyl]-piperidine-2-carboxylic acid hydroxyamide,
4-Hydroxy-1-[4-(4-methyl-benzyloxy)-benzenesulfonyl]-piperidine-2-carboxylic acid hydroxyamide,
4-Hydroxy-1-[4-(3-methyl-benzyloxy)-benzenesulfonyl]-piperidine-2-carboxylic acid hydroxyamide,
1-[4-(2-Chloro-benzyloxy)-benzenesulfonyl]-4-hydroxy-piperidine-2-carboxylic acid hydroxyamide,
1-[4-(2-Fluoro-benzyloxy)-benzenesulfonyl]-4-hydroxy-piperidine-2-carboxylic acid hydroxyamide,
1-[4-(3-Fluoro-benzyloxy)-benzenesulfonyl]-4-hydroxy-piperidine-2-carboxylic acid hydroxyamide,
4-Hydroxy-1-[4-(3-methoxy-benzyloxy)-benzenesulfonyl]-piperidine-2-carboxylic acid hydroxyamide,
1-[4-(3-Chloro-benzyloxy)-benzenesulfonyl]-4-hydroxy-piperidine-2-carboxylic acid hydroxyamide,
1-(4-Benzyloxy-benzenesulfonyl)-4-methoxy-piperidine-2-carboxylic acid hydroxyamide,
1-[4-(Benzo[1,3]dioxol-5-ylmethoxy)-benzenesulfonyl]-4-hydroxy-piperidine-2-carboxylic acid hydroxyamide,
1-[4-(3,5-Dimethyl-isoxazol-4-ylmethoxy)-benzenesulfonyl]-4-hydroxy-piperidine-2-carboxylic acid hydroxyamide,
1-(4-Benzyloxy-benzenesulfonyl)-4-ethoxy-piperidine-2-carboxylic acid hydroxyamide,
3-[4-(4-Hydroxy-2-hydroxycarbamoyl-piperidine-1-sulfonyl)-phenoxymethyl]-benzoic acid methyl ester,
1-[4-(2,5-Dimethyl-benzyloxy)-benzenesulfonyl]-4-hydroxy-piperidine-2-carboxylic acid hydroxyamide,
1-[4-(3-Cyano-benzyloxy)-benzenesulfonyl]-4-hydroxy-piperidine-2-carboxylic acid hydroxyamide,
1-[4-(4-Cyano-benzyloxy)-benzenesulfonyl]-4-hydroxy-piperidine-2-carboxylic acid hydroxyamide,
1-[4-(3,5-Difluoro-benzyloxy)-benzenesulfonyl]-4-hydroxy-piperidine-2-carboxylic acid hydroxyamide,
4-Hydroxy-1-[4-(3,4,5-trifluoro-benzyloxy)-benzenesulfonyl]-piperidine-2-carboxylic acid hydroxyamide,
1-[4-(3,4-Difluoro-benzyloxy)-benzenesulfonyl]-4-hydroxy-piperidine-2-carboxylic acid hydroxyamide,
4-Hydroxy-1-[4-(2-trifluoromethyl-benzyloxy)-benzenesulfonyl]-piperidine-2-carboxylic acid hydroxyamide,
1-[4-(2,4-Bis-trifluoromethyl-benzyloxy)-benzenesulfonyl]-4-hydroxy-piperidine-2-carboxylic acid hydroxyamide,
4-Hydroxy-1-[4-(naphthalen-2-ylmethoxy)-benzenesulfonyl]-piperidine-2-carboxylic acid hydroxyamide,
4-Hydroxy-1-[4-(4-isopropyl-benzyloxy)-benzenesulfonyl]-piperidine-2-carboxylic acid hydroxyamide,
1-[4-(3,5-Dimethyl-benzyloxy)-benzenesulfonyl]-4-hydroxy-piperidine-2-carboxylic acid hydroxyamide,
4-Hydroxy-1-(4-phenethyloxy-benzenesulfonyl)-piperidine-2-carboxylic acid hydroxyamide,
4-[4-(4-Hydroxy-2-hydroxycarbamoyl-piperidine-1-sulfonyl)-phenoxymethyl]-benzoic acid methyl ester,
1-[4-(2,6-Dichloro-benzyloxy)-benzenesulfonyl]-4-hydroxy-piperidine-2-carboxylic acid hydroxyamide,
4-Hydroxy-4-methyl-1-[4-(2-methyl-benzyloxy)-benzenesulfonyl]-piperidine-2-carboxylic acid hydroxyamide,
4-Hydroxy-4-methyl-1-[4-(2-methyl-benzyloxy)-benzenesulfonyl]-piperidine-2-carboxylic acid hydroxyamide,
1-[4-(4-tert-Butyl-benzyloxy)-benzenesulfonyl]-4-hydroxy-piperidine-2-carboxylic acid hydroxyamide,
4-Hydroxy-1-[4-(naphthalen-1-ylmethoxy)-benzenesulfonyl]-piperidine-2-carboxylic acid hydroxyamide,
1-[4-(5-Fluoro-2-methyl-benzyloxy)-benzenesulfonyl]-4-hydroxy-piperidine-2-carboxylic acid hydroxyamide, 1-[4-(4-Fluoro-2-methyl-benzyloxy)-benzenesulfonyl]-4-hydroxy-piperidine-2-carboxylic acid hydroxyamide, 1-[4-(2-Fluoro-6-trifluoromethyl-benzyloxy)-benzenesulfonyl]-4-hydroxy-piperidine-2carboxylic acid hydroxyamide, 1-[4-(3,5-Difluoro-benzyloxy)-benzenesulfonyl]-4-hydroxy-4-methyl-piperidine-2-carboxylic acid hydroxyamide, 1-[4-(3,5-Difluoro-benzyloxy)-benzenesulfonyl]-4-hydroxy-4-methyl-piperidine-2carboxylic acid hydroxyamide, 4-Hydroxy-1-[4-(2-methyl-naphthalen-1-ylmethoxy)-benzenesulfonyl]-piperidine-2-carboxylic acid hydroxyamide, 4-Hydroxy-1-[4-(4-methyl-naphthalen-1-ylmethoxy)-benzenesulfonyl]-piperidine-2-carboxylic acid hydroxyamide, 1-[4-(Biphenyl-2-ylmethoxy)-benzenesulfonyl]-4-hydroxy-piperidine-2-carboxylic acid hydroxyamide, 4-Hydroxy-1-[4-(2-methyl-pyridin-3-ylmethoxy)-benzenesulfonyl]-piperidine-2-carboxylic acid hydroxyamide, 4-Hydroxy-1-[4-(2-methyl-benzyloxy)-benzenesulfonyl]-piperidine-2-carboxylic acid hydroxyamide, 1-[4-(5-Fluoro-2-methyl-benzyloxy)-benzenesulfonyl]-4-hydroxy-piperidine-2-carboxylic acid hydroxyamide, 1-[4-(5-Fluoro-2-trifluoromethyl-benzyloxy)-benzenesulfonyl]-5-hydroxy-3,3-dimethyl-piperidine-2-carboxylic acid hydroxyamide, 5-[4-(5-Fluoro-2-trifluoromethyl-benzyloxy)-benzenesulfonyl]-7-hydroxy-5-aza-spiro[2.5]octane-4-carboxylic acid hydroxyamide, 1-[4-(5-Fluoro-2-trifluoromethyl-benzyloxy)-benzenesulfonyl]-5-hydroxy-3,3-diethyl-piperidine-2-carboxylic acid hydroxyamide, 7-[4-(5-Fluoro-2-trifluoromethyl-benzyloxy)-benzenesulfonyl]-9-hydroxy-7-aza-spiro[4.5]decane-6-carboxylic acid hydroxyamide, 1-[4-(5-Fluoro-2-trifluoromethyl-benzyloxy)-benzenesulfonyl]-5-hydroxy-3-methyl-piperidine-2-carboxylic acid hydroxyamide, 1-[5-(5-Fluoro-2-trifluoromethyl-benzyloxy)-pyridine-2-sulfonyl]-hydroxy-piperidine-2-carboxylic acid hydroxyamide, 1-[6-(5-Fluoro-2-trifluoromethyl-benzyloxy)-pyridine-3-sulfonyl]-hydroxy-piperidine-2-carboxylic acid hydroxyamide, 1-[5-(5-Fluoro-2-trifluoromethyl-benzyloxy)-thiophene-2-sulfonyl]-hydroxy-piperidine-2-carboxylic acid hydroxyamide, 4-Hydroxy-1-[3-methyl-4-(2-trifluoromethyl-benzyloxy)-benzenesulfonyl]-piperidine-2-carboxylic acid hydroxyamide, 5-Hydroxy-3-trifluoromethyl-1-[4-(2-trifluoromethyl-benzyloxy)-benzenesulfonyl]-piperidine-2-carboxylic acid hydroxyamide, 1-[4-(5-Fluoro-2-trifluoromethyl-benzyloxy)-benzenesulfonyl]-5-hydroxy-3-trifluoromethyl-piperidine-2-carboxylic acid hydroxyamide, 3,3-Difluoro-1-[4-(5-fluoro-2-trifluoromethyl-benzyloxy)-benzenesulfonyl]-5-hydroxy-piperidine-2-carboxylic acid hydroxyamide, 5-Ethyl-1-[4-(5-fluoro-2-trifluoromethyl-benzyloxy)-benzenesulfonyl]-5-hydroxy-piperidine-2-carboxylic acid hydroxyamide, 1-[4-(5-Fluoro-2-trifluoromethyl-benzyloxy)-benzenesulfonyl]-5-hydroxy-5-isopropyl-piperidine-2-carboxylic acid hydroxyamide, 4-Hydroxy-1-[4-(2-methyl-pyridin-3-ylmethoxy)-benzenesulfonyl]-piperidine-2-carboxylic acid hydroxyamide, and 1-[4-(3,5-Difluoro-benzyloxy)-benzenesulfonyl]-4-hydroxy-piperidine-2-carboxylic acid hydroxyamide.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i. e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

The present invention also relates to a pharmaceutical composition for the treatment of a condition selected from the group consisting of arthritis (including osteoarthritis and rheumatoid arthritis), inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, cancer (such as solid tumor cancer including colon cancer breast cancer, lung cancer and prostrate cancer and hematopoietic malignancies including leukemias and lymphomas), tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis and septic shock in a mammal, including a human, comprising an amount of a compound of formula I or a pharmaceutically acceptable salt thereof effective in such treatments and a pharmaceutically acceptable carrier.

The present invention also relates to a pharmaceutical composition for the treatment of diseases characterized by metalloproteinase activity and other diseases characterized by mammalian reprolysin activity (preferably TACE activity) in a mammal, including a human, comprising an amount of a compound of formula I or a pharmaceutically acceptable salt thereof effective in such treatments and a pharmaceutically acceptable carrier.

The present invention also relates to a pharmaceutical composition for the inhibition of a) matrix metalloproteinases or other metalloproteinases involved in matrix degradation, or (b) a mammalian reprolysin (such as aggrecanase or ADAM's TS-1, 10, 12, 15 and 17, most preferably ADAM-17) in a mammal, including a human, comprising an effective amount of a compound of formula I or a pharmaceutically acceptable salt thereof.

The present invention also relates to a method for treating a condition selected from the group consisting of arthritis (including osteoarthritis and rheumatoid arthritis), inflammatory bowel disease, Crohn's disease, emphysema, acute respiratory distress syndrome, asthma, chronic obstructive pulmonary disease, Alzheimers disease, organ transplant toxicity, cachexia, allergic reactions, allergic contact hypersensitivity, cancer (such as solid tumor cancer including colon cancer breast cancer, lung cancer and prostrate cancer and hematopoietic malignancies including leukemias and lymphomas), tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neurodegenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis and septic shock in a mammal, including a human, comprising administering to said mammal an amount of a compound of formula I or a pharmaceutically acceptable salt thereof effective in treating such a condition.

The present invention also relates to the treatment of diseases characterized by matrix metalloproteinase activity and other diseases characterized by mammalian reprolysin activity (preferably TACE) in a mammal, including a human, comprising administering to said mammal an amount of a compound of formula I or a pharmaceutically acceptable salt thereof effective in treating such a condition.

The present invention also relates to a method for the inhibition of (a) matrix metalloproteinases or other metalloproteinases involved in matrix degradation, or (b) a mammalian reprolysin (such as aggrecanase or ADAM's TS-1, 10, 12, 15 and 17; preferably ADAM-17) in a mammal, including a human, comprising administering to said mammal an effective amount of a compound of formula I or a pharmaceutically acceptable salt thereof.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

This invention also encompasses pharmaceutical compositions containing prodrugs of compounds of the formula I. This invention also encompasses methods of treating or preventing disorders that can be treated or prevented by the inhibition of matrix metalloproteinases or the inhibition of mammalian reprolysin comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies and TNF receptor immunoglobulin molecules (such as Enbrel®), COX-2 inhibitors, low dose methotrexate, lefunimide, hydroxychloroquine, d-penicilamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib and rofecoxib, analgesics and intraarticular therapies such as corticosteroids and hyaluronic acids such as hyalgan and synvisc.

The compounds of the present invention may also be used in combination with anticancer agents such as endostatin and angiostatin or cytotoxic drugs such as adriamycin, daunomycin, cis-platinum, etoposide, taxol, taxotere and alkaloids, such as vincristine, and antimetabolites such as methotrexate.

The compounds of the present invention may also be used in combination with cardiovascular agents such as calcium channel blockers, lipid lowering agents such as statins, fibrates, beta-blockers, Ace inhibitors, Angiotensin-2 receptor antagonists and platelet aggregation inhibitors.

The compounds of the present invention may also be used in combination with CNS agents such as antidepressants (such as sertraline), anti-Parkinsonian drugs (such as deprenyl, L-dopa, requip, miratex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metryfonate.

The compounds of the present invention may also be used in combination with osteoporosis agents such as roloxifene, droloxifene or fosomax and immunosuppressant agents such as FK-506 and rapamycin.

DETAILED DESCRIPTION OF THE INVENTION

The following reaction Schemes illustrate the preparation of the compounds of the present invention. Unless otherwise indicated Ar, and $R^1$–$R^8$ in the reaction Schemes and the discussion that follow are defined as above.

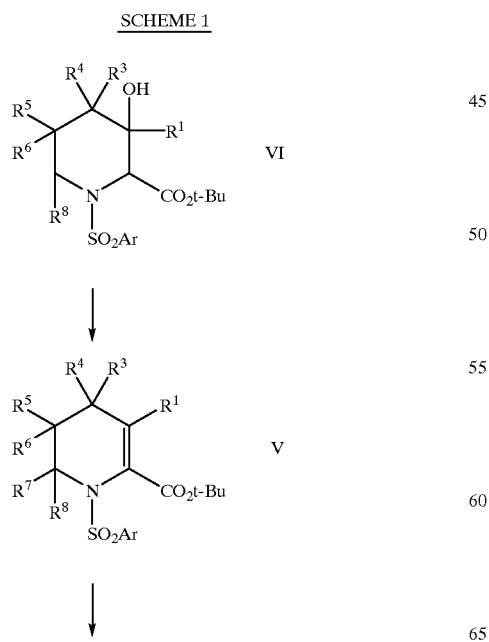

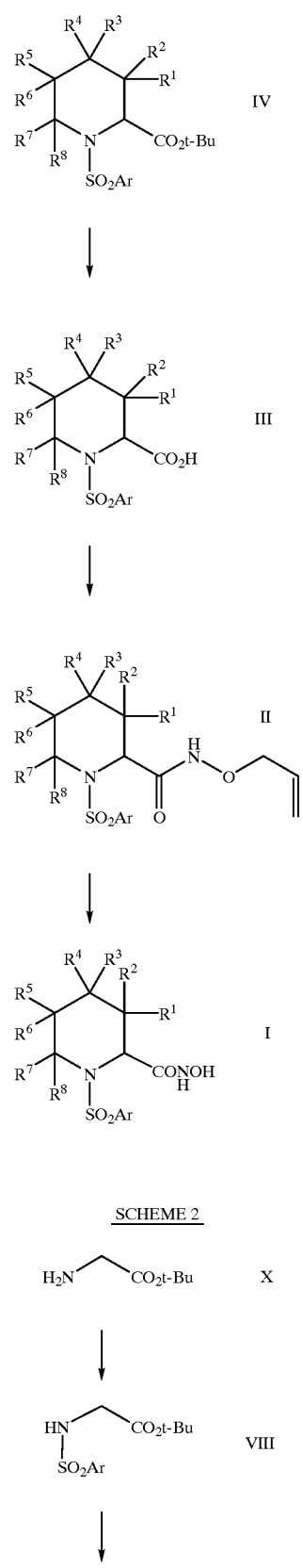

-continued
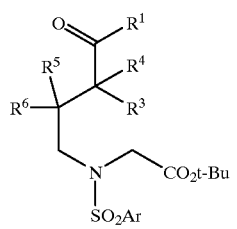
VII
↓
VI
SCHEME 3
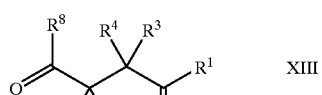
XIII
↓
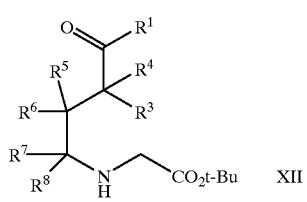
XII
↓
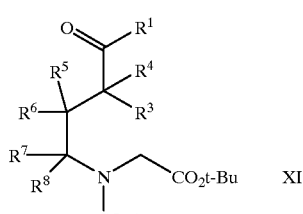
XI
↓
VI
SCHEME 4
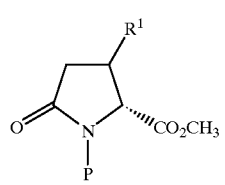
XXI
↓
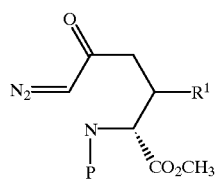
XX
↓
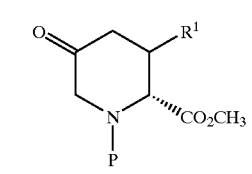
XIX
↓
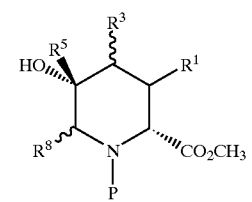
XVIII
↓
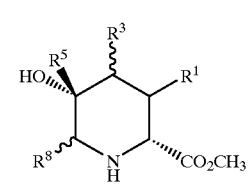
XVII
↓
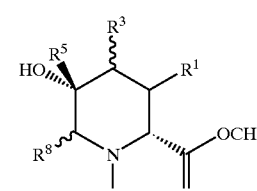
XVI
↓
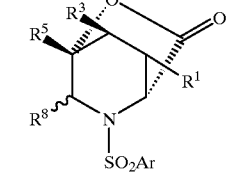
XV
↓

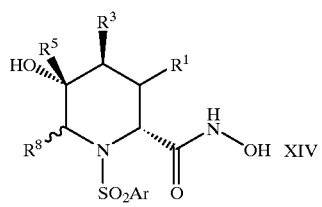
XIV
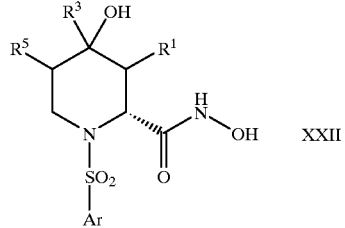
XXII
SCHEME 5
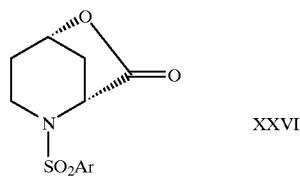
XXVI
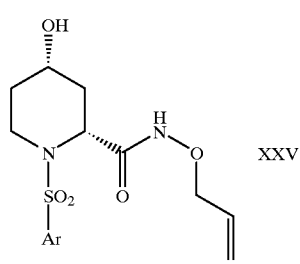
XXV
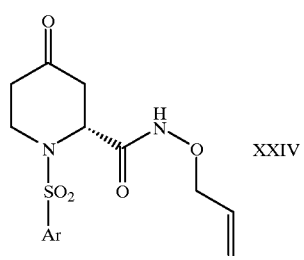
XXIV
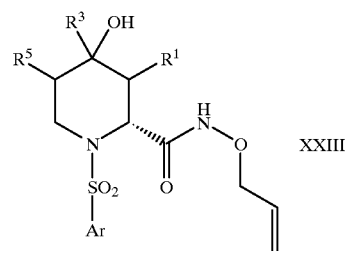
XXIII
SCHEME 6
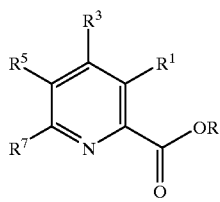
XXVIII
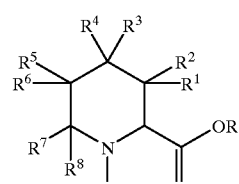
XXVII
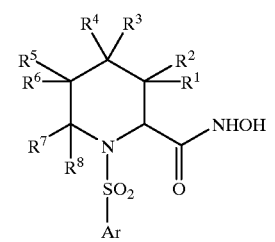
I
SCHEME 7
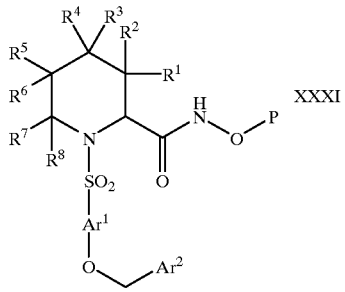
XXXI

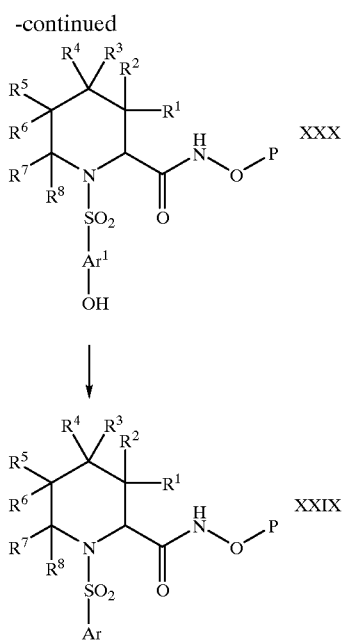

Scheme 1 refers to the preparation of compounds of the formula I. Referring to Scheme 1, compounds of the formula I are prepared from compounds of the formula II by reaction with a reducing agent, such as triethylammonium formate in the presence of a palladium catalyst, preferably in the presence of a suitable solvent. Suitable palladium catalysts include palladium(0) salts, preferably palladium tetrakistriphenyl phosphine. Suitable solvents include polar solvents, preferably acetonitrile-water mixtures. The aforesaid reaction is performed at a temperature from about 23° C. to about 70° C. (i.e. the boiling point of the solvent), for a period from about 1 hour to about 6 hours, preferably about 2 hours.

The compound of formula II is prepared from a compound of formula III by reaction with a coupling agent followed by the addition of O-allylhydroxylamine hydrochloride and a base, preferably in the presence of a solvent. One of ordinary skill in the art will understand that other hydroxylamines can be substituted for O-allylhydroxyl amine in analogous reactions. Suitable coupling agents include benzotriazol-1-yloxytris(dimethylamino) phosphonium hexafluorophosphate or carbodiimide reagents in combination with 1-hydroxybenzotriazole, preferably benzotriazol-1-yloxytris(dimethylamino) phosphonium hexafluorophosphate or 1-3-(dimethylaminopropyl)-3-ethylcarbodiimide. Suitable bases include tertiary amine bases such as diisopropylethylamine or triethylamine or pyridine bases such as pyridine, preferably the base is diisopropylethylamine. Suitable solvents include tetrahydrofuran, acetonitrile or methylene chloride, preferably methylene chloride. The aforesaid reaction is performed at a temperature from about 0° C. to about 40° C., preferably about 23° C. The aforesaid reaction time ranges from about 2 hours to about 48 hours, preferably about for 2 hours to about 36 hours.

The compound of formula III is prepared from a compound of formula IV by reaction with an appropriate strong acid, such as hydrochloric acid or trifluoroacetic acid (preferably trifluoroacetic acid), preferably in the presence of a solvent such as dichloromethane. The aforesaid reaction is performed at a temperature from about 0° C. to about 23° C., for a period from about 1 hour to about 6 hours, preferably 1 to 3 hours.

The compound of formula IV is prepared from a compound of the formula V via the addition of a nucleophile of the formula $R^2M$. Suitable nucleophiles include carbon nucleophiles, preferably an organocuprate generated from the appropriate organo lithium or Grignard reagent and the appropriate copper salt. Preferably, the aforesaid reaction is run in the presence of a solvent such as tetrahydrofuran, 1,2-dimethoxyethane or diethyl ether, preferably tetrahydrofuran. The aforesaid reaction is run at a temperature from about −78° C. to about 23° C. for a period from about 1 hour to about 6 hours.

The compound of formula V is prepared from a compound of formula VI by reaction with a sulfonyl halide or acid anhydride in the presence of a solvent. Suitable sulfonyl halides include methanesulfonyl chloride or p-toluenesulfonyl chloride, preferably methanesulfonyl chloride. Preferably, the aforesaid reaction is performed in the presence of a base such as trialkylamine or pyridine base. Suitable solvents include tetrahydrofuran, methylene chloride, preferably tetrahydrofuran. The aforesaid reaction is run at a temperature from about 0° C. to the boiling point of the solvent, preferably at about 0° C., for a period from about 30 minutes to about 6 hours.

Compounds of the formula VI are prepared according to the methods of Schemes 2 and 3.

One of ordinary skill in the art will appreciate that the compounds of formula I may possess hydroxy substituents at groups $R^1$–$R^8$. When the intermediates of formula II–XIV possess a hydroxy substituent at any of groups $R^1$–$R^8$ they are carried through the reaction steps in the form of protected hydroxylate groups. Suitable protected hydroxylates are those described in Greene and Wuts, "*Protecting Groups in Organic Synthesis*," (John Wiley & Son Press, 2nd Ed). These protecting groups can also be removed according to the methods described in said Green and Wuts, id.

Scheme 2 refers to the preparation of compounds of the formula VI which can be converted into compounds of the formula I according to the methods of Scheme 1. Referring to Scheme 2, compounds of the formula VI are prepared from compounds of the formula VII by reaction with a suitable base such as a sodium or potassium alkoxide or a lithium, sodium or potassium dialkylamide, preferably potassium tert-butoxide. Preferably, the aforesaid reaction is run in the presence of a solvent such as a dialkyl ether, toluene, alcohols (such as those corresponding to the alkoxide base), or tetrahydrofuran, preferably tetrahydrofuran. The aforesaid reaction is run at a temperature from −78° C. to the boiling point of the solvent, preferably at about 0° C. to about 23° C., for a period from about 30 minutes to about 24 hours.

The compound of formula VII may be prepared by treatment of the compound of formula VIII with the appropriate gamma-hydroxyl ketone of the formula

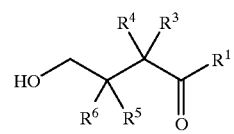

in the presence of an azodicarboxylate and a phosphine reagent in a suitable solvent (under so called Mitsunobu conditions). Suitable azodicarboxylates include dialkylazodicarboxylates such as diethylazodicarboxylate or diisopropylazodicarboxylate, preferably diethylazodicarboxylate. Suitable phosphine reagents include triaryl or trialkyl phosphines, preferably triphenylphosphine. Suitable solvents include ethereal solvents, preferably THF. The aforesaid reaction is performed at a temperature from about 0° C. to about 50° C. preferably about 25° C. The aforesaid reaction time ranges from about 12 hours to about 24 hours.

The compound of formula VIII may be prepared by treatment of glycine tert butyl ester hydrochloride salt (X) with a compound of the formula $ArSO_2L$, wherein L is a halide selected from chloro or bromo, and a base in the presence of a solvent. Suitable bases include a trialkylamine or a pyridine base. Suitable solvents include N,N-dimethylformamide or dichloromethane. The aforesaid reaction is run for a period of time from about 0.5 to about 20 hours, preferably from about 1 to about 3 hours, at a temperature from about 0° C. to 50° C.

Glycine tert butyl ester hydrochloride salt (X) is commercially available. The compound of formula IX may be prepared by the procedures described in *J. Org. Chem.*, 1984, p1248–57. The compounds of formula $ArSO_2L$ are commercially available or can be made by methods well known to those of ordinary skill in the art. One method for preparing the compounds of Formula $ArSO_2L$ is described in PCT publication WO 98/07697, published Feb. 26, 1998.

Scheme 3 refers to an alternate preparation of compounds of the formula VI. Compounds of the formula VI can be converted into compounds of the formula I according to the methods of Scheme 1. Referring to Scheme 3, compounds of the formula VI are prepared from compounds of the formula XI by methods analogous to those of the conversion of compounds of formula VII to compounds of formula VI in Scheme 2.

Compounds of the formula XI are prepared from compounds of the formula XII by treatment with a compound of the formula $ArSO_2L$, wherein L is a leaving group such as chloro or bromo, and a base in the presence of a solvent. Suitable solvents include N,N-dimethylformamide, dichloromethane or etheral solvent-water mixtures (ie. THF-water, dioxane-water or DME-water), preferably N,N-dimethylformamide. Suitable bases include alkali metal hydroxide salts, trialkylamine or pyridine bases such as triethylamine or diisopropylethylamine. The aforesaid reaction is run for a period of time from about 0.5 hours to about 20 hours, preferably from about 1 hour to about 3 hours, at a temperature from about 0° C. to 50° C.

Compounds of the formula XII are prepared from coupling compounds of the formula XIII with glycine tert butyl ester hydrochloride salt (X), in the presence of a dehydrating agent such as molecular sieves (4 Angstrom) or with the azeotropic removal of water, in a solvent, followed by reaction with a suitable cuprate reagent of the formula $(R^7)_2CuLi$. Suitable solvents for dehydration include benzene or toluene at a temperature or 23° C. to the boiling point of the solvent for a period of about 30 minutes to 12 hours. Suitable solvents for the cuprate coupling include tetrahydrofuran or diethyl ether, preferably tetrahydrofuran. The aforesaid cuprate reaction is run at a temperature from about –78° C. to about 23° C., for a period from about 30 minutes to about 2 hours.

The compound of formula $ArSO_2L$ and glycine tert butyl ester hydrochloride can be prepared by methods well known to those of ordinary skill in the art.

Compounds of the formula XIII can be prepared from compounds of the formula IX, from Scheme 2, according to the following procedure. The compound of formula IX is protected with an appropriate protecting group for the carbonyl group, such as a dialkyl ketal or acetal or a cyclic ketal or acetal, following the addition of a alkanol or diol, preferably ethylene glycol in the presence of a solvent such as benzene or toluene and a catalytic amount of an acid such as p-toluenesulfonic acid. The reaction is heated to about the boiling point of the solvent for a period of time between 2 hours and 24 hours to give the ketal or acetal. This ketal or acetal can then be oxidized by a variety of standard methods such as the Swern oxidation. Deprotection of the acetal or ketal using an appropriate acid such as hydrochloric acid will provide the compound of formula XIII.

Scheme 4 refers to the preparation of compounds of the formula XIV. Compounds of the formula XIV are compounds of the formula I, wherein $R^2$, $R^3$, $R^4$, $R^5$, $R^7$ and $R^8$ are each hydrogen, $R^1$ is as defined above and $R^6$ is hydroxy; or wherein $R^2$, $R^3$, $R^4$, $R^7$ and $R^8$ are each hydrogen, $R^1$ and $R^5$ are as defined above and $R^6$ is hydroxy; or wherein $R^2$, $R^4$, $R^5$, $R^7$ and $R^6$ are each hydrogen, $R^1$ and $R^3$ are as defined above and $R^6$ is hydroxy; or wherein $R^2$, $R^3$, $R^4$, $R^5$ and $R^7$ are each hydrogen, $R^1$ and $R^8$ are as defined above and $R^6$ is hydroxy.

Referring to Scheme 4, a compound of the formula XIV is prepared from a compound of the formula XV by reaction with hydroxylamine in a polar solvent. Hydroxylamine may be prepared via the addition of sodium alkoxide to a solution of hydroxylamine hydrochloride in a solvent, preferably methanol. Suitable solvents for the aforementioned reaction include low boiling alcohols such as ethanol or methanol, preferably the solvent is methanol. The aforesaid reaction is run at a temperature of about 0° C. to about 80° C., preferably about 60° C., for a period of about 10 minutes to about 6 hours, preferably about 1 hour.

The compound of formula XV is prepared from a compound of formula XVI by dehydration in a solvent. Suitable dehydrating conditions include azeotropic removal of water in the presence of an acid catalyst such as methanesulfonic acid or p-toluenesulfonic acid, preferably p-toluenesulfonic acid. Alternatively, molecular sieves can act as a water scavenger. Suitable solvents include high boiling aprotic solvents such as benzene or toluene, preferably toluene. The aforesaid reaction is run at a temperature of about 60° C. to about 110° C., preferably about 90° C., for a period of about 10 minutes to about 4 hours, preferably about 2 hours.

The compound of formula XVI is prepared from a compound of formula XVII by reaction with the appropriate arylsulfonyl halide and a tertiary amine base in a suitable solvent. Suitable solvents include N,N-dimethylformamide. The aforesaid reaction is run at a temperature of about 0° C. to about 23° C., preferably about 0° C., for a period of about 10 minutes to about 4 hours, preferably about 2 hours.

The compound of formula XVII is prepared from a compound of the formula XVIII by reaction with an acid in a suitable solvent. Suitable acids include trifluoroacetic acid or methanesulfonic acid, preferably trifluoroacetic acid. Suitable solvents include methylene chloride. The aforesaid reaction is run at a temperature of about 0° C. to about 30° C., preferably at about 23° C., for a period of about 30 minutes to about 4 hours, preferably about 4 hours.

The compound of formula XVIII, wherein P is 2-tert-butoxycarbonyl, $R^3$, $R^5$, and $R^8$ are each hydrogen and $R^1$ is as defined above, is prepared from a compound of the formula XIX by reaction with a reducing agent in an inert solvent. Suitable reducing agents include lithium borohydride, sodium borohydride, preferably sodium borohydride. Suitable solvents include tetrahydrofuran-water mixtures, ethanol or methanol preferably methanol. The aforesaid reaction is run at a temperature of about −10° C. to about 30° C., preferably at about 0° C., for a period of about 5 minutes to about 4 hours, preferably about 30 minutes.

Alternatively, compounds of the formula XVIII, wherein P is as defined above, $R^3$ and $R^8$ are each hydrogen and $R^1$ and $R^5$ are as defined as above, can be prepared from a compound of the formula XIX by reaction with a Grignard reagent of the formula $R^5$ MgL, wherein L is a halogen, in the presence of an organolanthanide salt in an inert solvent. Suitable organolanthanide salts include cerium (III) chloride. Suitable solvents include tetrahydrofuran. The aforesaid reaction is run at a temperature of about −50° C. to about 0° C. for about 1 minute to about 6 hours.

Alternatively, compounds of the formula XVIII, wherein P is as defined above, $R^5$ and $R^8$ are each hydrogen and $R^1$ and $R^3$ are as defined above, can be prepared from a compound of the formula XIX by reaction with a compound of the formula $R^3L$, wherein L is halo and $R^3$ are as defined above, and a base in a solvent. Suitable bases include lithium diisopropylamide, lithium hexamethyldisilazane, potassium hexamethyldisilazane, or sodium hexamethyldisilazane preferably lithium diisopropylamide. Suitable solvents include tetrahydrofuran, ether or dimethoxyethane, preferably tetrahydrofuran. The aforesaid reaction is run at a temperature of about −78° C. to about 0° C., preferably −78° C., for about 30 minutes to about 24 hours.

Alternatively, compounds of the formula XVIII, wherein P is as defined above, $R^3$ and $R^5$ are each hydrogen and $R^1$ and $R^8$ are as defined above, can be prepared from a compound of the formula XIX by reaction with a compound of the formula $R^8L$, wherein L is halo and $R^8$ are as defined above, and a base in a solvent. Suitable bases include lithium diisopropylamide, lithium hexamethyldisilazane, potassium hexamethyldisilazane, or sodium hexamethyldisilazane preferably lithium diisopropylamide. Suitable solvents include tetrahydrofuran, ether or dimethoxyethane, preferably tetrahydrofuran. The aforesaid reaction is run at a temperature of about −78° C. to about 0° C., preferably −78° C., for about 30 minutes to about 24 hours.

The compound of formula XIX, wherein P is as defined above, is prepared from a compound of the formula XX by reaction with a catalyst in an inert solvent in a manner analogous to that described by Ko, K-Y.; Lee, K-I; Kim, W-J *Tetrahedron Lett.*, 1992, 33, 6651. Suitable catalysts include rhodium acetate dimer or rhodium trifluoroacetate dimer, preferably rhodium acetate dimer. Suitable solvents include benzene, toluene or cyclohexane, preferably benzene. The aforesaid reaction is run at a temperature of about 20° C. to about 100° C., preferably at about 80° C., for a period of about 30 minutes to about 4 hours, preferably about 2 hours.

The compound of formula XX, wherein P is as defined above, is prepared from a compound of the formula XXI by reaction with a diazomethane reagent and a base in an inert solvent in a manner analogous to that described by Coutts, I. G. C.; Saint, R. E. *Tetrahedron Lett.*, 1998, 39, 3243. Suitable diazomethane reagents include trimethylsilyidiazomethane, preferably trimethylsilyldiazomethane. Suitable bases include n-butyllithium, preferably n-butyllithium. Suitable solvents include tetrahydrofuran or ether preferably ether. The aforesaid reaction is run at a temperature of about −100° C. for a period of 30 minutes to about 2 hours.

The compound of formula XXI, wherein P is 2-tert-butoxycarbonyl, is commercially available or can be made by methods well known to those of ordinary skill in the art.

Scheme 5 refers to a process for preparing compounds of the formula XXII. Compounds of the formula XXII are compounds of formula I wherein $R^1$, $R^2$, $R^3$, $R^5$, $R^6$, $R^7$ and $R^8$ are each hydrogen and $R^4$ is hydroxy, or wherein $R^1$, $R^2$, $R^4$, $R^5$, $R^6$, $R^7$ and $R^8$ are hydrogen, $R^3$ is as defined above and $R^4$ is hydroxy, or wherein $R^2$, $R^3$, $R^5$, $R^6$, $R^7$ and $R^8$ each hydrogen, $R^1$ is as defined above and $R^4$ is hydroxy, or wherein $R^1$, $R^2$, $R^3$, $R^6$, $R^7$ and $R^8$ are each hydrogen, $R^5$ is as defined above and $R^4$ is hydroxy.

Referring to Scheme 5, compounds of the formula XXII are prepared from compounds of the formula XXIII by reaction with a reducing agent and a catalyst in a reaction inert solvent. Suitable reducing agents include triethylammonium formate. Suitable catalysts include added Pd(0) reagents including tetrakistriphenylphosphine palladium, preferably tetrakistriphenylphosphine palladium. Suitable solvents include acetonitrile, acetonitrile-water or tetrahydrofuran-water, preferably acetonitrile-water. The aforesaid reaction is run at a temperature of about 0° C. to about 100° C., preferably at about 80° C., for a period of about 15 minutes to about 2 hours, preferably about 1 hour.

The compound of formula XXIII, wherein $R^1$, $R^3$ and $R^5$ are each hydrogen, are prepared from compounds of the formula XXIV by reaction with a reducing agent in an inert solvent. Suitable reducing agents include lithium borohydride, sodium borohydride, lithium aluminum hydride or soium cyanoborohydride, preferably lithium borohydride. Suitable solvents include tetrahydrofuran, dimethoxyethane or diethyl ether, preferably tetrahydrofuran. The aforesaid reaction is run at a temperature of about −10° C. to about 30° C., preferably at about 0° C., for a period of about 5 minutes to about 4 hours, preferably about 30 minutes.

Alternatively, compounds of the formula XXIII, wherein, $R^1$ and $R^5$ are each hydrogen and $R^3$ is as defined as above, can be prepared from a compound of the formula XXIV by reaction with a Grignard reagent of the formula $R^3$ MgL, wherein L is a halogen, in the presence of an organolanthanide salt in an inert solvent. Suitable organolanthanide salts include cerium (III) chloride. Suitable solvents include tetrahydrofuran. The aforesaid reaction is run at a temperature of about −50° C. to about 0° C. for about 1 minute to about 6 hours.

Alternatively, compounds of the formula XXIII, wherein $R^3$ and $R^5$ are each hydrogen and $R^1$ is as defined above, can be prepared from a compound of the formula XXIV by reaction with a compound of the formula $R^1L$, wherein L is halo and $R^5$ is as defined above, and a base in a solvent. Suitable bases include lithium diisopropylamide, lithium hexamethyldisilazane, potassium hexamethyldisilazane, or sodium hexamethyldisilazane preferably lithium diisopropylamide. Suitable solvents include tetrahydrofuran, ether or dimethoxyethane, preferably tetrahydrofuran. The aforesaid reaction is run at a temperature of about −78° C. to about 0° C., preferably −78° C., for about 30 minutes to about 24 hours.

Alternatively, compounds of the formula XXIII, wherein $R^1$ and $R^3$ are each hydrogen and $R^5$ is as defined above, can be prepared from a compound of the formula XXIV by reaction with a compound of the formula $R^5L$, wherein L is halo and $R^5$ is as defined above, and a base in a solvent. Suitable bases include lithium diisopropylamide, lithium hexamethyldisilazane, potassium hexamethyldisilazane, or sodium hexamethyldisilazane preferably lithium diisopropylamide. Suitable solvents include tetrahydrofuran, ether or dimethoxyethane, preferably tetrahydrofuran. The aforesaid reaction is run at a temperature of about −78° C. to about 0° C., preferably −78° C., for about 30 minutes to about 24 hours.

Compounds of the formula XXIV are prepared by oxidation from compounds of the formula XXV by reaction with a suitable Swern reagent or a chromium (VI) reagent such as pyridium chlorochromate, in the presence of a solvent. Suitable solvents include tetrahydrofuran or dichloromethane, preferably dichloromethane. The aforesaid reaction is run at a temperature of about 0° C. to about 40° C., preferably at about ambient temperature, for a period of about 10 minutes to about 2 hours.

Compounds of the formula XXV are prepared from compounds of the formula XXVI by reaction with O-allylhydroxylamine hydrochloride and a base, preferably in the presence of a solvent. One of ordinary skill in the art will understand that other hydroxylamines can be substituted for O-allylhydroxyl amine in analogous reactions. Suitable bases include trialkylamine bases such as diisopropylethylamine or triethylamine or pyridine bases such as pyridine, preferably the base is diisopropylethylamine. Suitable solvents include tetrahydrofuran or methylene chloride, preferably methylene chloride. The aforesaid reaction is performed at a temperature from about 0° C. to about 40° C., preferably about 23° C. The aforesaid reaction time ranges from about 2 hours to about 48 hours, preferably for about 2 to 4 hours.

Compounds of the formula XXVI can be prepared according to methods well known to those of ordinary skill in the art.

Scheme 6 refers to the preparation of compounds of the formula I. Compounds of the formula I can be prepared from compounds of the formula XXVII by methods analogous to those for the conversion of compounds of the formula XVII to formula XVI in Scheme 4 followed by the methods for the conversion of compounds of formula IV to formula I in Scheme 1.

Compounds of the formula XXVII, wherein one of $R^2$, $R^4$, $R^6$, and $R^8$ or $R^1$, $R^3$, $R^5$ and $R^7$ are hydrogen and the other of $R^2$, $R^4$, $R^6$ and $R^8$ or $R^1$, $R^3$ $R^5$ and $R^7$ are as defined above can be prepared from compounds of the formula XXVIII, by reaction with a reducing agent in a solvent. Suitable reducing agents include hydrogen in the presence of a catalyst such as palladium on carbon, rhodium on carbon, platinum oxide or palladium black, preferably rhodium on carbon. Suitable solvents include methanol, ethanol or water in the presence of either acid or base. The aforesaid reaction is performed at a temperature from about 0° C. to about 80° C., preferably about 23° C. under an atmosphere of hydrogen gas at a pressure ranging from atmospheric to 2000 psi. The aforesaid reaction time ranges from about 2 hours to about 48 hours.

Compounds of the formula XXVII, wherein $R^1$, $R^2$, $R^3$, $R^4$, $R^5$ $R^6$, $R^7$ and $R^8$ are as defined above, can be prepared from compounds of the formula XXVII, wherein $R^2$, $R^4$, $R^6$, and $R^8$ are hydrogen and $R^1$, $R^3$, $R^5$ and $R^7$ are as defined above, by methods well known to those of ordinary skill in the art. One example of such a preparation is the conversion of a compound of formula XXVII, wherein $R^3$ or $R^5$ is hydroxy to the corresponding keto derivative (e.g. Swern oxidation) followed by reaction of a Grignard reagent of the formula $R^4$ or $R^6$ MgL, wherein L is a halogen.

Compounds of the formula XXVIII are commercially available or can be made by methods well known to those of ordinary skill in the art.

Scheme 7 refers to a process of introducing different Q groups into compounds of the formula XXXI. Compounds of formula XXXI and XXIX are analogous compounds to those of formula II in Scheme 1, wherein P is a suitable protecting group analogous to those described for protecting hydroxyl groups as described in Greene and Wuts, "*Protecting Groups in Organic Synthesis*," (John Wiley & Son Press, 2nd Ed.). Compounds of the formula XXIX can be converted to compounds of the formula I according to the methods of Scheme 1.

Referring to Scheme 7, compounds of the formula XXIX can be prepared by treatment of a compound of the formula XXX with an optionally substituted $(C_6-C_{10})$aryl$(C_1-C_6)$ alkyl halide or $(C_2-C_9)$heteroaryl$(C_1-C_6)$alkyl halide (preferably a bromide or chloride) in the presence of a base in a polar solvent. Suitable bases include cesium carbonate or potassium carbonate, preferably cesium carbonate. Suitable solvents include dimethyl formamide or N-methyl-2-pyrrolidinone, preferably dimethyl formamide. The reaction mixture is stirred at a temperature from about 0° C. to about 60° C., preferably at about 40° C. for a period from about 30 minutes to about 24 hours, preferably about 1 hour.

The compound of formula XXX can be prepared from a compound of formula XXXI by reaction with a reducing agent in a polar solvent. Suitable reducing agents include hydrogen in the presence of a catalyst, such as palladium on carbon, Pearlman's catalyst, preferably palladium on carbon. The aforesaid reaction is run at a temperature of about 0° C. to about 30° C., preferably about 20° C. to about 25° C., for a period from about 4 hours to about 24 hours, preferably about 12 hours under a hydrogen atmosphere (35 psi).

The compound of formula XXXI is analogous to the compound of formula II from Scheme 1, wherein the allyl protected hydroxamate is replaced with a stable to reduction protected hydroxamate, specifically wherein P is a suitable protecting group analogous to those described for protecting hydroxyl groups as described in Greene and Wuts, "*Protecting Groups in Organic Synthesis*," (John Wiley & Son Press, 2nd Ed.). Optionally substituted $(C_6-C_{10})$aryl$(C_1-C_6)$ alkyl halide or $(C_2-C_9)$heteroaryl$(C_1-C_6)$alkyl halide (preferably a bromide or chloride) are commercially available or can be made by methods well known to those of ordinary skill in the art.

The ability of the compounds of formula I or their pharmaceutically acceptable salts (hereinafter also referred to as the compounds of the present invention) to inhibit metalloproteinases or mammalian reprolysin and, consequently, demonstrate their effectiveness for treating diseases characterized by metalloproteinase or the production of tumor necrosis factor is shown by the following in vitro assay tests.

Biological Assay

Inhibition of Soluble TNF-α Production

The ability of the compounds or the pharmaceutically acceptable salts thereof to inhibit the cellular release of TNF-α and, consequently, demonstrate their effectiveness for treating diseases involving the disregulation of soluble TNF-α is shown by the following in vitro assay:

Human Monocyte Assay

Human mononuclear cells were isolated from anti-coagulated human blood using a one-step Ficoll-hypaque separation technique. (2) The mononuclear cells were washed three times in Hanks balanced salt solution (HBSS) with divalent cations and resuspended to a density of $2 \times 10^6$/ml in HBSS containing 1% BSA. Differential counts determined using the Abbott Cell Dyn 3500 analyzer indicated that monocytes ranged from 17 to 24% of the total cells in these preparations.

180 m of the cell suspension was aliquoted into flat bottom 96 well plates (Costar). Additions of compounds and LPS (100 ng/ml final concentration) gave a final volume of 200 μl. All conditions were performed in triplicate. After a four hour incubation at 37° C. in an humidified $CO_2$ incubator, plates were removed and centrifuged (10 minutes at approximately 250×g) and the supernatants removed and assayed for TNF-α using the R&D ELISA Kit.

MMP Assays

Collagenase-3 (matrix metalloproteinase-13) selective inhibitors as used herein refer to agents which exhibit at least a 100 fold selectivity for the inhibition of collagenase-3 enzyme activity over collagenase-1 enzyme activity and a potency of less than 100 nM as defined by the $IC_{50}$ results from the MMP-13/MMP-1 fluorescence assays described below. Collagenase-3 selective inhibitors can be identified by screening the inhibitors of the present invention through the MMP-13/MMP-1 fluorescence assays described below and selecting those agents with MMP-13/MMP-1 inhibition $IC_{50}$ ratios of 100 or greater and potency of less than 100 nM.

Non-selective collagenase inhibitors as used herein refer to agents which exhibit less than a 100 fold selectivity for the inhibition of collagenase-3 enzyme activity over collagenase-1 enzyme activity or a potency of more than 100 nM as defined by the $IC_{50}$ results from the MMP-13/MMP-1 fluorescence assays described below.

The ability of collagenase inhibitors to inhibit collagenase activity is well known in the art. Many suitable proctols are known in the art for identifying MMP inhibitiors. The following assays may be used to identify matrix metalloproteinase inhibitors.

Inhibition of Human Collagenase (MMP-1)

Human recombinant collagenase is activated with trypsin using the following ratio: 10 μg trypsin per 100 μg of collagenase. The trypsin and collagenase are incubated at room temperature for 10 minutes then a five fold excess (50 μg/10 μg trypsin) of soybean trypsin inhibitor is added.

10 mM stock solutions of inhibitors are made up in dimethyl sulfoxide and then diluted using the following Scheme:

10 mM→120 μM→12 μM→1.2 μM→0.12 μM

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) are set up in wells D1–D6 and blanks (no enzyme, no inhibitors) are set in wells D7–D12.

Collagenase is diluted to 400 ng/ml and 25 μl is then added to appropriate wells of the microfluor plate. Final concentration of collagenase in the assay is 100 ng/ml.

Substrate (DNP-Pro-Cha-Gly-Cys(Me)-His-Ala-Lys (NMA)-$NH_2$) is made as a 5 mM stock in dimethyl sulfoxide and then diluted to 20 mM in assay buffer. The assay is initiated by the addition of 50 μl substrate per well of the microfluor plate to give a final concentration of 10 μM.

Fluorescence readings (360 nM excitation, 460 nm emission) were taken at time 0 and then at 20 minute intervals. The assay is conducted at room temperature with a typical assay time of 3 hours.

Fluorescence vs time is then plotted for both the blank and collagenase containing samples (data from triplicate determinations is averaged). A time point that provides a good signal (the blank) and that is on a linear part of the curve (usually around 120 minutes) is chosen to determine $IC_{50}$ values. The zero time is used as a blank for each compound at each concentration and these values are subtracted from the 120 minute data. Data is plotted as inhibitor concentration vs % control (inhibitor fluorescence divided by fluorescence of collagenase alone×100). $IC_{50}$'s are determined from the concentration of inhibitor that gives a signal that is 50% of the control.

If $IC_{50}$'s are reported to be <0.03 μM then the inhibitors are assayed at concentrations of 0.3 μM, 0.03 μM, 0.03 μM and 0.003 μM.

Inhibition of Gelatinase (MMP-2)

Inhibition of gelatinase activity is assayed using the Dnp-Pro-Cha-Gly-Cys(Me)-His-Ala-Lys(NMA)-$NH_2$ substrate (10 μM) under the same conditions as inhibition of human collagenase (MMP-1).

72 kD gelatinase is activated with 1 mM APMA (p-aminophenyl mercuric acetate) for 15 hours at 4° C. and is diluted to give a final concentration in the assay of 100 mg/ml. Inhibitors are diluted as for inhibition of human collagenase (MMP-1) to give final concentrations in the assay of 30 μM, 3 μM, 0.3 μM and 0.03 μM. Each concentration is done in triplicate.

Fluorescence readings (360 nm excitation, 460 emission) are taken at time zero and then at 20 minutes intervals for 4 hours.

$IC_{50}$'s are determined as per inhibition of human collagenase (MMP-1). If $IC_{50}$'s are reported to be less than 0.03 μM, then the inhibitors are assayed at final concentrations of 0.3 μM, 0.03 μM, 0.003 μM and 0.003 μM.

Inhibition of Stromelysin Activity (MMP-3)

Inhibition of stromelysin activity is based on a modified spectrophotometric assay described by Weingarten and Feder (Weingarten, H. and Feder, J., Spectrophotometric Assay for Vertebrate Collagenase, Anal. Biochem. 147, 437–440 (1985)). Hydrolysis of the thio peptolide substrate [Ac-Pro-Leu-Gly-SCH[$CH_2CH(CH_3)_2$]CO-Leu-Gly-$OC_2H_5$] yields a mercaptan fragment that can be monitored in the presence of Ellman's reagent.

Human recombinant prostromelysin is activated with trypsin using a ratio of 1 μl of a 10 mg/ml trypsin stock per 26 mg of stromelysin. The trypsin and stromelysin are incubated at 37° C. for 15 minutes followed by 10 μl of 10 μg/ml soybean trypsin inhibitor for 10 minutes at 37° C. for 10 minutes at 37° C. to quench trypsin activity.

Assays are conducted in a total volume of 250 ml of assay buffer (200 mM sodium chloride, 50 mM MES, and 10 mM calcium chloride, pH 6.0) in 96-well microliter plates. Activated stromelysin is diluted in assay buffer to 25 μg/ml. Ellman's reagent (3-Carboxy-4-nitrophenyl disulfide) is made as a 1M stock in dimethyl formamide and diluted to 5 mM in assay buffer with 50 ml per well yielding at 1 mM final concentration.

10 mM stock solutions of inhibitors are made in dimethyl sulfoxide and diluted serially in assay buffer such that addition of 50 μL to the appropriate wells yields final concentrations of 3 μM, 0.3 μM, 0.003 μM, and 0.0003 μM. All conditions are completed in triplicate.

A 300 mM dimethyl sulfoxide stock solution of the peptide substrate is diluted to 15 mM in assay buffer and the assay is initiated by addition of 50 μl to each well to give a final concentration of 3 mM substrate. Blanks consist of the peptide substrate and Ellman's reagent without the enzyme. Product formation was monitored at 405 nm with a Molecular Devices UVmax plate reader.

$IC_{50}$ values were determined in the same manner as for collagenase.

Inhibition of MMP-13

Human recombinant MMP-13 is activated with 2 mM APMA (p-aminophenyl mercuric acetate) for 1.5 hours, at 37° C. and is diluted to 400 mg/ml in assay buffer (50 mM Tris, pH 7.5, 200 mM sodium chloride, 5 mM calcium chloride, 20 $\mu$M zinc chloride, 0.02% brij). Twenty-five microliters of diluted enzyme is added per well of a 96 well microfluor plate. The enzyme is then diluted in a 1:4 ratio in the assay by the addition of inhibitor and substrate to give a final concentration in the assay of 100 mg/ml.

10 mM stock solutions of inhibitors are made up in dimethyl sulfoxide and then diluted in assay buffer as per the inhibitor dilution scheme for inhibition of human collagenase (MMP-1): Twenty-five microliters of each concentration is added in triplicate to the microfluor plate. The final concentrations in the assay are 30 $\mu$M, 3 $\mu$M, 0.3 $\mu$M, and 0.03 $\mu$M.

Substrate (Dnp-Pro-Cha-Gly-Cys(Me)-His-Ala-Lys (NMA)-$NH_2$) is prepared as for inhibition of human collagenase (MMP-1) and 50 ml is added to each well to give a final assay concentration of 10 $\mu$M. Fluorescence readings (360 nM excitation; 450 emission) are taken at time 0 and every 5 minutes for 1 hour.

Positive controls consist of enzyme and substrate with no inhibitor and blanks consist of substrate only.

$IC_{50}$'s are determined as per inhibition of human collagenase (MMP-1). If $IC_{50}$'s are reported to be less than 0.03 $\mu$M, inhibitors are then assayed at final concentrations of 0.3 $\mu$M, 0.03 $\mu$M, 0.003 $\mu$M and 0.0003 $\mu$M.

Collagen film MMP-13 Assay

Rat type I collagen is radiolabeled with $^{14}C$ acetic anhydride (T. E. Cawston and A. J. Barrett, *Anal. Biochem.*, 99, 340–345 (1979)) and used to prepare 96 well plates containing radiolabeled collagen films (Barbara Johnson-Wint, *Anal. Biochem.*, 104, 175–181 (1980)). When a solution containing collagenase is added to the well, the enzyme cleaves the insoluble collagen which unwinds and is thus solubilized. Collagenase activity is directly proportional to the amount of collagen solubilized, determined by the proportion of radioactivity released into the supernatant as measured in a standard scintillation counter. Collagenase inhibitors are, therefore, compounds which reduce the radioactive counts released with respect to the controls with no inhibitor present. One specific embodiment of this assay is described in detail below.

For determining the selectivity of compounds for MMP-13 versus MMP-1 using collagen as a substrate, the following procedure is used. Recombinant human proMMP-13 or proMMP-1 is activated according to the procedures outlined above. The activated MMP-13 or MMP-1 is diluted to 0.6 ug/ml with buffer (50 mM Tris pH 7.5, 150 mM NaCl, 10 mM $CaCl_2$, 1 $\mu$M $ZnCl_2$, 0.05% Brij-35, 0.02% sodium azide).

Stock solutions of test compound (10 mM) in dimethylsulfoxide are prepared. Dilutions of the test compounds in the Tris buffer, above, are made to 0.2, 2.0, 20, 200, 2000 and 20000 nM.

100 $\mu$l of appropriate drug dilution and 100 $\mu$l of diluted enzyme are pipetted into wells of a 96 well plate containing collagen films labeled with $^{14}C$-collagen. The final enzyme concentration is 0.3 $\mu$g/ml while the final drug concentration is 0.1, 1.0, 10, 100, 1000 nM. Each drug concentration and control is analyzed in triplicate. Triplicate controls are also run for the conditions in which no enzyme is present and for enzyme in the absence of any compound.

The plates are incubated at 37° C. for a time period such that around 30–50% of the available collagen is solubilized—determined by counting additional control wells at various time points. In most cases around 9 hours of incubation are required. When the assay has progressed sufficiently, the supernatant from each well is removed and counted in a scintillation counter. The background counts (determined by the counts in the wells with no enzyme) are subtracted from each sample and the % release calculated in relation to the wells with enzyme only and no inhibitor. The triplicate values for each point are averaged and the data graphed as percent release versus drug concentration. $IC_{50}$'s are determined from the point at which 50% inhibition of release of radiolabeled collagen is obtained.

To determine the identity of the active collagenases in cartilage conditioned medium, assays were carried out using collagen as a substrate, cartilage conditioned medium containing collagenase activity and inhibitors of varying selectivity. The cartilage conditioned medium was collected during the time at which collagen degradation was occurring and thus is representative of the collagenases responsible for the collagen breakdown. Assays were carried out as outlined above except that instead of using recombinant MMP-13 or recombinant MMP-1, cartilage conditioned medium was the enzyme source.

IL-1 Induced Cartilage Collagen Degradation From Bovine Nasal Cartilage

This assay uses bovine nasal cartilage explants which are commonly used to test the efficacy of various compounds to inhibit either IL-1 induced proteoglycan degradation or IL-1 induced collagen degradation. Bovine nasal cartilage is a tissue that is very similar to articular cartilage, i.e. chondrocytes surrounded by a matrix that is primarily type II collagen and aggrecan. The tissue is used because it: (1) is very similar to articular cartilage, (2) is readily available, (3) is relatively homogeneous, and (4) degrades with predictable kinetics after IL-1 stimulation.

Two variations of this assay have been used to assay compounds. Both variations give similar data. The two variations are described below:

Variation 1

Three plugs of bovine nasal cartilage (approximately 2 mm diameter×1.5 mm long) are placed into each well of a 24 well tissue culture plate. One ml of serumless medium is then added to each well. Compounds are prepared as 10 mM stock solutions in DMSO and then diluted appropriately in serumless medium to final concentrations, eg., 50, 500 and 5000 nM. Each concentration is assayed in triplicate.

Human recombinant IL-1α (5 ng/mL) (IL-1) is added to triplicate control wells and to each well containing drug. Triplicate control wells are also set up in which neither drug nor IL-1 are added. The medium is removed and fresh medium containing IL-1 and the appropriate drug concentrations is added on days 6, 12, 18 and 24 or every 3–4 days if necessary. The media removed at each time point is stored at −20° C. for later analysis. When the cartilage in the IL-1 alone wells has almost completely resorbed (about day 21), the experiment is terminated. The medium, is removed and stored. Aliquots (100 μl) from each well at each time point are pooled, digested with papain and then analyzed for hydroxyproline content. Background hydroxyproline (average of wells with no IL-1 and no drug) is subtracted from each data point and the average calculated for each triplicate. The data is then expressed as a percent of the IL-1 alone average value and plotted. The $IC_{50}$ is determined from this plot.

Variation 2

The experimental set-up is the same as outlined above in Variation 1, until day 12. On day 12, the conditioned medium from each well is removed and frozen. Then one ml of phosphate buffered saline (PBS) containing 0.5 μg/ml trypsin is added to each well and incubation continued for a further 48 hours at 37° C. After 48 hours incubation in trypsin, the PBS solution is removed. Aliquots (50 μl) of the PBS/trypsin solution and the previous two time points (days 6 and 12) are pooled, hydrolyzed and hydroxyproline content determined. Background hydroxyproline (average of wells with no IL-1 and no drug) is subtracted from each data point and the average calculated for each triplicate. The data is then expressed as a percent of the IL-1 alone average value and plotted. The $IC_{50}$ is determined from this plot. In this variation, the time course of the experiment is shortened considerably. The addition of trypsin for 48 hours after 12 days of IL-1 stimulation likely releases any type II collagen that has been damaged by collagenase activity but not yet released from the cartilage matrix. In the absence of IL-1 stimulation, trypsin treatment produces only low background levels of collagen degradation in the cartilage explants.

Inhibition of Human 92 kD Gelatinase (MMP-9)

Inhibition of 92 kD gelatinase (MMP-9) activity is assayed using the Mca-Pro-Leu-Gly-Leu-Dpa-Ala-Arg-$NH_2$ substrate (10 μM) under similar conditions as described above for the inhibition of human collagenase (MMP-1).

Human recombinant 92 kD gelatinase (MMP-9, gelatinase B) is activated for 2 hours with 1 mM p-aminophenyl-mercuric acetate (from a freshly prepared 100 mM stock in 0.2 N NaOH) at 37° C.

10 mM dimethylsulfoxide stock solutions of inhibitors are diluted serially in assay buffer (50 mM TRIS, pH 7.5, 200 mM NaCl, 5 mM $CaCl_2$, 20 μM $ZnCl_2$, 0.02% BRIJ-35 (vol./vol.)) using the following scheme:

10 mM→120 μM→12 μM→1.2 μM→0.12 μM

Further dilutions are made as necessary following this same scheme. A minimum of four inhibitor concentrations for each compound are performed in each assay. 25 μL of each concentration is then added to triplicate wells of a black 96 well U-bottomed microfluor plate. As the final assay volume is 100 μL, final concentrations of inhibitor are the result of a further 1:4 dilution (i.e. 30 μM→3 μM→0.3 μM→0.03 μM, etc.). A blank (no enzyme, no inhibitor) and a positive enzyme control (with enzyme, no inhibitor) are also prepared in triplicate.

Activated enzyme is diluted to 100 ng/mL in assay buffer, 25 μL per well is added to appropriate wells of the microplate. Final enzyme concentration in the assay is 25 ng/mL (0.27 nM).

A five mM dimethylsulfoxide stock solution of substrate (Mca-Pro-Leu-Gly-Leu-Dpa-Ala-Arg-$NH_2$) is diluted in assay buffer to 20 μM. The assay is initiated by addition of 50 μL of diluted substrate yielding a final assay concentration of 10 μM substrate. A 0 time fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for $IC_{50}$ determinations. The 0 time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. $IC_{50}$'s are defined as the concentration of inhibitor that gives a signal that is 50% of the positive enzyme control.

Aggrecanase Assay

Primary porcine chondrocytes from articular joint cartilage are isolated by sequential trypsin and collagenase digestion followed by collagenase digestion overnight and are plated at $2 \times 10^5$ cells per well into 48 well plates with 5 μCi/ml $^{35}$S (1000 Ci/mmol) sulphur in type I collagen coated plates. Cells are allowed to incorporate label into their proteoglycan matrix (approximately 1 week) at 37° C., under an atmosphere of 5% $CO_2$.

The night before initiating the assay, chondrocyte monolayers are washed two times in DMEM/1% PSF/G and then allowed to incubate in fresh DMEM/1% FBS overnight.

The following morning chondrocytes are washed once in DMEM/1%PSF/G. The final wash is allowed to sit on the plates in the incubator while making dilutions.

Media and dilutions can be made as described in the Table below.

| | |
|---|---|
| Control Media | DMEM alone (control media) |
| IL-1 Media | DMEM + IL-1 (5 ng/ml) |
| Drug Dilutions | Make all compounds stocks at 10 mM in DMSO. Make a 100 uM stock of each compound in DMEM in 96 well plate. Store in freezer overnight. The next day perform serial dilutions in DMEM with IL-1 to 5 μM, 500 nM, and 50 nM. Aspirate final wash from wells and add 50 ul of compound from above dilutions to 450 ul of IL-1 media in appropriate wells of the 48 well plates. Final compound concentrations equal 500 nM, 50 nM, and 5 nM. All samples completed in triplicate with Control and IL-1 alone samples on each plate. |

Plates are labeled and only the interior 24 wells of the plate are used. On one of the plates, several columns are designated as IL-1 (no drug) and Control (no IL-1, no drug). These control columns are periodically counted to monitor 35S-proteoglycan release. Control and IL-1 media are added to wells (450 ul) followed by compound (50 ul) so as to initiate the assay. Plates are incubated at 37° C., with a 5% $CO_2$ atmosphere.

At 40–50% release (when CPM from IL-1 media is 4–5 times control media) as assessed by liquid scintillation counting (LSC) of media samples, the assay is terminated (9–12 hours). Media is removed from all wells and placed in scintillation tubes. Scintillate is added and radioactive counts are acquired (LSC). To solubilize cell layers, 500 ul of papain digestion buffer (0.2 M Tris, pH 7.0, 5 mM EDTA, 5 mM DTT, and 1 mg/ml papain) is added to each well. Plates with digestion solution are incubated at 60° C. overnight. The cell layer is removed from the plates the next day and placed in scintillation tubes. Scintillate is then added, and samples counted (LSC).

The percent of released counts from the total present in each well is determined. Averages of the triplicates are made with control background subtracted from each well. The percent of compound inhibition is based on IL-1 samples as 0% inhibition (100% of total counts).

The compounds of the present invention that were tested had $IC_{50}$ of less than 1 $\mu$M, preferably less than 50 nM in at least one of the assays described above. Most preferred compounds of the invention are at least 100 fold less potent against r-MMP-1 than against TACE in the above assay.

For administration to mammals, including humans, for the inhibition of matrix metalloproteinases or mammalian reprolysin, a variety of conventional routes may be used including orally, parenterally buccally, rectally and topically. In general, the active compound will be administered orally or parenterally at dosages between about 0.1 and 25 mg/kg body weight of the subject to be treated per day, preferably from about 0.3 to 5 mg/kg. However, some variation in dosage will necessarily occur depending on the condition of the subject being treated. The person responsible for administration will, in any event, determine the appropriate dose for the individual subject.

The compounds of the present invention can be administered in a wide variety of different dosage forms, in general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

The following Examples illustrate the preparation of the compounds of the present invention. Melting points are uncorrected. NMR data are reported in parts per million ($\delta$) and are referenced to the deuterium lock signal from the sample solvent (deuteriodimethylsulfoxide unless otherwise specified). Commercial reagents were utilized without further purification. THF refers to tetrahydrofuran. DMF refers to N,N-dimethylformamide. Chromatography refers to column chromatography performed using 32–63 mm silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure means that a rotary evaporator was used.

EXAMPLE 1

(2R,5R)-1-[4-(2,5-DIFLUORO-BENZYLOXY)-BENZENESULFONYL]-5-HYDROXY-PIPERIDINE-2-CARBOXYLIC ACID HYDROXYAMIDE 2-tert-Butoxycarbonylamino-5-diazo-4-oxo-pentanoic acid methyl ester To a solution of trimethylsilyidiazomethane (1.24 mL of a 2M solution in hexane, 2.5 mmol) in 12 mL of tetrahydrofuran at −100° C. was added n-butyllithium (1.01 mL of a 2.5 M solution in hexane, 2.5 mmol). After stirring for 30 min, the solution was transferred via an insulated cannula to a −100° C. solution of N-BOC (D)-pyroglutamic acid methyl ester (0.50 g, 2.1 mmol) in 21 mL of tetrahydrofuran. After stirring for 20 min, the mixture was poured into saturated aqueous $NH_4Cl$, extracted twice with ethyl acetate, and the combined organic layers were dried over $Na_2SO_4$, filtered and concentrated, affording 0.62 g of 2-tert-butoxycarbonylamino-5-diazo-4-oxo-pentanoic acid methyl ester as a yellow oil.

4-Oxo-piperidine-1,2-dicarboxylic acid 1-tert-butyl ester 2-methyl ester

To a refluxing mixture of rhodium acetate dimer (0.0093 g, 0.02 mmol) and 40 mL of benzene was added dropwise a solution of 2-tert-butoxycarbonylamino-5-diazo-4-oxo-pentanoic acid methyl ester (0.60 g, 2.1 mmol) in 4.5 mL of benzene. After stirring for 2 h at reflux, the mixture was cooled to room temperature, concentrated in vacuo, and filtered through a small pad of silica gel eluting with 1:1 ethyl acetate-hexane. Concentration of the filtrate afforded 0.53 g of 4-oxo-piperidine-1,2-dicarboxylic acid 1-tert-butyl ester 2-methyl ester as a yellow oil.

5-(4-Benzyloxy-benzenesulfonyl)-2-oxa-5-aza-bicyclo[2.2.2]octan-3-one

To a solution of 4-oxo-piperidine-1,2-dicarboxylic acid 1-tert-butyl ester 2-methyl ester (1.1 g, 3.9 mmol) in 20 mL of methanol was added sodium borohydride (0.14 9, 3.9 mmol) at 0° C. After stirring for 2 h at 0° C., the mixture was diluted with ethyl acetate, washed with 1M HCl, 1M NaOH, and brine, dried over $Na_2SO_4$, filtered and concentrated. The residue was taken up in 10 mL of 6M aqueous HCl and was refluxed for 4 h. After cooling to room temperature, the mixture was concentrated in vacuo, and the residue was dissolved in 5.5 mL of anhydrous DMF. The solution was cooled to 0° C. and was treated with triethylamine (4.8 mL, 34 mmol) and 4-benzyloxy-benzenesulfonyl chloride (2.5 g, 8.8 mmol). After stirring for 2 h, the mixture was diluted with 1M HCl, extracted 3× with ethyl acetate, and the organic layers were dried over $Na_2SO_4$, filtered and concentrated in vacuo. The residue was filtered through a small pad of silica gel eluting with 1:1 ethyl acetate-hexane, affording 0.43 g of 5-(4-benzyloxy-benzenesulfonyl)-2-oxa-5-aza-bicyclo[2.2.2]octan-3one as a colorless solid.

5-(4-Hydroxy-benzenesulfonyl)-2-oxa-5-aza-bicyclo[2.2.2]octan-3-one

A mixture of 5-(4-benzyloxy-benzenesulfonyl)-2-oxa-5-aza-bicyclo[2.2.2]octan-3-one (1.0 g, 2.7 mmol), ethyl acetate-methanol (1:1, 100 mL) and 10% Pd on charcoal (0.22 g) was shaken under 50 psi of hydrogen for 1.5 h. Filtration through a pad of Celite and concentration of the filtrate in vacuo afforded 0.80 g of 5-(4-hydroxy-benzenesulfonyl)-2-oxa-5-aza-bicyclo[2.2.2]octan-3-one as a colorless solid.

5-[4-(2,5-difluoro-benzyloxy)-benzenesulfonyl]-2-oxa-5-aza-bicyclo[2.2.2]octan-3-one General Procedure for the Alkylation of 5-(4-Hydroxy-benzenesulfonyl)-2-oxa-5-aza-bicyclo[2.2.2]octan-3-one A mixture of 5-(4-hydroxy-benzenesulfonyl)-2-oxa-5-aza-bicyclo[2.2.2]octan-3-one (0.10 g, 0.35 mmol), the appropriate alkyl halide (0.72 mmol), potassium carbonate (0.10 g, 0.72 mmol) and DMF (0.6 mL) was shaken at 50° C. for 18 h. The mixture was diluted with water, extracted 3× into ethyl acetate and the combined organic layers were dried over $Na_2SO_4$, filtered and concentrated. Purification by radial chromatography (1:1 ethyl acetate-hexane, 2 mm silica gel plate) afforded the lactone intermediate as a colorless solid or oil.

Following the above general procedure for the alkylation of 5-(4-hydroxy-benzenesulfonyl)-2-oxa-5-aza-bicyclo [2.2.2]octan-3-one using 3,5-difluorobenzyl bromide as the alkyl bromide afforded 61 mg of 5-[4-(2,5-difluoro-benzyloxy)-benzenesulfonyl]-2-oxa-5-aza-bicyclo[2.2.2] octan-3-one as a colorless solid:

1-[4-(2,5-Difluoro-benzyloxy)-benzenesulfonyl]-5-hydroxy-piperidine-2-carboxylic acid hydroxyamide General Procedure for the Formation of 5-Hydroxy Pipecolate Hydroxamic Acids The lactone was dissolved in 0.8 mL of 0.8 M hydroxylamine in methanol (prepared by the addition of 1 equiv. of hydroxylamine hydrochloride to 1 equiv. of sodium methoxide in methanol), and the resulting suspension was shaken at 60° C. for 20 min. After cooling to room temperature, the mixture was acidified with 1M HCl, extracted 3× into ethyl acetate, and the combined organic layers were washed 3× with 50% saturated aqueous $NaHCO_3$, 1× with pH 7.0 phosphate buffer (1M), dried over $Na_2SO_4$, filtered and concentrated. Trituration of the residue from methylene chloride-hexane afforded the hydroxamic acid as a colorless solid.

The lactone from the previous step was converted to the hydrxamic acid following the general procedure listed above, affording 0.021 g of 1-[4-(2,5-Difluoro-benzyloxy)-benzenesulfonyl]-5-hydroxy-piperidine-2-carboxylic acid hydroxyamide as a colorless solid:

EXAMPLE 2

(2R,5R)-1-(4-BENZYLOXY-BENZENESULFONYL)-5-HYDROXY-5-METHYL-PIPERIDINE-2-CARBOXYLIC ACID HYDROXYAMIDE

5-Hydroxy-5-methyl-piperidine-1,2-dicarboxylic acid 1-tert-butyl ester 2-methyl ester Cerium chloride (0.21 g, 0.86 mmol) was dried in vacuo at 90° C. for 1 hour, then at 140° C. for 1.5 hours. After cooling to room temperature, 2.8 mL of THF was added, and the suspension was stirred for 1 hour. 5-Oxo-piperidine-1,2-dicarboxylic acid 1-tert-butyl ester 2-methyl ester (0.10 g, 0.39 mmol) was added, and the mixture was stirred at 0° C. for 2 hour. Methyl magnesium bromide (0.14 mL of a 3M solution in ether) was added dropwise at −50° C, and the mixture was immediately warmed to room temperature and stirred for 30 minutes. Additional methyl magnesium bromide was added following the preceeding procedure until the reaction was complete as determined by $^1$H NMR of an aliquot worked up as described below. The mixture was diluted with saturated aqueous $NH_4Cl$, extracted 3 times with ethyl acetate, and the combined organic layers were dried over $Na_2SO_4$, filtered and concentrated, affording ca. 0.08 g of crude 5-hydroxy-5-methyl-piperidine-1,2-dicarboxylic acid 1-tert-butyl ester 2-methyl ester as a colorless oil.

1-(4-Benzyloxy-benzenesulfonyl)-5-hydroxy-5-methyl-piperidine-2-carboxylic acid methyl ester To a mixture of 5-hydroxy-5-methyl-piperidine-1,2-dicarboxylic acid 1-tert-butyl ester 2-methyl ester (0.08 g) and 5 mL of methanol was added 10 drops of 12 M aqueous HCl. After stirring for 1 hour, the mixture was concentrated in vacuo, and the residue was dissolved in 1 mL of DMF. After cooling to 0° C., the mixture was treated with triethylamine (0.11 mL, 0.80 mmol) and 4-benzyloxy-benzenesulfonyl chloride (0.11 g, 0.40 mmol). After stirring for 2 h at room temperature, the mixture was diluted with ethyl acetate, washed 2× with 1M HCl, dried over $Na_2SO_4$, filtered and concentrated in vacuo. The residue was purified by radial chromatography (2:1 hexane-ethyl acetate, 2 mm silica gel plate) affording 0.047 g of 1-(4-benzyloxy-benzenesulfonyl)-5-hydroxy-5-methyl-piperidine-2-carboxylic acid methyl ester as a colorless solid.

5-(4-Benzyloxy-benzenesulfonyl)-1-methyl-2-oxa-5-aza-bicyclo[2.2.2]octan-3-one

A mixture of 1-(4-benzyloxy-benzenesulfonyl)-5-hydroxy-5-methyl-piperidine-2-carboxylic acid methyl ester (0.047 g, 0.11 mmol), p-toluenesulfonic acid (0.010 g, 0.05 mmol) and toluene (2.0 mL) was heated to 90° C. for 2 h. After cooling to room temperature, the mixture was diluted with ethyl acetate, washed with saturated aqueous NaHCO$_3$, dried over Na$_2$SO$_4$, filtered and concentrated in vacuo, giving 0.035 g of 5-(4-Benzyloxy-benzenesulfonyl)-1-methyl-2-oxa-5-aza-bicyclo[2.2.2]octan-3-one as a colorless oil:

1-(4-Benzyloxy-benzenesulfonyl)-5-hydroxy-5-methyl-piperidine-2-carboxylic acid hydroxyamide 5-(4-Benzyloxy-benzenesulfonyl)-1-methyl-2-oxa-5-aza-bicyclo[2.2.2]octan-3-one (0.035 g, 0.09 mmol) was dissolved in 0.80 mL of a 0.81 M solution of hydroxylamine in methanol (prepared by treating 7.25 mL of a 0.81 M solution of sodium methoxide in methanol with 0.52 g of hydroxylamine hydrochloride). The resulting mixture was shaken at 60° C. for 10 minutes. After cooling to room temperature, the mixture was diluted with 1M HCl, extracted twice with ethyl acetate, and the combined organic layers were washed twice with 50% saturated aqueous NaHCO$_3$, once with 1M pH 7.0 phosphate buffer, dried over Na$_2$SO$_4$, filtered and concentrated in vacuo. Trituration of the residue with CH$_2$Cl$_2$-hexane afforded 0.027 g of 1-(4-benzyloxy-benzenesulfonyl)-5-hydroxy-5-methyl-piperidine-2-carboxylic acid hydroxyamide as a colorless solid:

EXAMPLE 3

1-(4-BENZYLOXY-BENZENESULFONYL)-5-METHOXY-PIPERIDINE-2-CARBOXYLIC ACID HYDROXYAMIDE 1-(4-Benzyloxy-benzenesulfonyl)-5-hydroxy-piperidine-2-carboxylic acid To a mixture of 5-(4-benzyloxy-benzenesulfonyl)-2-oxa-5-aza-bicyclo[2.2.2]octan-3-one (0.10 g, 0.26 mmol) and 2 mL of THF was added 0.2 mL of 1M aqueous HCl. After stirring for 10 min, 0.15 mL of 12M aqueous HCL was added. After stirring for 30 min, TLC indicated no detectable reaction. The mixture was then treated with 2 mL of saturated aqueous LiOH and 2 mL of methanol. After stirring for 20 min at room temperature, the mixture was acidified with 1M HCl, extracted 3× into ethyl acetate, and the combined organic layers were dried over Na$_2$SO$_4$, filtered and concentrated in vacuo, affording 1-(4-benzyloxy-benzenesulfonyl)-5-hydroxy-piperidine-2-carboxylic acid (0.10 g) as a colorless syrup:

1-(4-Benzyloxy-benzenesulfonyl)-5-methoxy-piperidine-2-carboxylic acid

A mixture of 1-(4-benzyloxy-benzenesulfonyl)-5-hydroxy-piperidine-2-carboxylic acid (0.10 g, 0.26 mmol) and 1:1 THF-N-methylpyrrolidin-2-one (1 mL) was treated with NaH (0.031 g, 0.78 mmol, 60% dispersion in mineral oil). After stirring for 10 min, the mixture was warmed to room temperature, stirred for 20 min and treated with iodomethane (0.016 mL, 0.26 mmol). After stirring fro 3 h, the mixture was treated with an additional 0.010 g of NaH and 0.015 mL of iodomethane. The resulting mixture was stirred for 24 h, acidified with 1M HCl, extracted 3× with ethyl acetate, and the combined organic layers were dried over Na$_2$SO$_4$, filtered and concentrated in vacuo. Purification of the residue by radial chromatography (1:1 to 2:1 ethyl acetate hexane containing 1% of acetic acid, 2 mm silica gel plate) afforded 0.077 g (75%) of 1-(4-benzyloxy-benzenesulfonyl)-5-methoxy-piperidine-2-carboxylic acid as a colorless syrup:

1-(4-Benzyloxy-benzenesulfonyl)-5-methoxy-piperidine-2-carboxylic acid allyloxy-amide A solution of 1-(4-benzyloxy-benzenesulfonyl)-5-methoxy-piperidine-2-carboxylic acid (0.077 g, 0.19 mmol), HOBT (0.044 g, 0.29 mmol), O-allylhydroxylamine hydrochloride (0.043 g, 0.29 mmol), di-isopropylethylamine (0.066 mL, 0.38 mmol) and CH$_2$Cl$_2$ (2 mL) was treated with EDCl (0.056 g, 0.29 mmol). After stirring for 24 h at room temperature, the mixture was diluted with ethyl acetate, washed with 1M HCl, saturated aqueous NaHCO$_3$, dried over Na$_2$SO$_4$, filtered and concentrated in vacuo, affording 1-(4-benzyloxy-benzenesulfonyl)-5-methoxy-piperidine-2-carboxylic acid allyloxy-amide (0.090 g, 100%) as a colorless syrup:

1-(4-Benzyloxy-benzenesulfonyl)-5-methoxy-piperidine-2-carboxylic acid hydroxyamide To a solution of 1-(4-benzyloxy-benzenesulfonyl)-5-methoxy-piperidine-2-carboxylic acid allyloxy-amide (0.090 g, 0.20 mmol), triethylammonium formate (0.28 mL of a 3M solution in water, 0.83 mmol) and acetonitrile (1.1 mL) was added tetrakistriphenylphosphine palladium. After stirring for 15 min at 80° C., the mixture was cooled to room temperature and concentrated in vacuo. The residue was diluted with ether and extracted 2× into 1 M NaOH. The combined aqueous layers were washed 2× with ether, acidified with 1M HCl and extracted 3× with ethyl acetate. The combined organic layers were dried over Na$_2$SO$_4$, filtered and concentrated. Purification of the residue by silica gel chromatography eluting with ethyl acetate afforded 0.025 g of 1-(4-benzyloxy-benzenesulfonyl)-5-methoxy-piperidine-2-carboxylic acid hydroxyamide as a yellow solid after trituration from CH$_2$Cl$_2$-hexane:

EXAMPLE 4

1-[4-(4-FLUORO-BENZYLOXY)-BENZENESULFONYL]-3-HYDROXY-3-METHYL-PIPERIDINE-2-CARBOXYLIC ACID HYDROXYAMIDE

[4-(4-Fluoro-benzyloxy)-benzenesulfonylamino]-acetic acid tert-butyl ester

To a mixture of glycine tert butyl ester hydrochloride salt (5.9 g, 18 mmol) and DMF (20 mL) at 0° C. was added triethylamine (6.5 mL, 45 mmol) and 4-(4-fluoro-benzyloxy)-benzenesulfonyl chloride. After stirring for 1 h, the mixture was warmed to room temperature and stirred for an additional hour. The mixture was diluted with ethyl acetate, washed with 1M HCl, saturated aqueous NaHCO$_3$ and brine, dried over Na$_2$SO$_4$, filtered and concentrated in vacuo. Trituration of the residue with ether-hexane afforded 10.8 g of [4-(4-fluoro-benzyloxy)-benzenesulfonylamino]-acetic acid tert-butyl ester as colorless crystals.

2-[4-(4-Fluoro-benzyloxy)-benzenesulfonylamino]-6-oxo-heptanoic acid tert-butyl ester To a mixture of acetyl propanol (0.39 mL, 3.8 mmol), [4-(4-fluoro-benzyloxy)-benzenesulfonylamino]-acetic acid tert-butyl ester (1.0 g, 2.53 mmol) and tetrahydrofuran (8 mL) was added triphenylphosphine (1.0 g, 3.8 mmol) and diethylazodicarboxylate (0.60 mL, 3.8 mmol). After stirring for 6 h at room temperature, the mixture was treated with additional acetyl propanol (0.15 mL), triphenyl phosphine (0.30 g) and diethylazodicarboxylate (0.20 mL). After stirring for 30 min, the mixture was concentrated in vacuo, and the residue was purified by silica gel chromatography eluting with 4:1 to 2:1 hexane-ethyl acetate, giving 0.70 g of 2-[4-(4-fluoro-benzyloxy)-benzenesulfonylamino]-oxo-heptanoic acid tert-butyl ester as a colorless solid:

1-[4-(4-Fluoro-benzyloxy)-benzenesulfonyl-3-hydroxy-3-methyl-piperidine-2-carboxylic acid tert-butyl ester To a solution of 2-[4-(4-fluoro-benzyloxy)-benzenesulfonylamino]6-oxo-heptanoic acid tert-butyl ester (0.70 g, 1.5 mmol) in 6 mL of THF was added potassium tert-butoxide (0.7 mL of a 1M solution in THF, 0.70 mmol). After stirring for 24 h at room temperature, the mixture was diluted with water, acidified with 1M HCl and extracted 3× into ethyl acetate. The combined organic layers were dried over $Na_2SO_4$, filtered and concentrated in vacuo. Filtration of the residue through a pad of silica gel eluting with 1:1 ethyl acetate-hexane afforded 1-[4-(4-fluoro-benzyloxy)-benzenesulfonyl]-3-hydroxy-3-methyl-piperidine-2-carboxylic acid tert-butyl ester as a mixture of diastereomers. Separation of the diastereomers by radial chromatography (1–4% acetone-$CH_2Cl_2$, 4 mm plate) afforded 0.12 g of each diastereomer as a colorless oil.

(+/−)(2R,3R) or (+/−)(2R,3RS)-1-[4-(4-Fluoro-benzyloxy)-benzenesulfonyl]-3-hydroxy-3-methyl-piperidine-2-carboxylic acid A solution of 1-[4-(4-fluoro-benzyloxy)-benzenesulfonyl]-3-hydroxy-3-methyl-piperidine-2-carboxylic acid tert-butyl ester in 2 mL of 1:1 trifluoroacetic acid-$CH_2Cl_2$ was stirred for 15 min–2 h at room temperature. Concentration in vacuo afforded 1-[4-(4-fluoro-benzyloxy)-benzenesulfonyl]-3-hydroxy-3-methyl-piperidine-2-carboxylic acid as a colorless syrup:

(+/−)(2R,3R) or (+/−)(2R,3S)-1-[4-(4-Fluoro-benzyloxy)-benzenesulfonyl]-3-hydroxy-3methyl-piperidine-2-carboxylic acid allyloxy-amide A solution of 11-[4-(4-fluoro-benzyloxy)-benzenesulfonyl]-3-hydroxy-3-methyl-piperidine-2-carboxylic acid (0.11 g, 0.26 mmol), HOBT (0.060 g, 0.39 mmol), O-allylhydroxylamine hydrochloride (0.057 g, 0.39 mmol), di-isopropylethylamine (0.091 mL, 0.52 mmol) and $CH_2Cl_2$ (2.7 mL) was treated with EDCI (0.075 g, 0.39 mmol). After stirring for 24 h at room temperature, the mixture was diluted with ethyl acetate, washed with 1M HCl, saturated aqueous $NaHCO_3$, dried over $Na_2SO_4$, filtered and concentrated in vacuo. Purification of the residue by radial chromatography (1:1 ethyl acetate-hexane, 2 mm plate) 1-[4-(4-fluoro-benzyloxy)-benzenesulfonyl]-3-hydroxy-3-methyl-piperidine-2-carboxylic acid allyloxy-amide (0.14 g) as a colorless syrup:

(+/−)(2R,3R) or (+/−)(2R,3S)-1-[4-(4-Fluoro-benzyloxy)-benzenesulfonyl]-3-hydroxy-3-methyl-piperidine-2-carboxylic acid hydroxyamide To a solution 1-[4-(4-fluoro-benzyloxy)-benzenesulfonyl]-3-hydroxy-3-methyl-piperidine-2-carboxylic acid allyloxy-amide (0.14 g, 0.29 mmol), triethylammonium formate (0.35 mL of a 3M solution in water, 1.0 mmol) and acetonitrile (1.5 mL) was added tetrakistriphenylphosphine palladium (0.033 g, 0.029 mmol). After stirring for 30 min at 90– 100° C., the mixture was cooled to room temperature and concentrated in vacuo and purified by silica gel chromatography eluting with 1:1 to 1:0 ethyl acetate-hexane, affording 0.030 g of 1-[4-(4-fluoro-benzyloxy)-benzenesulfonyl]-3-hydroxy-3-methyl-piperidine-2-carboxylic acid hydroxyamide as a colorless solid after trituration from $CH_2Cl_2$-hexane:

EXAMPLE 5

1-[4-(4-FLUORO-BENZYLOXY)-BENZENESULFONYL]-3-HYDROXY-3-ETHYL-PIPERIDINE-2-CARBOXYLIC ACID HYDROXYAMIDE

1-[4-(4-Fluoro-benzyloxy)-benzenesulfonyl]-3-hydroxy-3-ethyl-piperidine-2-carboxylic acid tert-butyl ester To a solution of diisopropylamine (0.35 mL, 2.5 mmol) in 10 mL of THF at −78° C. was added n-butyllithium. The mixture was warmed to room temperature and stirred for 20 min. After cooling to −78° C., a solution of 2-[4-(4-fluoro-benzyloxy)-benzenesulfonylamino]-6-oxo-octanoic acid tert-butyl ester (1.0 g, 2.1 mmol) in 2.5 mL of THF was added dropwise. The mixture was warmed to room temperature and stirred for 3 h. After acidifying with 1M HCl, the mixture was extracted 2× into ethyl acetate, and the combined organic layers were dried over $Na_2SO_4$, filtered and concentrated in vacuo. Purification of the residue by radial chromatography (1% acetone-$CH_2Cl_2$, 2 mm plate) afforded ca. 0.37 g of the (2R,3S) diastereomer and 0.09 g of the (2R,3R) diastereomer of 1-[4-(4-fluoro-benzyloxy)-benzenesulfonyl]-3-hydroxy-3-ethyl-piperidine-2-carboxylic acid tert-butyl ester as colorless syrups:

(+/−)(2R,3S) or (+/−)(2R,3R)-1-[4-(4-Fluoro-benzyloxy)-benzenesulfonyl]-3-hydroxy-3-ethyl-piperidine-2-carboxylic acid hydroxyamide Using the methods of Example 4, 1-[4-(4-fluoro-benzyloxy)-benzenesulfonyl]-3-hydroxy-3-ethyl-piperidine-2-carboxylic acid tert-butyl ester was converted to 1-[4-(4-Fluoro-benzyloxy)-benzenesulfonyl]-3-hydroxy-3-ethyl-piperidine-2-carboxylic acid hydroxyamide.

EXAMPLE 6

(2R,4R) or (2R,4S)-1-(4-ARYLOXY-BENZENESULFONYL)-4-HYDROXY-PIPERIDINE-2-CARBOXYLIC ACID HYDROXYAMIDE

4-Hydroxy-piperidine-2-carboxylic acid HCl salt 2-(1-Phenyl-ethyl)-6-oxa-2-aza-bicyclo[3.2.1]octan-7-one (prepared as described in Gillard, J. et. al., *J. Org. Chem.*,1996,61, 2226–2231) (83.5 g) is dissolved in methanol (1 L) and diluted with palladium hydroxide (20% on carbon, 10.5 g) The reaction is shaken under 50 psi hydrogen for 18 hours. The mixture is filtered through celite and the volatiles are removed under vacuum. The crude product is diluted with 6 N HCl and refluxed 18 hours. Following the removal of the solvent 4-Hydroxy-piperidine-2-carboxylic acid HCl salt was obtained as a white solid (67 g).

2-(4-Benzyloxy-benzenesulfonyl)-6-oxa-2-aza-bicyclo[3.2.1]octan-7-one

To 4-Hydroxy-piperidine-2-carboxylic acid HCl salt (11.52 g) is added triethylamine (35.5 mL) and DMF (100 mL). The mixture is cooled to 0° C. and the sulfonyl chloride (35.9 g) is added in five portions. The reaction is stirred for 4 hours at 0° C. and then is diluted with water and ethyl acetate. The aqueous layer is washed with ethyl acetate and the combined organic layers are dried with magnesium sulfate and concentrated. The resulting solid is purified by silica gel chromatography to give 2-(4-Benzyloxy-benzenesulfonyl)-6-oxa-2-aza-bicyclo[3.2.1]octan-7-one (14.8 g).

2-(4-Hydroxy-benzenesulfonyl)-6-oxa-2-aza-bicyclo [3.2.1]octan-7-one

Benzyloxy-benzenesulfonyl)-6-oxa-2-aza-bicyclo[3.2.1] octan-7-one is dissolved in methanol (50 mL) and is treated with 5% Pd/C (0.730 g) and is subjected to a hydrogen atmosphere (50 psi) with shaking for 1 hour. The reaction is diluted with 1:1 ethyl acetate:benzene an is filtered through celite. The solvent is removed under reduced pressure and the residue is purified by silica gel chromatography to give 2-(4-Hydroxy-benzenesulfonyl)-6-oxa-2-aza-bicyclo[3.2.1] octan-7-one (3.25 g).

1-(4-Aryloxy-benzenesulfonyl)-6-oxa-2-aza-bicyclo [3.2.1]octan-7-one

Method A: General Method for the formation of 1-(4-Aryloxy-benzenesulfonyl)-6-oxa-2-aza-bicyclo [3.2.1]octan-7-ones To a dimethylformamide (0.6 mL) solution of 2-(4-Hydroxy-benzenesulfonyl)-6-oxa-2-aza-bicyclo[3.2.1] octan-7-one (101.1 mg) and cesium carbonate (331.3 mg) is added the aryl halide (2.5 equiv). The reaction is heated to 50° C. with shaking for 12–24 hours. The sample is cooled, diluted with water and ethyl acetate, and extracted two times with ethyl acetate. The organic layers are combined, dried over sodium sulfate and concentrated. The product is precipitated from diethyl ether to give the Aryloxy-benzenesulfonyl)-6-oxa-2-aza-bicyclo[3.2.1]octan-7-one.

1-(4-Aryloxy-benzenesulfonyl)-4-hydroxy-piperidine-2-carboxylic acid hydroxyamide General Method for the formation of 1-(4-Aryloxy-benzenesulfonyl)-4-hydroxy-piperidine-2-carboxylic acid hydroxyamides The Aryloxy-benzenesulfonyl)-6-oxa-2-aza-bicyclo [3.2.1]octan-7-one is diluted with hydroxyl amine in methanol (prepared via the addition of sodium metal to a solution of hydroxyl amine hydrochloride in methanol). The sample is heated to 60° C. for 1 hour then is cooled, and extracted from 1 N HCl into ethyl acetate and washed with saturated sodium bicarbonate. The organic layer is dried over sodium sulfate and concentrated. The product 1-(4-Aryloxy-benzenesulfonyl)-4-hydroxy-piperidine-2-carboxylic acid hydroxyamide is obtained after silica gel chromatography.

EXAMPLE 7

(2R,4R) or (2R,4S)-1-(4-ARYLOXY-BENZENESULFONYL)-4-HYDROXY-PIPERIDINE-2-CARBOXYLIC ACID HYDROXYAMIDES 1-(4-Aryloxy-benzenesulfonyl)-4-hydroxy-piperidine-2-carboxylic acid allyloxy-amides)

Method D: General Method for the Preparation of 1-(4-Aryloxy-benzenesulfonyl)-4-hydroxy-piperidine-2-carboxylic acid allyloxy-amides Allyl hydroxyl amine (8.2 mmol) is dissolved in benzene (5 mL) and cooled to 0° C. Trimethyl aluminum (8.2 mmol) is added dropwise. The reaction is stirred at 23° C. for 0.75 hours and the Aryloxy-benzenesulfonyl)-6-oxa-2-aza-bicyclo[3.2.1]octan-7-one (4.1 mmol) in benzene (5 mL) is added quickly. The mixture is heated to reflux for 20 minutes, cooled to 23° C. and diluted with ethyl acetate. 1N HCl is added and the aqueous layer is washed with ethyl acetate. The organic layers are combined, dried over sodium sulfate and concentrated to give the 1-(4-Aryloxy-benzenesulfonyl)-4-hydroxy-piperidine-2-carboxylic acid allyloxy-amide.

1-(4-Aryloxy-benzenesulfonyl)-4-oxo-piperidine-2-carboxylic acid allyloxy-amide.

General Method for the Preparation of 1-(4-Aryloxy-benzenesulfonyl)-4-oxo-piperidine-2-carboxylic acid allyloxy-amides The 1-(4-Aryloxy-benzenesulfonyl)-4-hydroxy-piperidine-2-carboxylic acid allyloxy-amide (4.08 mmol), pyridinium chlorochromate (8.12 mmol) and dichloromethane (30 mL) are stirred at 23° C. for 18 hours. The reaction is diluted with ethyl acetate and filtered through silica gel. The solvent is removed under reduced pressure and the residue is purified by silica gel chromatography to give the 1-(4-Aryloxy-benzenesulfonyl)-4-oxo-piperidine-2-carboxylic acid allyloxy-amide.

1-(4-Aryloxy-benzenesulfonyl)-4-hydroxy-piperidine-2-carboxylic acid allyloxy-amides General Method for the Preparation of 1-(4-Aryloxy-benzenesulfonyl)-4-hydroxy-piperidine-2-carboxylic acid allyloxy-amides The 1-(4-Aryloxy-benzenesulfonyl)-4-oxo-piperidine-2-carboxylic acid allyloxy-amide (1.15 mmol) is cooled to 0° C. in tetrahydrofuran (10 mL). Lithium borohydride (1.8 mmol) is added at 0° C. and the reaction is stirred at 0° C. for 15 min. The reaction is diluted with ethyl acetate and water. The aqueous layer is washed with ethyl acetate, the organic layers are combined, dried over sodium sulfate and concentrated to give a mixture of alcohols which are diluted with benzene and treated with catalytic p-toluene sulfonic acid. The mixture is heated to 85° C. for 2 hours, allowed to cool to 23° C. and diluted with ethyl acetate and saturated sodium bicarbonate. The aqueous layer is washed with ethyl acetate, dried over sodium sulfate and concentrated. Chromatography on silica gel gave the 1-(4-Aryloxy-benzenesulfonyl)-4-hydroxy-piperidine-2-carboxylic acid allyloxy-amide.

1-(4-Aryloxy-benzenesulfonyl)-4-hydroxy-piperidine-2-carboxylic acid hydroxyamides General Method for the Preparation of 1-(4-Aryloxy-benzenesulfonyl)-4-hydroxy-piperidine-2-carboxylic acid hydroxyamides The 1-(4-Aryloxy-benzenesulfonyl)-4-hydroxy-piperidine-2-carboxylic acid allyloxy-amide (1.1 mmol) is diluted with acetonitrile and palladium tetrakistriphenylphosphine (0.11 mmol) and triethylammonium formate (excess) is added. The mixture is heated for 1 hour to 80° C. then is cooled to 23° C., diluted with ethyl acetate and 1 N HCl. The organic layer is dried over sodium sulfate and concentrated. ° C. hromatography on silica gel gave the 1-(4-Aryloxy-benzenesulfonyl)-4-hydroxy-piperidine-2-carboxylic acid hydroxyamide.

EXAMPLE 8

(2R,4R) or (2R,4S)-1-(4-ARYLOXY-BENZENESULFONYL)-4-HYDROXY-4-(ALKYL OR ARYL)-PIPERIDINE-2-CARBOXYLIC ACID HYDROXYAMIDE 1-(4-Aryloxy-benzenesulfonyl)-4-hydroxy-4-(alkyl or aryl)-piperidine-2-carboxylic acid allyloxy-amides Method E: General Method for the preparation of 1-(4-Aryloxy-benzenesulfonyl)-4-hydroxy-4-(alkyl or aryl)-piperidine-2-carboxylic acid allyloxy-amides The 1-(4-Aryloxy-benzenesulfonyl)-4-oxo-piperidine-2-carboxylic acid allyloxy-amide (1.16 mmol) is diluted with tetrahydrofuran (10 mL) and cooled to 0° C. The appropriate Grignard reagent is added (2.5 eq) and the reaction is allowed to warm to room temperature. The mixture is diluted with ethyl acetate and 1 N HCl, washed with ethyl acetate and the organic layers are combined, dried over sodium sulfate and concentrated. The diastereomers are separated via silica gel chromatography to give the 1-(4-Aryloxy-benzenesulfonyl)-4-hydroxy-4-(alkyl or aryl)-piperidine-2-carboxylic acid allyloxy-amide which is converted to the hydroxamic acid using the same procedures that were used in method D.

1-(4-Aryloxy-benzenesulfonyl)-4-hydroxy-4-(alkyl or aryl)-piperidine-2-carboxylic acid hydroxyamide Using similar procedures to those described in Example 8, 1-(4-Aryloxy-benzenesulfonyl)-4-hydroxy-4-(alkyl or aryl)-piperidine-2-carboxylic acid allyloxy-amide was converted to 1-(4-Aryloxy-benzenesulfonyl)-4-hydroxy-4-(alkyl or aryl)-piperidine-2-carboxylic acid hydroxyamide.

TABLE 1

The compounds of Table 1 were prepared according to the methods of Example 6, substituting the appropriate benzyl halide.

| Example | STRUCTURE | Method | Yield, III | MS data |
|---|---|---|---|---|
| 9 | 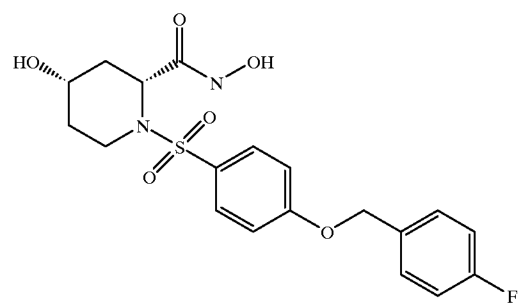 | B | | |
| 10 | 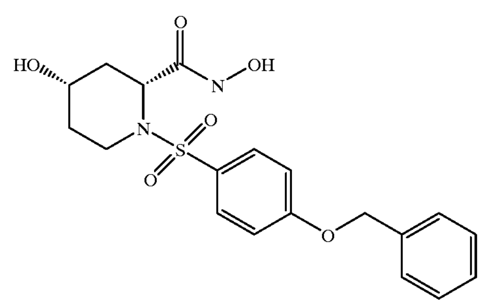 | B | | |
| 11 | 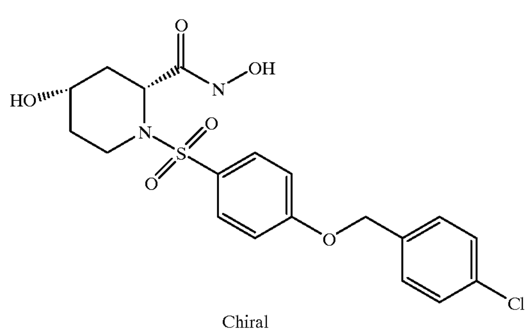 | A | 88% | 439.1 |

TABLE 1-continued
The compounds of Table 1 were prepared according to the methods of Example 6, substituting the appropriate benzyl halide.
| Example | STRUCTURE | Method | Yield, III | MS data |
|---|---|---|---|---|
| 12 | 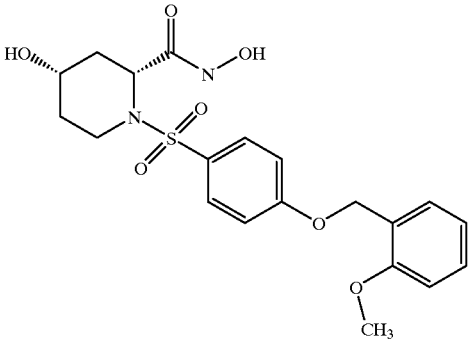 Chiral | A | 61% | 435.1 |
| 13 | 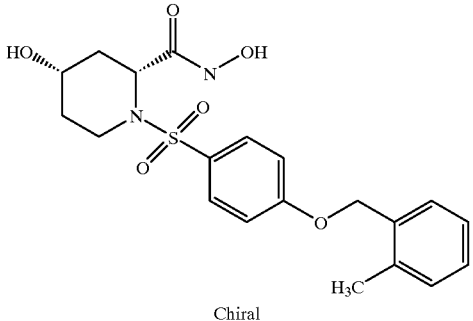 Chiral | A | 54% | 419.2 |
| 14 | 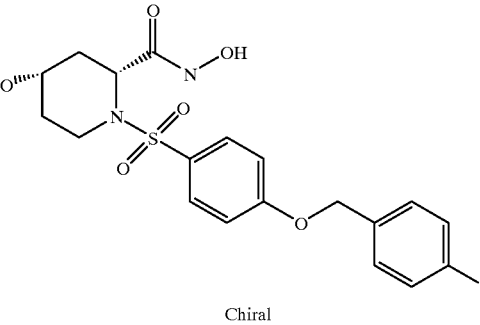 Chiral | A | 70% | 419.2 |
| 15 | 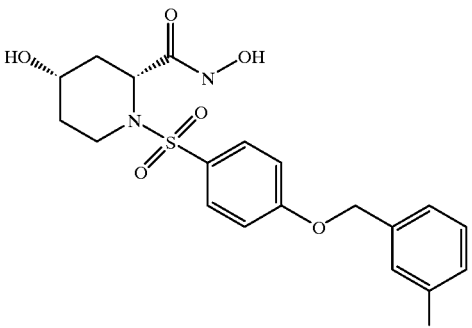 Chiral | A | 94% | 419.1 |

TABLE 1-continued

The compounds of Table 1 were prepared according to the methods of Example 6, substituting the appropriate benzyl halide.

| Example | STRUCTURE | Method | Yield, III | MS data |
|---|---|---|---|---|
| 16 | 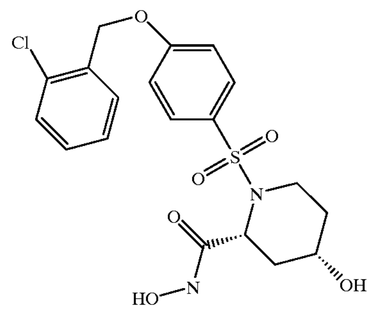 | A | 42% | 440.1 |
| 17 | 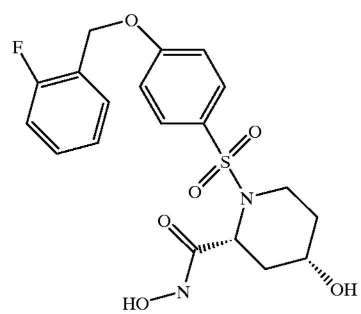 | A | 48% | 423 |
| 18 | 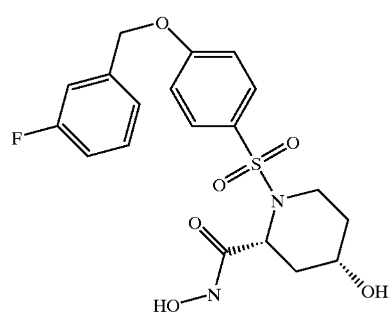 | A | 46% | 423 |
| 19 | (Chiral) | A | 88% | 435 |

TABLE 1-continued
The compounds of Table 1 were prepared according to the methods of Example 6, substituting the appropriate benzyl halide.
| Example | STRUCTURE | Method | Yield, III | MS data |
|---|---|---|---|---|
| 20 | 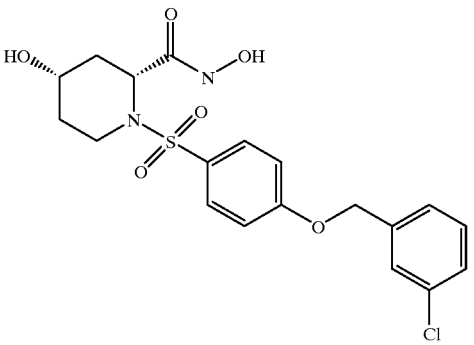 Chiral | A | 89% | 439 |
| 21 | 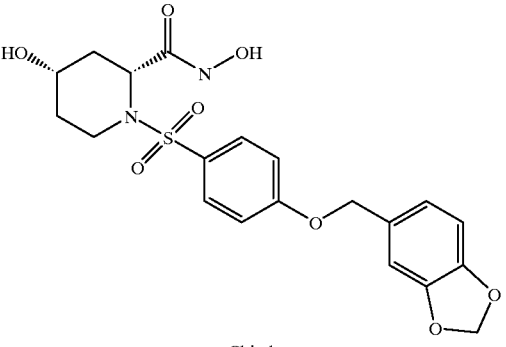 Chiral | | 40% | 449 |
| 22 | 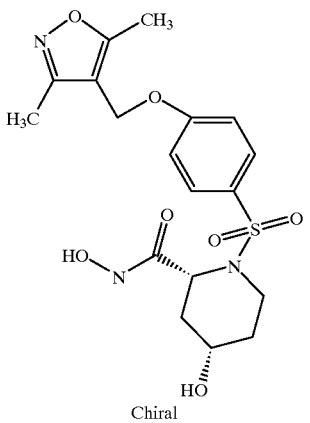 Chiral | A | 29% | 424 |

TABLE 2
The compounds of Table 2 were prepared according to the methods of Example 8, substituting the appropriate Grignard reagent and benzyl halide.
| Example | STRUCTURE | Method | Yield, XI | MS data, XI |
|---|---|---|---|---|
| 23 | 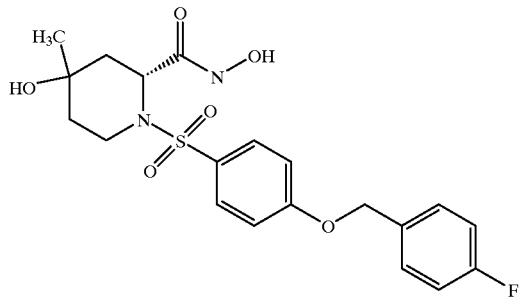 Chiral | D | | |
| 24 | 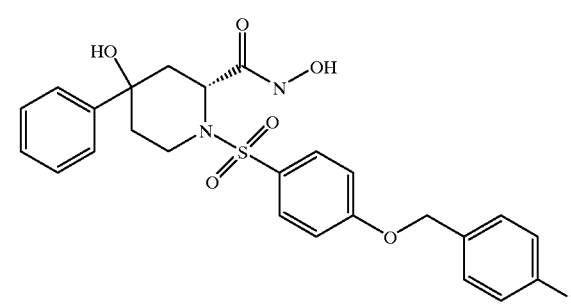 Chiral | D | | |
| 25 | 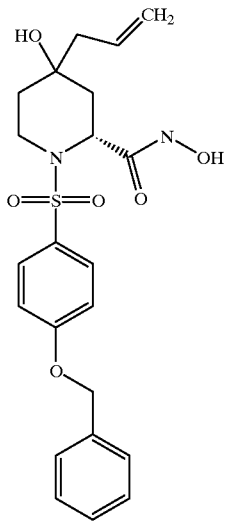 | E | 68% | 445.1 |

TABLE 2-continued

The compounds of Table 2 were prepared according to the methods of Example 8, substituting the appropriate Grignard reagent and benzyl halide.

| Example | STRUCTURE | Method | Yield, XI | MS data, XI |
|---------|-----------|--------|-----------|-------------|
| 26 | (structure; Chiral) | E | 15% | 419.2 |
| 27 | (structure; Chiral) | E | 47% | 489.1 |
| 28 | (structure; Chiral) | E | 64% | 495 |
| 29 | (structure; Chiral) | E | 46% | 433 |

TABLE 2-continued
The compounds of Table 2 were prepared according to the methods of Example 8, substituting the appropriate Grignard reagent and benzyl halide.
| Example | STRUCTURE | Method | Yield, XI | MS data, XI |
|---|---|---|---|---|
| 30 | 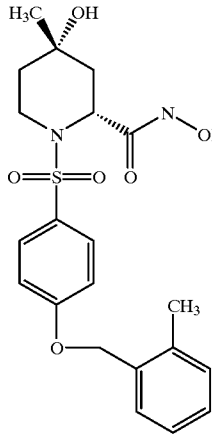 | E | 37% | 433.1 |
| 31 | 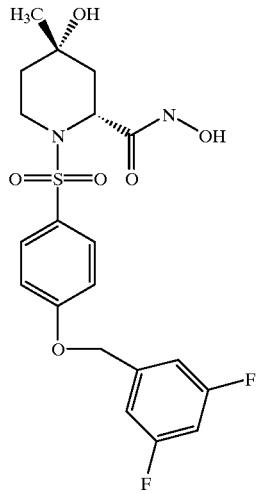 | E | 40% | 454.9 |
| 32 | 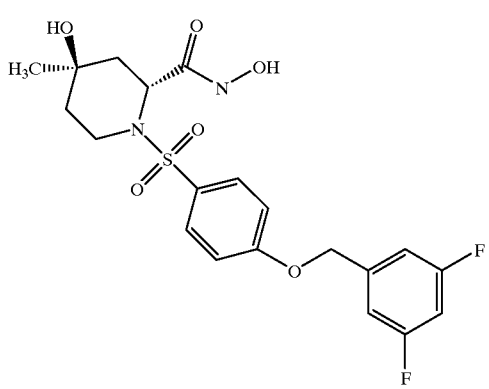<br>Chiral | E | 82% | 455.1 |

TABLE 3
The compounds of Table 3 were prepared according to the methods of Example 4, substituting the appropriate gamma hydroxy ketone.
| Example | Structure | MW | APCI[M − H]− | Yield | HPLC Ret Time | 1H NHR (alpha to hydroxamic acid) |
|---|---|---|---|---|---|---|
| 33 | 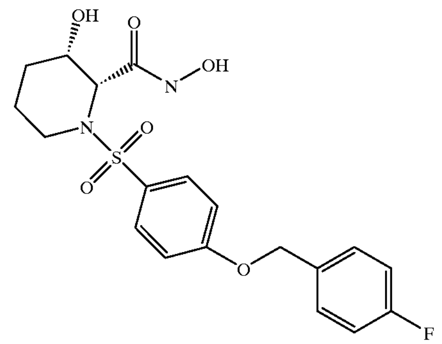 | 424.5 | 423.3 | 25% | 3.234 min | 4.37 (d, 1H, J=6.0 Hz) |
| 34 | 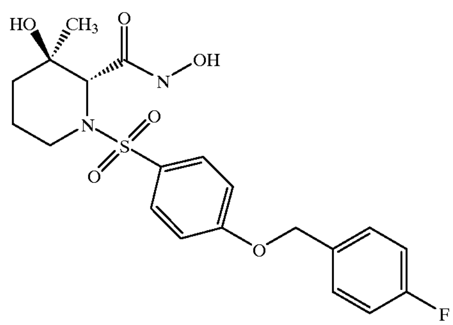 | 438.5 | 437 | 26% | 3.304 min | 4.025 (s, 1H) |
| 35 | 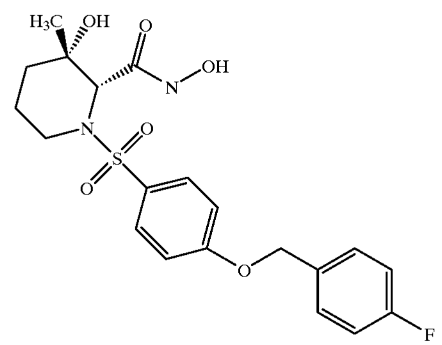 | 438.5 | 437 | 11% | 3.442 min | 3.975 (s, 1H) |
| 36 | 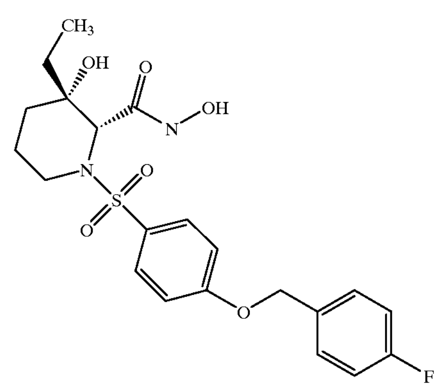 | 452.5 | 451.3 | 20% | 3.567 min | 4.010 (s, 1H) |
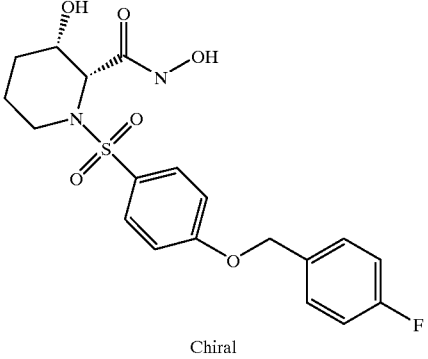

TABLE 3-continued

The compounds of Table 3 were prepared according to the methods of Example 4, substituting the appropriate gamma hydroxy ketone.

| Example | Structure | MW | APCI[M − H]− | Yield | HPLC Ret Time | 1H NHR (alpha to hydroxamic acid) |
|---|---|---|---|---|---|---|
| 37 | 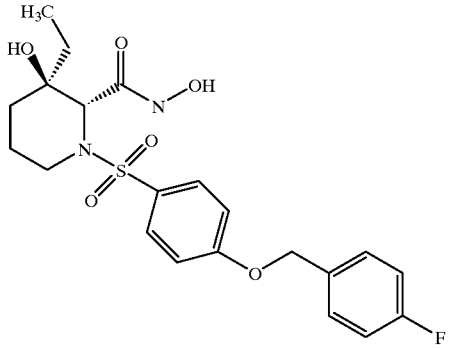 | 452.5 | 451.3 | 47% | 3.453 min | 4.016 (s, 1H) |
| 38 | 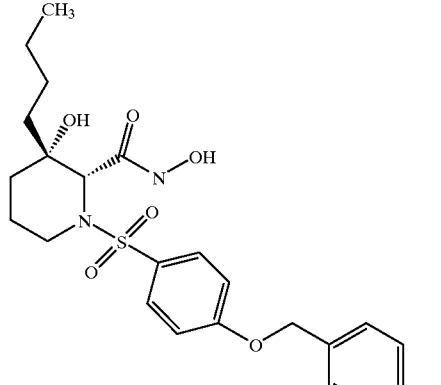 | 480.6 | 479 | 5% | 3.887 min | 3.985 (s, 1H) |

TABLE 4

The compounds of Table 4 were prepared according to the methods of Example 1 and 2, substituting the appropriate benzyl halide.

| Ex. | Structure | MW | APCI[M − H]− | Yield | HPLC Ret Time (min) |
|---|---|---|---|---|---|
| 39 | 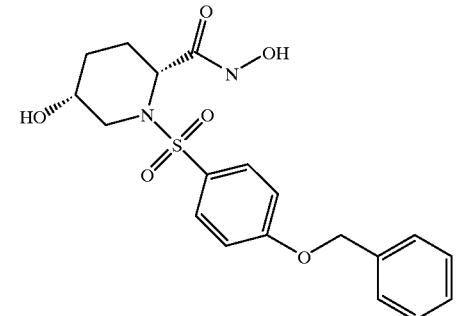 Chiral | 406.46 | 405.1 | 14% | 3.151 |

TABLE 4-continued
The compounds of Table 4 were prepared according to the methods of Example 1 and 2, substituting the appropriate benzyl halide.
| Ex. | Structure | MW | APCI[M − H]⁻ | Yield | HPLC Ret Time (min) |
|---|---|---|---|---|---|
| 40 | 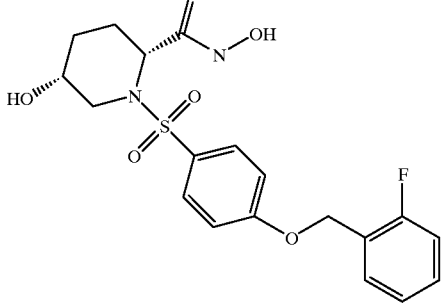 Chiral | 424.45 | 423.1 | 47% | 3.179 |
| 41 | 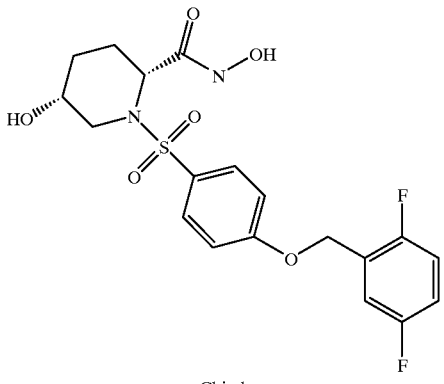 Chiral | 442.44 | 441.1 | 35% | 3.234 |
| 42 | 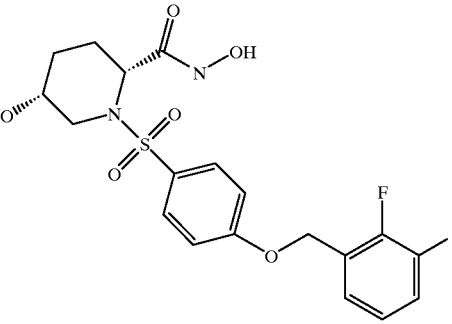 Chiral | 442.45 | 441.1 | 45% | 3.269 |
| 43 | 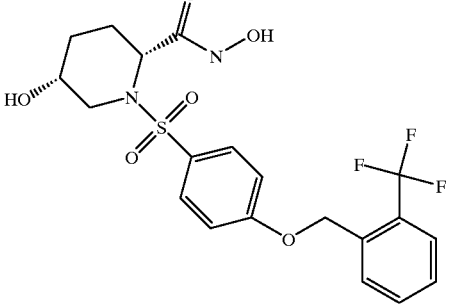 Chiral | 474.46 | 473.0 | 35% | 3.426 |

TABLE 4-continued
The compounds of Table 4 were prepared according to the methods of Example 1 and 2, substituting the appropriate benzyl halide.
| Ex. | Structure | MW | APCI[M − H]⁻ | Yield | HPLC Ret Time (min) |
|---|---|---|---|---|---|
| 44 | 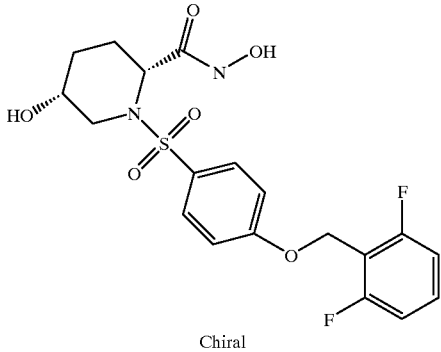 Chiral | 442.44 | 441.0 | 38% | 3.136 |
| 45 | 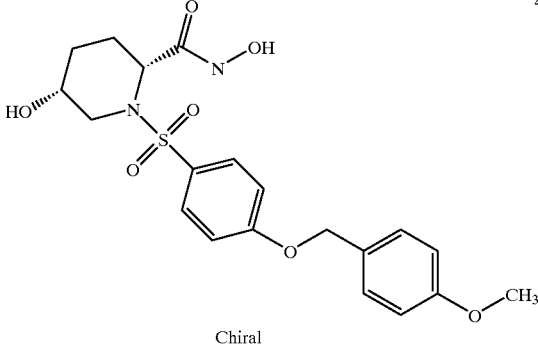 Chiral | 436.49 | 435.0 | 32% | 3.139 |
| 46 | 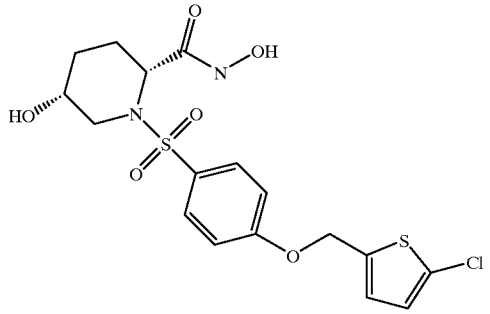 Chiral | 446.93 | 445.1 | 44% | 3.383 |

TABLE 4-continued
The compounds of Table 4 were prepared according to the methods of Example 1 and 2, substituting the appropriate benzyl halide.
| Ex. | Structure | MW | APCI[M − H]⁻ | Yield | HPLC Ret Time (min) |
|---|---|---|---|---|---|
| 47 | 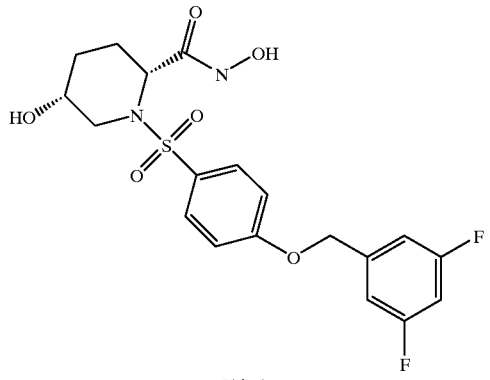 Chiral | 442.44 | 441.1 | 50% | 3.294 |
| 48 | 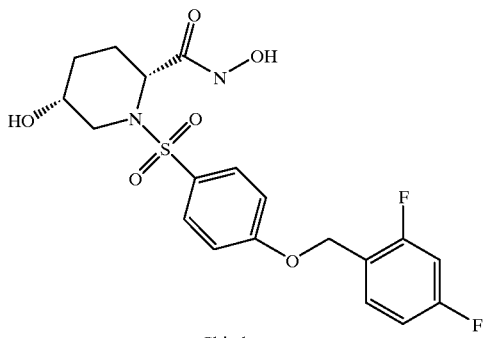 Chiral | 442.44 | 441.1 | 57% | 3.237 |
| 49 | 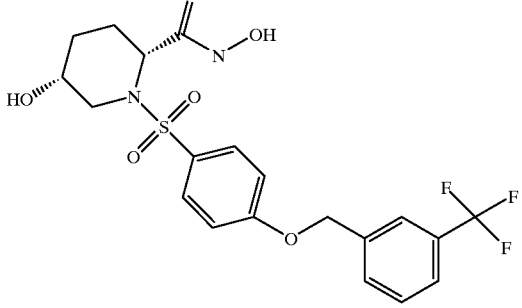 Chiral | 474.46 | 473.1 | 32% | 3.484 |

TABLE 4-continued
The compounds of Table 4 were prepared according to the methods of Example 1 and 2, substituting the appropriate benzyl halide.
| Ex. | Structure | MW | APCI[M − H]⁻ | Yield | HPLC Ret Time (min) |
|---|---|---|---|---|---|
| 50 | 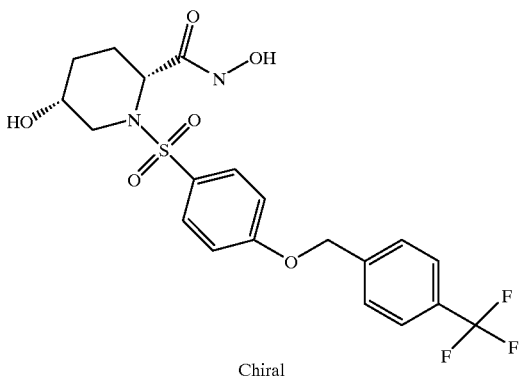 Chiral | 474.46 | 473.1 | 32% | 3.525 |
| 51 | 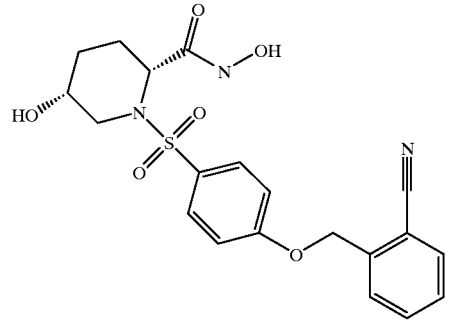 Chiral | 431.47 | 430.0 | 36% | 2.952 |
| 52 | 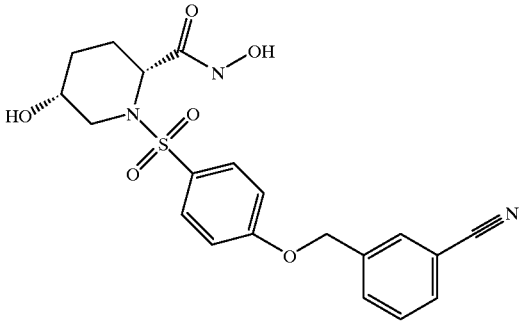 Chiral | 431.47 | 430.0 | 3% | 2.985 |
| 53 | 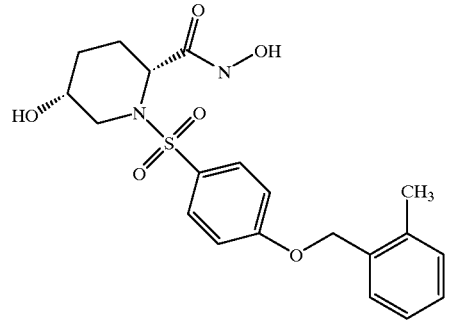 Chiral | 420.49 | 419.3 | 50% | 3.309 |

TABLE 4-continued

The compounds of Table 4 were prepared according to the methods of Example 1 and 2, substituting the appropriate benzyl halide.

| Ex. | Structure | MW | APCI[M − H]− | Yield | HPLC Ret Time (min) |
|---|---|---|---|---|---|
| 54 | (Chiral structure) | 434.52 | 433.2 | 42% | 3.506 |
| 55 | (Chiral structure) | 438.48 | 439.0 [M + H]+ | 10 | 3.444 |
| 56 | (Chiral structure) | 438.48 | 439.0 [M + H]+ | 6 | 3.341 |

TABLE 4-continued
*The compounds of Table 4 were prepared according to the methods of Example 1 and 2, substituting the appropriate benzyl halide.*
| Ex. | Structure | MW | APCI[M − H]⁻ | Yield | HPLC Ret Time (min) |
|---|---|---|---|---|---|
| 57 | 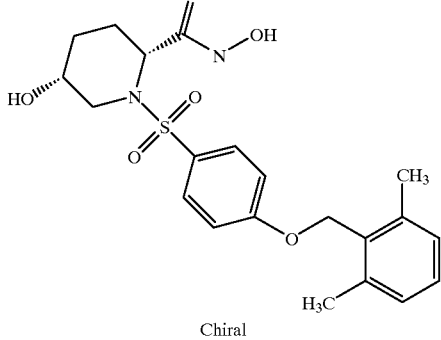 Chiral | 434.52 | 435.0 [M + H]⁺ | 22 | 3.438 |
| 58 | 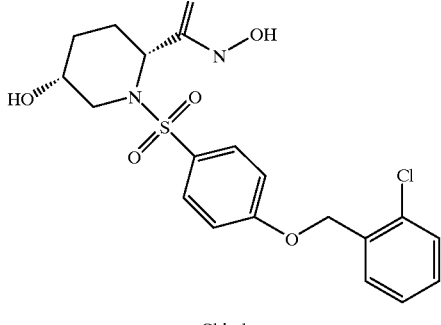 Chiral | 440.91 | | 38 | 3.339 |
| 59 | 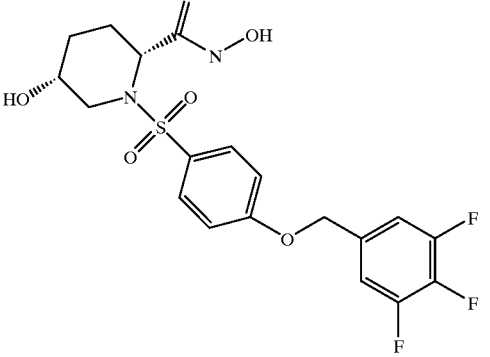 Chiral | 460.43 | | 43 | 3.426 |

TABLE 4-continued
The compounds of Table 4 were prepared according to the methods of Example 1 and 2, substituting the appropriate benzyl halide.
| Ex. | Structure | MW | APCI[M − H]⁻ | Yield | HPLC Ret Time (min) |
|---|---|---|---|---|---|
| 60 | 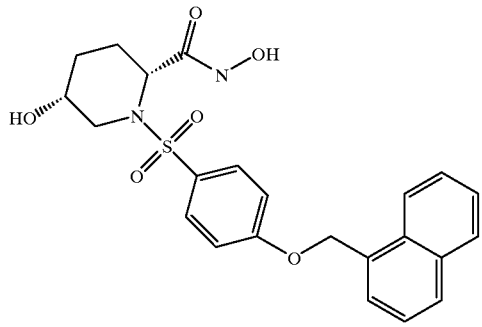 Chiral | 456.56 | 454.9 | 47 | 3.535 |
| 61 | 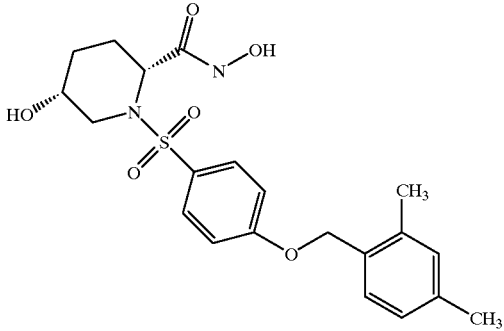 Chiral | 434.52 | 433.1 | 43 | NA |
| 62 | 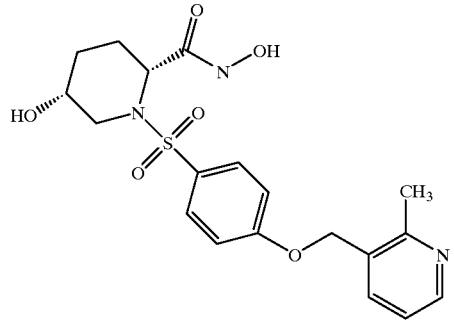 Chiral | 421.48 | 420.1 | 23 | 1.955 |

TABLE 4-continued
The compounds of Table 4 were prepared according to the methods of Example 1 and 2, substituting the appropriate benzyl halide.
| Ex. | Structure | MW | APCI[M − H]⁻ | Yield | HPLC Ret Time (min) |
|---|---|---|---|---|---|
| 63 | 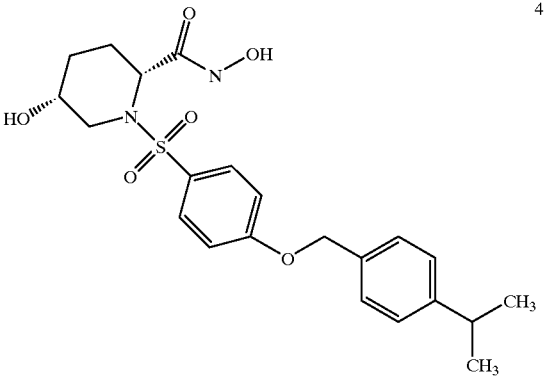 Chiral | 448.54 | 447.1 | 30 | NA |
| 64 | 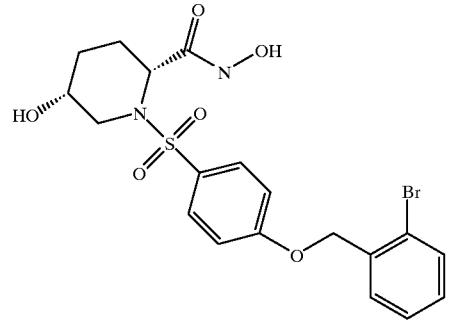 Chiral | 485.36 | 484.9 | 8 | 3.405 |
| 65 | 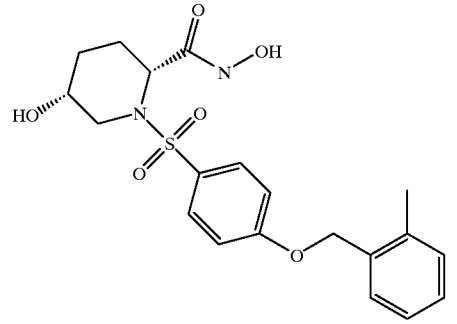 Chiral | 532.37 | 530.9 | 46 | 3.43 |
| 66 | 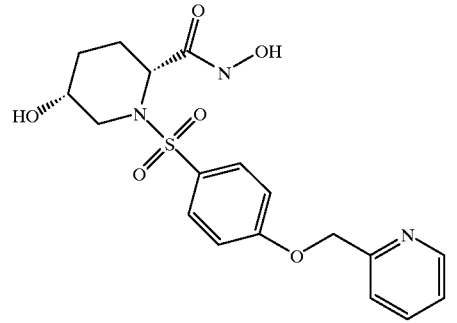 Chiral | 407.45 | 406.1 | 14 | 1.958 |

TABLE 4-continued
The compounds of Table 4 were prepared according to the methods of Example 1 and 2, substituting the appropriate benzyl halide.
| Ex. | Structure | MW | APCI[M − H]⁻ | Yield | HPLC Ret Time (min) |
|---|---|---|---|---|---|
| 67 | 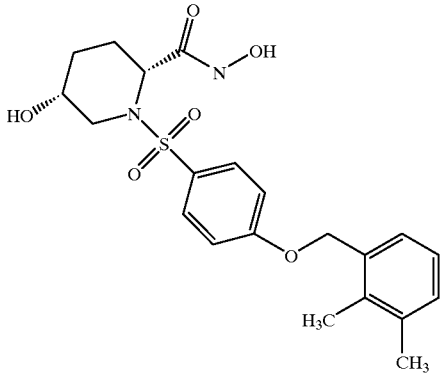 Chiral | 434.52 | 435.2 [M + H]⁺ | 40 | 3.45 |
| 68 | 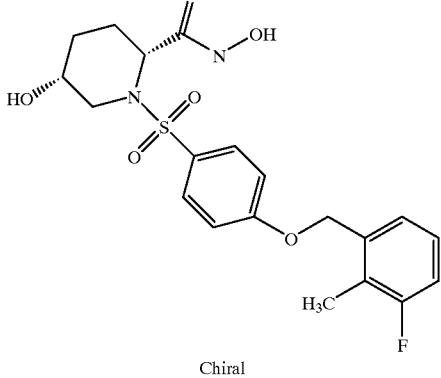 Chiral | 438.48 | 439.20 [M + H]⁺ | 18 | 3.419 |
| 69 | 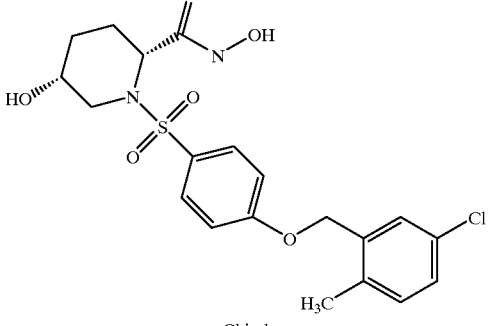 Chiral | 454.93 | 455.1 [M + H]⁺ | 30 | 3.591 |

TABLE 4-continued
The compounds of Table 4 were prepared according to the methods of Example 1 and 2, substituting the appropriate benzyl halide.
| Ex. | Structure | MW | APCI[M − H]⁻ | Yield | HPLC Ret Time (min) |
|---|---|---|---|---|---|
| 70 | 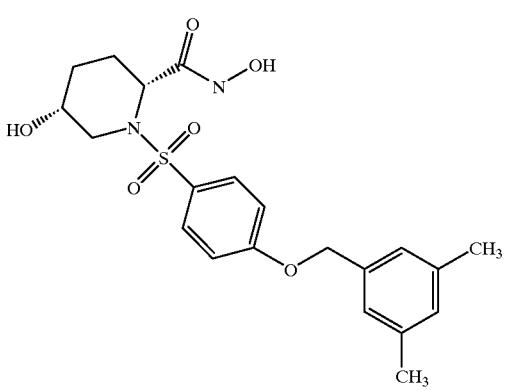 Chiral | 434.52 | | 35 | NA |
| 71 | 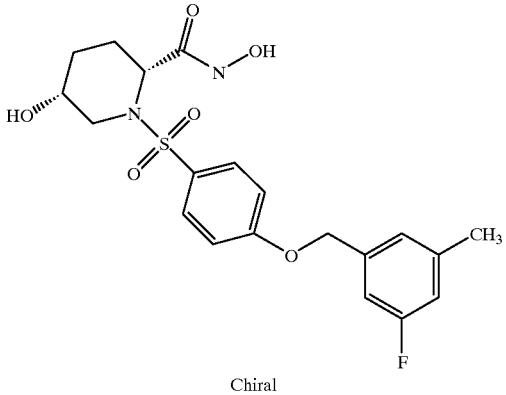 Chiral | 438.48 | | 10 | 3.292 |
| 72 | 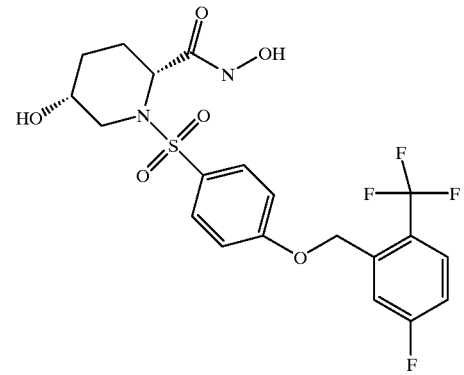 Chiral | 492.45 | 493.1 [M + H]⁺ | 20 | 3.461 |

TABLE 4-continued
The compounds of Table 4 were prepared according to the methods of Example 1 and 2, substituting the appropriate benzyl halide.
| Ex. | Structure | MW | APCI[M − H]⁻ | Yield | HPLC Ret Time (min) |
|---|---|---|---|---|---|
| 73 | 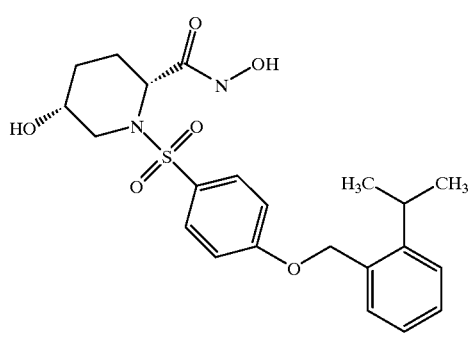 Chiral | 448.54 | 449.2 [M + H]⁺ | 44 | 3.585 |
| 74 | 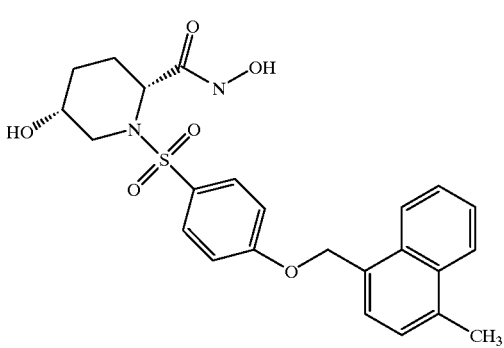 Chiral | 470.55 | 471.2 [M + H]⁺ | 12 | 3.661 |
| 75 | 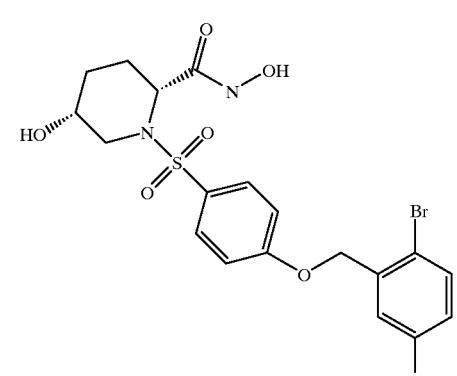 Chiral | 503.35 | 503.0 [M + H]⁺ | 62 | 3.448 |

TABLE 4-continued
The compounds of Table 4 were prepared according to the methods of Example 1 and 2, substituting the appropriate benzyl halide.
| Ex. | Structure | MW | APCI[M − H]⁻ | Yield | HPLC Ret Time (min) |
|---|---|---|---|---|---|
| 76 | 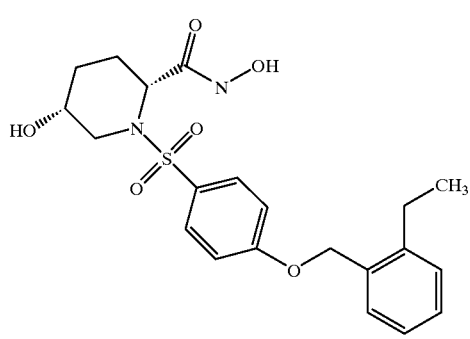 Chiral | 434.52 | 435.3 [M + H]⁺ | 27 | 3.328 |
| 77 | 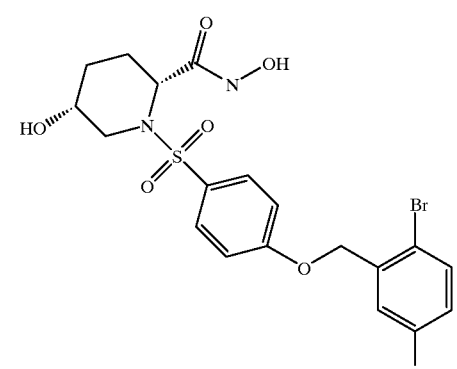 Chiral | 564.25 | 565.0 [M + H]⁺ | 38 | 3.665 |
| 78 | 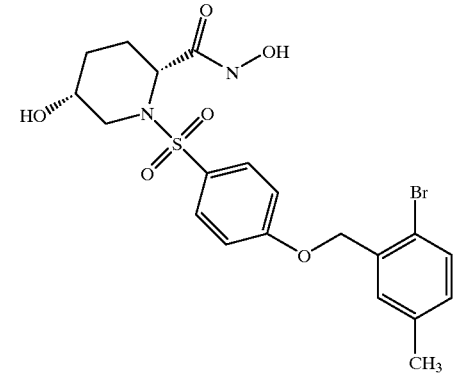 Chiral | 499.38 | 501.1 [M + H]⁺ | 50 | 3.512 |

TABLE 4-continued

The compounds of Table 4 were prepared according to the methods of Example 1 and 2, substituting the appropriate benzyl halide.

| Ex. | Structure | MW | APCI[M − H]⁻ | Yield | HPLC Ret Time (min) |
|---|---|---|---|---|---|
| 79 | 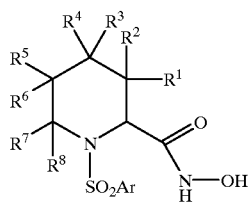<br>Chiral | 420.49 | 421.1 [M + H]⁺ | 36 | 3.156 |

PREPARATION 1

4-Benzyloxy-benzenesulfonate, sodium salt (Method F)

4-Hydroxybenenesulfonate, sodium salt (100.69 g) is diluted with water (225 mL) and heated to 50° C. Solid NaOH (17.74 g) is added and when it has completely dissolved benzyl bromide (51.1 mL in 180 mL ethanol) is added over 20 minutes. The reaction is heated to reflux for 18 hours and then is cooled to 0° C. and filtered. The resulting precipitate is washed with cold water, then diethyl ether and dried under vacuum to give 4-Benzyloxy-benzenesulfonate, sodium salt (107.39 g).

4-Benzyloxy-benzenesulfonyl chloride

To a flask containing 4-Benzyloxy-benzenesulfonate, sodium salt (42.07 g) is added thionyl chloride (170 mL). This solution is treated with dimethyl formamide (0.5 mL) and is heated to 70° C. for 4 hours. The reaction is allowed to cool and is concentrated under reduced pressure then is diluted with ethyl acetate and washed with water (3 times) followed by three washes with saturated sodium bicarbonate and brine. The organic layer is dried over sodium sulfate and concentrated to give 4-Benzyloxy-benzenesulfonyl chloride as white solid (39.18 g).

What is claimed is:

1. A compound of the formula

I

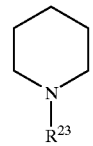

wherein $R^1$–$R^8$ are selected from the group consisting of hydroxy, hydrogen, $NH_2$, halogen, —CN, $(C_1$–$C_6)$ alkyl, $(C_2$–$C_6)$alkenyl, $(C_6$–$C_{10})$aryl$(C_2$–$C_6)$alkenyl, $(C_2$–$C_9)$heteroaryl$(C_2$–$C_6)$alkenyl, $(C_2$–$C_6)$alkynyl, $(C_6$–$C_{10})$aryl$(C_2$–$C_6)$alkynyl, $(C_2$–$C_9)$heteroaryl $(C_2$–$C_6)$alkynyl, $(C_1$–$C_6)$alkylamino, $[(C_1$–$C_6)$alkyl$]_2$ amino, $(C_1$–$C_6)$alkylthio, $(C_1C_6)$alkoxy, perfluoro $(C_1$–$C_6)$alkyl, perfluoro$(C_1$–$C_6)$alkoxy, $(C_6$–$C_{10})$aryl, $(C_2$–$C_9)$heteroaryl, $(C_6C_{10})$arylamino, $(C_6$–$C_{10})$ arylthio, $(C_6$–$C_{10})$aryloxy, $(C_2$–$C_9)$heteroarylamino, $(C_2$–$C_9)$heteroarylthio, $(C_2$–$C_9)$heteroaryloxy, $(C_3$–$C_6)$ cycloalkyl, $(C_1$–$C_6)$alkyl(hydroxymethylene), piperidyl, $(C_1$–$C_6)$alkylpiperidyl, $(C_1$–$C_6)$acyl, $(C_1$–$C_6)$acylamino, $(C_1$–$C_6)$acylthio, $(C_1$–$C_6)$acyloxy, $(C_1$–$C_6)$alkoxy-(C═O)—, —$CO_2H$, $(C_1$–$C_6)$alkyl-NH—(C═O)—, and $[(C_1$–$C_6)$alky$]_2$-N—(C═O)—;

wherein said $(C_1$–$C_6)$alkyl is optionally substituted by one or two groups selected from $(C_1$–$C_6)$alkylthio, $(C_1$–$C_6)$alkoxy, trifluoromethyl, halo, —CN, $(C_6$–$C_{10})$ aryl, $(C_2$–$C_9)$heteroaryl, $(C_6$–$C_{10})$arylamino, $(C_6$–$C_{10})$ arylthio, $(C_6$–$C_{10})$aryloxy, $(C_2$–$C_9)$heteroarylamino, $(C_2$–$C_9)$heteroarylthio, $(C_2$–$C_9)$heteroaryloxy, $(C_6$–$C_{10})$aryl$(C_6$–$C_{10})$aryl, $(C_3$–$C_6)$cycloalkyl, hydroxy, piperazinyl, $(C_6$–$C_{10})$aryl$(C_1$–$C_6)$alkoxy, $(C_2$–$C_9)$heteroaryl$(C_1$–$C_6)$alkoxy, $(C_1$–$C_6)$acylamino, $(C_1$–$C_6)$acylthio, $(C_1$–$C_6)$acyloxy, $(C_1$–$C_6)$ alkylsulfinyl, $(C_6$–$C_{10})$arylsulfinyl, $(C_1$–$C_6)$ alkylsulfonyl, $(C_6$–$C_{10})$arylsulfonyl, amino, $(C_1$–$C_6)$ alkylamino or $((C_1$–$C_6)$alkyl$)_2$amino;

or $R^1$ and $R^2$, or $R^3$ and $R^4$, or $R^5$ and $R^6$ may be taken together to form a carbonyl;

or $R^1$ and $R^2$, or $R^3$ and $R^4$, or $R^5$ and $R^6$, or $R^7$ and $R^8$ may be taken together to form a $(C_3$–$C_6)$cycloalkyl, oxacyclohexyl, thiocyclohexyl, indanyl or tetralinyl ring or a group of the formula Ar is $(C_6$–$C_{10})$aryl$(C_1$–$C_6)$alkoxy$(C_6$–$C_{C10})$aryl, $(C_6$–$C_{10})$aryl$(C_1$–$C_6)$alkoxy$(C_2$–$C_9)$heteroaryl, $(C_2$–$C_9)$heteroaryl$(C_1$–$C_6)$alkoxy$(C_6$–$C_{10})$aryl, $(C_2$–$C_9)$heteroaryl$(C_1$–$C_6)$alkoxy$C_2$–$C_9)$heteroaryl optionally substituted by one or more substituents, independently selected from halo, —CN, $(C_1-C_6)$alkyl optionally substituted with one or more fluorine atoms, hydroxy, hydroxy-$(C_1-C_6)$alkyl, $(C_1-C_6)$alkoxy optionally substituted with one or more fluorine atoms, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, [$(C_1-C_6)$alkyl]$_2$amino, amino$(C_1-C_6)$alkyl, $(C_1-C_6)$alkylamino$(C_1-C_6)$alkyl, [$(C_1-C_6)$alkyl]$_2$amino$(C_1-C_6)$alkyl, $H_2N$—(C=O)—, $(C_1-C_6)$alkyl-NH—(C=O)—, [$(C_1-C_6)$alkyl]$_2$N—(C=O)—, $H_2N$(C=O)—$(C_1-C_6)$alkyl, $(C_1-C_6)$alkyl-HN(C=O)—$(C_1-C_6)$alkyl, [$(C_1-C_6)$alkyl]$_2$N—(C=O)—$(C_1-C_6)$alkyl, H(O=C)—NH—, $(C_1-C_6)$alkyl(C=O)—NH—, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, [$(C_1-C_6)$alkyl]$_2$N—$SO_2$—$(C_1-C_6)$alkyl, $CF_3SO_3$—,$(C_1-C_6)$alkyl-$SO_3$, -phenyl, phenyl$(C_1-C_6)$alkyl, $(C_3-C_{10})$cycloalkyl, $(C_2-C_9)$heterocycloalkyl, and $(C_2-C_9)$heteroaryl;

with the proviso that at least one of $R^1-R^8$ is hydroxy;

with the additional proviso that the compounds of formula I can not be (2R,4S)-1-[4-(4-Fluorobenzyloxy)-benzenesulfonyl]-4-hydroxy-piperidine-2-carboxylic acid hydroxyamide; (2R,3S)-1-[4-(2-Chloro-thiazol-5-ylmethoxy)-benzenesulfonyl]-3-hydroxy-piperidine-2-carboxylic acid hydroxyamide; (2R,3S)-3-Hydroxy-1-[4-(thiazol-5-ylmethoxy)-benzenesulfonyl]-piperidine-2-carboxylic acid hydroxyamide; (2R,3S)-3-Hydroxy-1-[4-(pyridin-4-ylmethoxy)-benzenesulfonyl]-piperidine-2-carboxylic acid hydroxyamide; (2R,3S)-1-[4-(4-Fluorobenzyloxy-benzenesulfonyl]-3-hydroxy-piperidine-2-carboxylic acid hydroxyamide; (2R,3S)-1-{4-[2-(4-Fluorophenyl)-ethoxy]-benzenesulfonyl}-3-hydroxy-piperidine-2-carboxylic acid hydroxyamide; (2R,3S)-3-Hydroxy-1-[4-(2-pyridin4-yl-ethoxy)-benzenesulfonyl]-piperidine-2-carboxylic acid hydroxyamide; (2R,3S)-1-[4-(Benzothiazol-2-ylmethoxy)-benzenesulfonyl]-3-hydroxy-piperidine-2-carboxylic acid hydroxyamide; (2R,3S)-3-Hydroxy-1-[4-(5-trifluoromethyl-benzothiazol-2-ylmethoxy)-benzenesulfonyl]-piperidine-2-carboxylic acid hydroxyamide; (2R,3S)-3-Hydroxy-1-[4-(1H-tetrazol-5-ylmethoxy)-benzenesulfonyl]-piperidine-2carboxylic acid hydroxyamide; (2R,3S)-1-[4-(2-Chloro-thiazol-5-ylmethoxy)-benzenesulfonyl]-3-hydroxy-3-methyl-piperidine carboxylic acid hydroxyamide; (2R,3S)-3-Hydroxy-3-methyl-1-[4-(thiazol-5-ylmethoxy)-benzenesulfonyl]-piperidine-2-carboxylic acid hydroxyamide; (2R,3S)-3-Hydroxy-3-methyl-1-[4-(pyridin-4-ylmethoxy)-benzenesulfonyl]-piperidine-2-carboxylic acid hydroxyamide; (2R,3S)-1-[4-(4-Fluorobenzyloxy)-benzenesulfonyl]-3-hydroxy-3-methyl-piperidine-2-carboxylic acid hydroxyamide; (2R,3S)-1-{4-[2-(4-Fluorophenyl)-ethoxy]-benzenesulfonyl}-3-hydroxy-3-methyl -piperidine-2-carboxylic acid hydroxyamide; (2R,3S)-3-Hydroxy-3-methyl-1-[4-(2-pyridin-4-yl-ethoxy)-benzenesulfonyl]-piperidine-2-carboxylic acid hydroxyamide; (2R,3S)-1-[4-(Benzothiazol-2-ylmethoxy)-benzenesulfonyl]-3-hydroxy-3-methyl-piperidine-2-carboxylic acid hydroxyamide; (2R,3S)-3-Hydroxy-3-methyl-1-[4-(5-trifluoromethyl-benzothiazol-2-ylmethoxy)-benzenesulfonyl]-piperidine-2-carboxylic acid hydroxyamide; (2R,3S)-3-Hydroxy-3-methyl-1-[4-(1H-tetrazol-5-ylmethoxy)-benzenesulfonyl]-piperidine-2-carboxylic acid hydroxyamide; (2R, 4S)-1-(4-Benzyloxy-benzenesulfonyl)-4-butylaminomethyl-4-hydroxy-piperidine-2-carboxylic acid hydroxyamide; (2R,4S)-4-Butylaminomethyl-1-[4-(4-fluorobenzyloxy)-benzenesulfonyl]-4-hydroxy-piperidine-2-carboxylic acid hydroxyamide; (2R,4R)-1-(4-Benzyloxy-benzenesulfonyl)-4-hydroxy-piperidine-2-carboxylic acid hydroxyamide; (2R,4R)-1-[4-(4-Fluorobenzyloxy)-benzenesulfonyl]4-hydroxy-piperidine-2-carboxylic acid hydroxyamide; (2R,5S)-1-[4-(4-Fluorobenzyloxy)-benzenesulfonyl]-5-hydroxy-piperidine-2carboxylic acid hydroxyamide; (2R,5)-1-(4-Benzyloxy-benzenesulfonyl)-5-hydroxy-piperidine-2-carboxylic acid hydroxyamide; (2R,5R)-1-(4-Benzyloxy-benzenesulfonyl)-5-hydroxy-piperidine-2-carboxylic acid hydroxyamide; (2R,5R)-1-[4-(4-Fluorobenzyloxy)-benzenesulfonyl]-5-hydroxy-piperidine-2-carboxylic acid hydroxyamide; (2R,3S)-1-(4-Benzyloxy-benzenesulfonyl)-3-hydroxy-piperidine-2-carboxylic acid hydroxyamide; (2R,4S)-1-(4-Benzyloxy-benzenesulfonyl)-4-hydroxy-piperidine-2-carboxylic acid hydroxyamide; and (2R, 4S)-1-[4-(4-Fluorobenzyloxy)-benzenesulfonyl]4-hydroxy-piperidine-2-carboxylic acid hydroxyamide;

or a pharmaceutically acceptable salt thereof.

2. A compound according to claim 1, wherein at least one of $R^1-R^6$ is $(C_1-C_6)$alkyl.

3. A compound according to claim 1, wherein at least one of $R^1-R^6$ is hydroxy and each of the other of $R^1-R^8$ is hydrogen.

4. A compound according to claim 1, wherein at least one of $R^1-R^6$ is hydroxy and at least one of the other of $R^1-R^8$ is optionally substituted $(C_1-C_6)$alkyl.

5. A compound according to claim 1, wherein at least one of $R^1-R^6$ is hydroxy and each of $R^7-R^8$ is hydrogen.

6. A compound according to claim 1, wherein at least one of $R^1-R^6$ is hydroxy and each of $R^7-R^8$ is optionally substituted $(C_1-C_6)$alkyl.

7. A compound according to claim 1, wherein $R^1$ is hydroxy.

8. A compound according to claim 1, wherein $R^1$ is hydroxy and each of the other of $R^2-R^8$ is hydrogen.

9. A compound according to claim 1, wherein $R^1$ is hydroxy and at least one of the other of $R^2-R^8$ is optionally substituted $(C_1-C_6)$alkyl.

10. A compound according to claim 1, wherein $R^1$ is hydroxy and each of $R^7-R^1$ is hydrogen.

11. A compound according to claim 1, wherein $R^1$ is hydroxy and each of $R^7-R^8$ is optionally substituted $(C_1-C_6)$alkyl.

12. A compound according to claim 1, wherein $R^1$ is hydroxy and $R^2$ is $(C_1-C_6)$alkyl.

13. A compound according to claim 1, wherein $R^1$ is hydroxy and $R^2$ is $(C_1-C_6)$alkyl and each of the other of $R^3-R^8$ is hydrogen.

14. A compound according to claim 1, wherein $R^1$ is hydroxy and $R^2$ is $(C_1-C_6)$alkyl and at least one of the other of $R^3-R^1$ is optionally substituted $(C_1-C_6)$alkyl.

15. A compound according to claim 1, wherein $R^1$ is hydroxy and $R^2$ is $(C_1-C_6)$alkyl and each of $R^7-R^8$ is hydrogen.

16. A compound according to claim 1, wherein $R^1$ is hydroxy and $R^2$ is $(C_1-C_6)$alkyl and each of $R^7-R^8$ is optionally substituted $(C_1-C_6)$alkyl.

17. A compound according to claim 1, wherein $R^1$ is hydroxy and $R^2$ is methyl.

18. A compound according to claim 1, wherein $R^1$ is hydroxy and $R^2$ is methyl and each of the other of $R^3-R^8$ is hydrogen.

19. A compound according to claim 1, wherein $R^1$ is hydroxy and $R^2$ is methyl and at least one of the other of $R^3-R^8$ is optionally substituted $(C_1-C_6)$alkyl.

20. A compound according to claim 1., wherein $R^1$ is hydroxy and $R^2$ is methyl and each of $R^7-R^8$ is hydrogen.

21. A compound according to claim 1, wherein $R^1$ is hydroxy and $R^2$ is methyl and each of $R^7-R^8$ is optionally substituted $(C_1-C_6)$alkyl.

22. A compound according to claim 1, wherein $R^2$ is hydroxy.

23. A compound according to claim 1, wherein $R^2$ is hydroxy and each of the other of $R^1$ and $R^3-R^8$ is hydrogen.

24. A compound according to claim 1, wherein $R^2$ is hydroxy and at least one of the other of $R^1$ and $R^3-R^8$ is optionally substituted $(C_1-C_6)$alkyl.

25. A compound according to claim 1, wherein $R^2$ is hydroxy and each of $R^7-R^8$ is hydrogen.

26. A compound according to claim 1, wherein $R^2$ is hydroxy and each of $R^7-R^8$ is optionally substituted $(C_1-C_6)$alkyl.

27. A compound according to claim 1, wherein $R^3$ is hydroxy.

28. A compound according to claim 1, wherein $R^3$ is hydroxy and each of the other of $R^1-R^2$ and $R^4-R^8$ is hydrogen.

29. A compound according to claim 1, wherein $R^3$ is hydroxy and at least one of the other of $R^1-R^2$ and $R^4-R^8$ is optionally substituted $(C_1-C_6)$alkyl.

30. A compound according to claim 1, wherein $R^3$ is hydroxy and each of $R^7-R^8$ is hydrogen.

31. A compound according to claim 1, wherein $R^3$ is hydroxy and each of $R^7-R^8$ is optionally substituted $(C_1-C_6)$alkyl.

32. A compound according to claim 1, wherein $R^4$ is hydroxy.

33. A compound according to claim 1, wherein $R^4$ is hydroxy and each of the other of $R^1-R^3$ and $R^5-R^8$ is hydrogen.

34. A compound according to claim 1, wherein $R^4$ is hydroxy and at least one of the other of $R^1-R^3$ and $R^5-R^8$ is optionally substituted $(C_1-C_6)$alkyl.

35. A compound according to claim 1, wherein $R^4$ is hydroxy and each of $R^7-R^8$ is hydrogen.

36. A compound according to claim 1, $R^4$ is hydroxy and each of $R^7-R^8$ is optionally substituted $(C_1-C_6)$alkyl.

37. A compound according to claim 1, wherein $R^5$ is hydroxy.

38. A compound according to claim 1, wherein $R^5$ is hydroxy and each of the other of $R^1-R^4$ and $R^6-R^8$ is hydrogen.

39. A compound according to claim 1, wherein $R^5$ is hydroxy and at least one of the other of $R^1-R^4$ and $R^6-R^8$ is optionally substituted $(C_1-C_6)$alkyl.

40. A compound according to claim 1, wherein $R^5$ is hydroxy and each of $R^7-R^8$ is hydrogen.

41. A compound according to claim 1, wherein $R^5$ is hydroxy and each of $R^7-R^8$ is optionally substituted $(C_1-C_6)$alkyl.

42. A compound according to claim 1, wherein $R^6$ is hydroxy.

43. A compound according to claim 1, wherein $R^6$ is hydroxy and each of the other of $R^1-R^5$ and $R^7-R^8$ is hydrogen.

44. A compound according to claim 1, wherein $R^6$ is hydroxy and at least one of the other of $R^1-R^5$ and $R^7-R^8$ is optionally substituted $(C_1-C_6)$alkyl.

45. A compound according to claim 1, wherein $R^6$ is hydroxy and each of $R^7-R^8$ is hydrogen.

46. A compound according to claim 1, wherein $R^6$ is hydroxy and each of $R^7-R^8$ is optionally substituted $(C_1-C_6)$alkyl.

47. A compound according to claim 1, wherein Ar is $(C_6-C_{10})$aryl$(C_1-C_6)$alkoxy$(C_6-C_{10})$aryl, $(C_6-C_{10})$aryl$(C_1-C_6)$alkoxy$(C_2-C_9)$heteroaryl, $(C_2-C_9)$heteroaryl$(C_1-C_6)$alkoxy$(C_6-C_{10})$aryl or $(C_2-C_9)$heteroaryl$(C_1-C_6)$alkoxy$(C_2-C_9)$heteroaryl, optionally substituted by one or more, preferably one to three substituents per ring, most preferably one to three substituents on the terminal ring, wherein said substituents are independently selected from halo, $(C_1-C_6)$alkyl, $(C_1-C_6)$alkoxy or perfluoro$(C_1-C_3)$alkyl.

48. A compound according to claim 2, wherein Ar is $(C_6-C_{10})$aryl$(C_1-C_6)$alkoxy$(C_6-C_{10})$aryl, $(C_6-C_{10})$aryl$(C_1-C_6)$alkoxy$(C_2-C_9)$heteroaryl, $(C_2-C_9)$heteroaryl$(C_1-C_6)$alkoxy$(C_6-C_{10})$aryl or $(C_2-C_9)$heteroaryl$(C_1-C_6)$alkoxy$(C_2-C_9)$heteroaryl, optionally substituted by one or more, preferably one to three substituents per ring, most preferably one to three substituents on the terminal ring, wherein said substituents are independently selected from halo, $(C_1-C_6)$alkyl, $(C_1-C_6)$alkoxy or perfluoro$(C_1-C_3)$alkyl.

49. A compound according to claim 3, wherein Ar is $(C_6-C_{10})$aryl$(C_1-C_6)$alkoxy$(C_6-C_{10})$aryl, $(C_6-C_{10})$aryl$(C_1-C_6)$alkoxy$(C_2-C_9)$heteroaryl, $(C_2-C_9)$heteroaryl$(C_1-C_6)$alkoxy$(C_6-C_{10})$aryl or $(C_2-C_9)$heteroaryl$(C_1-C_6)$alkoxy$(C_2-C_9)$heteroaryl, optionally substituted by one or more, preferably one to three substituents per ring, most preferably one to three substituents on the terminal ring, wherein said substituents are independently selected from halo, $(C_1-C_6)$alkyl, $(C_1-C_6)$alkoxy or perfluoro$(C_1-C_3)$alkyl.

50. A compound according to claim 4, wherein Ar is $(C_6-C_{10})$aryl$(C_1-C_6)$alkoxy$(C_6-C_{10})$aryl, $(C_6-C_{10})$aryl$(C_1-C_6)$alkoxy$(C_2-C_9)$heteroaryl, $(C_2-C_9)$heteroaryl$(C_1-C_6)$alkoxy$(C_6-C_{10})$aryl or $(C_2-C_9)$heteroaryl$(C_1-C_6)$alkoxy$(C_2-C_9)$heteroaryl, optionally substituted by one or more, preferably one to three substituents per ring, most preferably one to three substituents on the terminal ring, wherein said substituents are independently selected from halo, $(C_1-C_6)$alkyl, $(C_1-C_6)$alkoxy or perfluoro$(C_1-C_3)$alkyl.

51. A compound according to claim 1, wherein Ar is $(C_6-C_{10})$arylmethoxy$(C_6-C_{10})$aryl, $(C_6-C_{10})$arylmethoxy$(C_2-C_9)$heteroaryl, $(C_2-C_9)$heteroarylmethoxy$(C_6-C_{10})$aryl or $(C_2-C_9)$heteroarylmethoxy$C_2-C_9)$heteroaryl, optionally substituted by one or more, preferably one to three substituents per ring, most preferably one to three substituents on the terminal ring, wherein said substituents are independently selected from halo, $(C_1-C_6)$alkyl, $(C_1-C_6)$alkoxy or perfluoro$(C_1-C_3)$alkyl.

52. A compound according to claim 1, wherein Ar is optionally substituted$(C_6-C_{10})$arylmethoxyphenyl, pyridylmethoxyphenyl, thienylmethoxyphenyl, pyrazinylmethoxyphenyl, pyrimidylmethoxyphenyl, pyridazinylmethoxyphenyl, thiazolylmethoxyphenyl, or oxazolylmethoxyphenyl.

53. A compound according to claim 1, wherein Ar is $(C_6-C_{10})$arylmethoxy$(C_6)$aryl optionally substituted by one or more, preferably one to three substituents per ring, most preferably one to three substituents on the terminal ring, wherein said substituents are independently selected from halo, $(C_1-C_6)$alkyl, $(C_1-C_6)$alkoxy or perfluoro$(C_1-C_3)$alkyl.

54. A compound according to claim 2, wherein Ar is $(C_6-C_{10})$arylmethoxy$(C_6)$aryl optionally substituted by one or more, preferably one to three substituents per ring, most preferably one to three substituents on the terminal ring, wherein said substituents are independently selected from halo, $(C_1-C_6)$alkyl, $(C_1-C_6)$alkoxy or perfluoro$(C_1-C_3)$alkyl.

55. A compound according to claim 3, wherein Ar is $(C_6-C_{10})$arylmethoxy$(C_6)$aryl optionally substituted by one or more, preferably one to three substituents per ring, most preferably one to three substituents on the terminal ring, wherein said substituents are independently selected from halo, $(C_1-C_6)$alkyl, $(C_1-C_6)$alkoxy or perfluoro$(C_1-C_3)$alkyl.

56. A compound according to claim 4, wherein Ar is $(C_6-C_{10})$arylmethoxy$(C_6)$aryl optionally substituted by one or more, preferably one to three substituents per ring, most preferably one to three substituents on the terminal ring, wherein said substituents are independently selected from halo, $(C_1-C_6)$alkyl, $(C_1-C_6)$alkoxy or perfluoro$(C_1-C_3)$alkyl.

57. A compound according to claim 5, wherein Ar is $(C_6-C_{10})$arylmethoxy$(C_6)$aryl optionally substituted by one or more, preferably one to three substituents per ring, most preferably one to three substituents on the terminal ring, wherein said substituents are independently selected from halo, $(C_1-C_6)$alkyl, $(C_1-C_6)$alkoxy or perfluoro$(C_1-C_3)$alkyl.

58. A compound according to claim 6, wherein Ar is $(C_6-C_{10})$arylmethoxy$(C_2-C_9)$heteroaryl optionally substituted by one or more, preferably one to three substituents per ring, most preferably one to three substituents on the terminal ring, wherein said substituents are independently selected from halo, $(C_1-C_6)$alkyl, $(C_1-C_6)$alkoxy or perfluoro$(C_1-C_3)$alkyl.

59. A compound according to claim 1, wherein Ar is $(C_2-C_9)$heteroarylmethoxy$(C_6)$aryl optionally substituted by one or more, preferably one to three substituents per ring, most preferably one to three substituents on the terminal ring, wherein said substituents are independently selected from halo, $(C_1-C_6)$alkyl, $(C_1-C_6)$alkoxy or perfluoro$(C_1-C_3)$alkyl.

60. A compound according to claim 1, wherein Ar is $(C_2-C_9)$heteroarylmethoxy$(C_2-C_9)$heteroaryl optionally substituted by one or more, preferably one to three substituents per ring, most preferably one to three substituents on the terminal ring, wherein said substituents are independently selected from halo, $(C_1-C_6)$alkyl, $(C_1-C_6)$alkoxy or perfluoro$(C_1-C_3)$alkyl.

61. A compound according to claim 1, wherein said compound is selected from the group consisting of:
(2R,5R)-1-[4-(2,5-Dimethyl-benzyloxy)-benzenesulfonyl]-5-hydroxy-piperidine-2-carboxylic acid hydroxyamide,
(2R,5R)-1-[4-(5-Fluoro-2-methyl-benzyloxy)-benzenesulfonyl]-5-hydroxy-piperidine-2-carboxylic acid hydroxyamide,
(2R,4R)-4-Hydroxy-1-[4-(2-methyl-benzyloxy)-benzenesulfonyl]-piperidine-2-carboxylic acid hydroxyamide,
(2R,5R)-1-[4-(5-Fluoro-2-trifluoromethyl-benzyloxy)-benzenesulfonyl]-5-hydroxy-piperidine-2-carboxylic acid hydroxyamide,
(2R,5R)-5-Hydroxy-1-[4-(2-isopropyl-benzyloxy)-benzenesulfonyl]-piperidine-2-carboxylic acid hydroxyamide,
(2R,5R)-1-[4-(2-Ethyl-benzyloxy)-benzenesulfonyl]-5-hydroxy-piperidine-2-carboxylic acid hydroxyamide,
(2R,4R)-1-4-(5-Fluoro-2-methyl-1-benzyloxy)-benzenesulfonyl]-4-hydroxy-piperidine-2-carboxylic acid hydroxyamide,
(2R,4R)-1-[4-(2,5-Dimethyl-benzyloxy)-benzenesulfonyl] 4-hydroxy-piperidine-2-carboxylic acid hydroxyamide,
(2R,5R)-1-[4-(5-Fluoro-2-methyl-benzyloxy)-benzenesulfonyl]-5-hydroxy-5-methyl-piperidine-2-carboxylic acid hydroxyamide,
(2R,5R)-1-[4-(5-Fluoro-2-trifluoromethyl-benzyloxy)-benzenesulfonyl]-5-hydroxy-5-methyl-piperidine-2-carboxylic acid hydroxyamide,
(2R,5R)-5-Hydroxy-1-[4-(2-isopropyl-benzyloxy)-benzenesulfonyl]-5-methyl-piperidine-2-carboxylic acid hydroxyamide,
(2R,5R)-5-Hydroxy-5-methyl-1-[4-(2-methyl-benzyloxy)-benzenesulfonyl]-piperidine-2-carboxylic acid hydroxyamide,
(2R,3R,5R)-5-Hydroxy-3-methyl-1-[4-(2-methyl-benzyloxy)-benzenesulfonyl]-piperidine-2-carboxylic acid hydroxyamide,
(2R,3R,5R)-5-Hydroxy-1-[4-(2-isopropyl-benzyloxy)-benzenesulfonyl]-3-methyl-piperidine-2-carboxylic acid hydroxyamide, and
(2R,3S)-1-[4-(5-Fluoro-2-trifluoromethyl-benzyloxy)-benzenesulfonyl]-3-hydroxy-3-methyl-piperidine-2-carboxylic acid hydroxyamide.

62. A pharmaceutical composition for the treatment of a condition which can be treated by the inhibition of a matrix metalloproteinase in a mammal, including a human, comprising an amount of a compound of claim 1 effective in such treatment and a pharmaceutically acceptable carrier.

63. A pharmaceutical composition for the treatment of a condition which can be treated by the inhibition of a mammalian reprolysin in a mammal, including a human, comprising an amount of a compound of claim 1 effective in such treatment and a pharmaceutically acceptable carrier.

64. A pharmaceutical composition for the treatment of arthritis, inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis, aortic aneurysm, congestive heart failure, myocardial infarction, stroke, cerebral ischemia, head trauma, spinal cord injury, neuro-degenerative disorders, autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis and septic shock in a mammal, including a human, comprising an amount of a compound of claim 1 or a pharmaceutically acceptable salt thereof, effective in such treatments or inhibition and a pharmaceutically acceptable carrier.

65. A method for the inhibition of matrix metalloproteinases in a mammal, including a human, comprising administering to said mammal an effective amount of a compound of claim 1 or a pharmaceutically acceptable salt thereof.

66. A method for the inhibition of a mammalian reprolysin in a mammal, including a human, comprising administering to said mammal an effective amount of a compound of claim 1 or a pharmaceutically acceptable salt thereof.

67. A method for the inhibition of TACE in a mammal, including a human, comprising administering to said mammal an effective amount of a compound of claim 1 or a pharmaceutically acceptable salt thereof.

68. A method for treating a condition selected from the group consisting of of arthritis, inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis, aortic aneurysm, congestive heart failure, myocardial infarction, stroke, cerebral ischemia, head trauma, spinal cord injury, neuro-degenerative disorders, autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis and septic shock in a mammal, including a human, comprising administering to said mammal an amount of a compound of claim 1 or a pharmaceutically acceptable salt thereof, effective in treating such a condition.

* * * * *